US012708557B2

(12) United States Patent
Wersland et al.

(10) Patent No.: US 12,708,557 B2
(45) Date of Patent: Aug. 18, 2026

(54) TEMPERATURE CONTROLLED AND VIBRATING THERAPEUTIC STRAP ASSEMBLY

(71) Applicant: Therabody, Inc., Los Angeles, CA (US)

(72) Inventors: Jason Wersland, Manhattan Beach, CA (US); Benjamin Nazarian, Los Angeles, CA (US); Eduardo Merino, Los Angeles, CA (US); Jaime Sanchez Solana, Los Angeles, CA (US); Kevin Xie, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 18/069,827

(22) Filed: Dec. 21, 2022

(65) Prior Publication Data

US 2023/0132167 A1 Apr. 27, 2023

Related U.S. Application Data

(63) Continuation-in-part of application No. 17/823,449, filed on Aug. 30, 2022.

(Continued)

(51) Int. Cl.

*A61F 7/02* (2006.01)
*A61F 7/00* (2006.01)

(52) U.S. Cl.

CPC ................ *A61F 7/02* (2013.01); *A61F 7/007* (2013.01); *A61F 2007/0022* (2013.01);

(Continued)

(58) Field of Classification Search

CPC .............................................. A61F 2007/0042

See application file for complete search history.

(56) References Cited

U.S. PATENT DOCUMENTS

| | | | |
|---|---|---|---|
| 1,545,027 | A | 7/1925 | Ashlock |
| D143,678 | S | 1/1946 | Snyder et al. |

(Continued)

FOREIGN PATENT DOCUMENTS

| | | | |
|---|---|---|---|
| CA | 178767 | S | 9/2018 |
| CN | 201239336 | Y | 5/2009 |

(Continued)

OTHER PUBLICATIONS

International Search Report and Written Opinion of the International Searching Authority issued in International Application No. PCT/US22/75699, mailed Jan. 11, 2023, 7 pages.

(Continued)

*Primary Examiner* — Kaitlyn E Smith
(74) *Attorney, Agent, or Firm* — Sterne, Kessler, Goldstein & Fox P.L.L.C.

(57) ABSTRACT

A wearable temperature control assembly includes a temperature control module comprising a contact and a thermal element configured to heat or cool the contact. The assembly also includes a primary strap configured to receive the temperature control module and secure the contact against a subject. The assembly also includes a secondary strap configured to be connected to the primary strap. The secondary strap is configured to provide adjustment of a pressure between the contact and the subject when the primary strap secures the contact to the subject.

21 Claims, 51 Drawing Sheets

Related U.S. Application Data

(60) Provisional application No. 63/238,354, filed on Aug. 30, 2021.

(52) U.S. Cl.
CPC ................. *A61F 2007/0024* (2013.01); *A61F 2007/0078* (2013.01); *A61F 2007/0093* (2013.01); *A61F 2007/0228* (2013.01)

(56) References Cited

U.S. PATENT DOCUMENTS 2,987,334 A 6/1961 Wendling
3,705,579 A 12/1972 Morini et al.
D230,522 S 2/1974 Rothman
4,046,142 A 9/1977 Whitney
D265,002 S 6/1982 Hubner
4,976,706 A * 12/1990 Aki .......................... A61N 5/06 604/20
5,014,681 A 5/1991 Heeman et al.
5,092,317 A 3/1992 Zelikovski
5,103,809 A 4/1992 DeLuca et al.
D353,205 S 12/1994 Canavan
D417,284 S 11/1999 Kondo
6,093,164 A 7/2000 Davis et al.
D439,984 S 4/2001 Thach
6,406,445 B1 6/2002 Ben-Nun
6,558,338 B1 5/2003 Wasserman
6,591,142 B1 * 7/2003 Dea .......................... A61F 7/02 607/96
D479,877 S 9/2003 Lee et al.
6,823,762 B2 11/2004 Hu
6,846,295 B1 1/2005 Ben-Nun
D518,895 S 4/2006 Weaver, II et al.
7,022,093 B2 * 4/2006 Smith ...................... A61F 7/02 602/14
7,044,924 B1 5/2006 Roth et al.
7,207,953 B1 4/2007 Goicaj
D554,268 S 10/2007 Harding
D554,761 S 11/2007 Marin
D571,923 S 6/2008 Roberts
7,431,706 B2 10/2008 Louis
D582,047 S 12/2008 Yim
7,509,692 B2 3/2009 Elkins et al.
D598,556 S 8/2009 Chen
D608,006 S 1/2010 Avitable et al.
D613,870 S 4/2010 Shust
D635,682 S 4/2011 Chiang
7,927,259 B1 4/2011 Rix
7,927,294 B2 4/2011 Kamimura et al.
D638,948 S 5/2011 Janzon
D659,644 S 5/2012 Gretz
8,313,450 B2 11/2012 Ben-Nun
D678,531 S 3/2013 Patil
D695,902 S 12/2013 Daniels et al.
8,622,943 B2 1/2014 Ben-Nun
D704,848 S 5/2014 Thomas et al.
8,764,688 B1 7/2014 Nauman et al.
8,777,881 B2 7/2014 Tsai
D712,052 S 8/2014 Thomas et al.
D716,457 S 10/2014 Brefka et al.
9,017,273 B2 4/2015 Burbank et al.
D735,873 S 8/2015 Brefka et al.
9,125,442 B2 9/2015 Brown
D751,720 S 3/2016 Williams
D754,355 S 4/2016 Ganapathy et al.
D756,180 S 5/2016 Chen
D762,869 S 8/2016 Beckman et al.
D764,672 S 8/2016 Vosch et al.
9,414,954 B2 8/2016 Brown
9,549,870 B2 1/2017 Shafieloo
D786,447 S 5/2017 Bigelow et al.
D800,326 S 10/2017 Cox
9,849,024 B2 12/2017 Mandel
D806,888 S 1/2018 Cheng et al.
D810,311 S 2/2018 Chen
D811,613 S 2/2018 Marton et al.
D811,614 S 2/2018 Marton et al.
9,889,066 B2 2/2018 Danby et al.
9,901,510 B2 2/2018 Smith
D817,732 S 5/2018 Rettler
D820,994 S 6/2018 Trapp
D822,221 S 7/2018 Huth et al.
D831,221 S 10/2018 Smith
10,123,937 B2 11/2018 Pisharodi et al.
10,159,623 B2 12/2018 Leftly
D837,394 S 1/2019 Cryan et al.
D837,395 S 1/2019 Gan
D841,178 S 2/2019 Lazarides et al.
D841,825 S 2/2019 Rogers
10,245,208 B2 4/2019 Macguinness
10,314,762 B1 6/2019 Marton et al.
10,406,024 B2 9/2019 Evans et al.
D863,573 S 10/2019 Ito et al.
D865,986 S 11/2019 Cryan et al.
10,493,264 B1 12/2019 Lefkovitz
10,555,681 B2 2/2020 Sun
10,632,040 B2 4/2020 Muench et al.
D886,302 S 6/2020 Raghavan et al.
D890,933 S 7/2020 Shurtliff et al.
D891,626 S 7/2020 Xu
10,779,764 B2 9/2020 Marlinski
D905,253 S 12/2020 Hubelbank
D910,858 S 2/2021 Marton et al.
D917,054 S 4/2021 Woo
D923,184 S 6/2021 Li
D928,974 S 8/2021 Zulkosky et al.
D932,035 S 9/2021 Mcdonough et al.
D932,042 S 9/2021 Hu
D932,638 S 10/2021 Mcdonough et al.
D932,639 S 10/2021 Mcdonough et al.
D932,640 S 10/2021 Mcdonough et al.
D937,426 S 11/2021 Cordle
D950,740 S 5/2022 Caneppele et al.
D953,550 S 5/2022 Li
D957,651 S 7/2022 Williams et al.
D957,654 S 7/2022 Savchuk
D961,889 S 8/2022 Chen
11,510,844 B2 11/2022 Wersland et al.
11,564,831 B1 1/2023 Aguiar et al.
2004/0091663 A1 5/2004 Jang
2005/0075593 A1 4/2005 Smith et al.
2005/0193742 A1 * 9/2005 Arnold .................. A42B 3/286 62/3.5
2005/0261641 A1 * 11/2005 Warchol ................ A61F 9/0008 604/294
2007/0255187 A1 11/2007 Branch
2008/0188915 A1 * 8/2008 Mills ...................... A61F 7/007 607/112
2010/0249637 A1 9/2010 Walter et al.
2011/0000516 A1 1/2011 Hershberger et al.
2011/0233185 A1 9/2011 Augustine et al.
2012/0023785 A1 2/2012 Barnes et al.
2013/0030331 A1 1/2013 Quisenberry et al.
2013/0085552 A1 4/2013 Mandel
2014/0276257 A1 9/2014 Santa Maria et al.
2014/0316311 A1 10/2014 Nauman et al.
2014/0350441 A1 11/2014 Shafieloo
2014/0364778 A1 12/2014 Leftly et al.
2015/0174002 A1 6/2015 Burbank et al.
2015/0223975 A1 8/2015 Anderson et al.
2016/0058657 A1 3/2016 Lal et al.
2016/0089299 A1 3/2016 Munoz
2016/0135517 A1 5/2016 Silverberg
2016/0228325 A1 8/2016 Kologrivov et al.
2016/0331631 A1 11/2016 Odi
2016/0346153 A1 12/2016 Hodges, IV
2016/0367425 A1 12/2016 Wersland
2017/0014255 A1 1/2017 Booker
2017/0042754 A1 2/2017 Fowers et al.
2017/0113039 A1 4/2017 Tuan
2017/0119620 A1 5/2017 Trapp
2017/0273830 A1 9/2017 Hitschmann
2017/0280682 A1 10/2017 Ruetenik

(56) References Cited

U.S. PATENT DOCUMENTS

2017/0290736 A1 10/2017 Idris
2017/0304145 A1 10/2017 Pepe
2018/0042761 A1 2/2018 Smith et al.
2018/0042810 A1 2/2018 Nguyen
2018/0065517 A1 3/2018 Kuhley et al.
2018/0140506 A1 5/2018 Smith et al.
2018/0141188 A1 5/2018 Lai
2018/0147086 A1* 5/2018 Evans ...................... A61F 7/02
2018/0228689 A1 8/2018 Lach et al.
2018/0303704 A1 10/2018 Idris
2018/0325724 A1 11/2018 Kilbey
2019/0015289 A1 1/2019 Grimoldby et al.
2019/0070068 A1* 3/2019 Pisharodi ................ A61F 7/007
2019/0151190 A1 5/2019 Burbank et al.
2019/0183724 A1 6/2019 Sifferlin
2019/0350752 A1 11/2019 Aguiar et al.
2020/0061316 A1 2/2020 Inoue et al.
2020/0068964 A1 3/2020 Brandt et al.
2020/0078261 A1 3/2020 Duvall
2020/0113773 A1 4/2020 Ramanan et al.
2020/0214927 A1 7/2020 Clowney et al.
2020/0230021 A1 7/2020 Pisharodi et al.
2020/0237607 A1 7/2020 Ramanan et al.
2020/0253813 A1 8/2020 Kuhns
2020/0268592 A1 8/2020 Johnson et al.
2020/0368061 A1 11/2020 Levinson et al.
2021/0052430 A1 2/2021 Riley
2021/0330539 A1 10/2021 Faussett
2022/0192868 A1 6/2022 Wersland et al.

FOREIGN PATENT DOCUMENTS

CN 301664182 S 9/2011
CN 301695895 10/2011
CN 301771075 12/2011
CN 202637439 U 1/2013
CN 103284874 A 9/2013
CN 204048138 U 12/2014
CN 303250924 S 6/2015
CN 303250929 S 6/2015
CN 303679907 5/2016
CN 205285020 U 6/2016
CN 304091502 3/2017
CN 106691810 A 5/2017
CN 304124110 5/2017
CN 106859949 A 6/2017
CN 304223351 7/2017
CN 304334066 10/2017
CN 304364250 11/2017
CN 304561844 S 3/2018
CN 108514470 A 9/2018
CN 207855923 U 9/2018
CN 109528473 A 3/2019
CN 305105930 4/2019
CN 305121011 4/2019
CN 209059904 U 7/2019
CN 110131812 A 8/2019
CN 305493698 12/2019
CN 305493699 12/2019
CN 305511388 12/2019
CN 305531856 1/2020
CN 305539686 1/2020
CN 305635976 3/2020
CN 305795905 5/2020
CN 305796012 5/2020
CN 305796013 5/2020
CN 306006372 8/2020
CN 306067989 9/2020
CN 306068005 9/2020
CN 306073089 9/2020
CN 108514470 B 10/2020
CN 212038208 U 12/2020
CN 306606113 6/2021
CN 306651421 6/2021
CN 306981442 12/2021
CN 306981451 12/2021
CN 307029685 12/2021
CN 307633505 11/2022
CN 307653347 11/2022
EM EU008789861-0001 12/2021
EM EU009010564-0001 5/2022
EM EU009010564-0002 5/2022
EM EU009010564-0006 5/2022
EM EU009010564-0007 5/2022
EP 1009355 B1 11/2003
HK 2117964 12/2021
JP S5428491 A 3/1979
JP H0447440 U 4/1992
JP 2000189525 A 7/2000
JP D1086129 9/2000
JP D1355211 4/2009
JP D1355212 4/2009
JP D1395716 8/2010
JP 2011502369 A 1/2011
JP D1444377 6/2012
JP D1456095 11/2012
JP 5129032 B2 1/2013
JP D1483906 11/2013
JP 2014511240 A 5/2014
JP D1562309 11/2016
JP D1625637 3/2019
JP D1635963 7/2019
KR 200197414 Y1 11/2000
KR 300388708.0001 8/2006
KR 20-2009-0005341 U 6/2009
KR 10-0992766 B1 11/2010
KR 101162978 B1 7/2012
KR 300659290 9/2012
KR 20120100036 A 9/2012
KR 300685526 3/2013
KR 300688355 4/2013
KR 300777431 12/2014
KR 300786426 3/2015
KR 20170108550 A 9/2017
KR 300941258 1/2018
KR 300959951 6/2018
KR 301075396 9/2020
KR 301082314 11/2020
KR 301109767 5/2021
KR 301165063 5/2022
RU 00129403 1/2022
TW 1359657 B 3/2012
WO WO-2016198904 A1 12/2016
WO WO-2018064220 A1 4/2018
WO WO-2018230930 A1 12/2018
WO 2019018246 A2 1/2019
WO WO-2022133209 A1 6/2022
WO WO-2023034824 A1 3/2023

OTHER PUBLICATIONS alexnld.com: "Adjustable Waist Support Belt 3 Modes Heating Back Massage Band Lumbar Brace," Available at least as early as Dec. 6, 2021, 18 Pages, Retrieved from URL: https://alexnld.com/product/adjustable-waist-support-belt-3-modes-heating-back-massage-band-lumbar-brace/.

Amazon: "RecoveryTherm Back—Hot Vibration Back and Core Wrap for Athletes—Advanced Hot Vibration for Back Pain Relief Wrap with Cryothermal Technology—One Size Fits All", Date First Available on Sep. 20, 2022, 02 Pages, Retrieved from URL: https://www.amazon.com/RecoveryTherm-Back-Vibration-Cryothermal-Technology/dp/B0B8GRL7LR/ref=cm_cr_arp_d_product_top?ie=UTF8.

Amazon: "RecoveryTherm Knee—Contrast Therapy Wrap—Hot & Cold Vibration Recovery Knee Wrap for Athletes—Advanced Contrast Therapy for Knee Pain Relief Wrap with Cryothermal Technology—One Size Fits All," Date First Available on Aug. 3, 2022, 03 Pages, Retrieved from URL: https://www.amazon.com/RecoveryTherm-Knee-Vibration-Cryothermal-Technology/dp/B0B8GCB/YF/ref=cm_cr_arp_d_product_topie=UTF8.

Anthony Katz, "The Raptor: Helps Patients and Saves Your Most Valuable Tool . . . Your Hands," DC Aligned:MeyerDC, Dec. 9,

(56) References Cited

OTHER PUBLICATIONS 2015, available at: http://news.meyerdc.com/community/vendor-spotlight/the-raptor-helps-patients-saves-your-most-valuable-tool-your-hands/ (last visited Feb. 15, 2023); 5 pages.
Defendant's Initial Invalidity Contentions, *Therabody, Inc*. v. *Tzumi Electronics LLC et al*., Case No. SDNY-1-21-cv-07803 (PGG)(RWL), dated Aug. 17, 2022; 16 pages.
Description of Therabody GI Device, available at: https://www.therabody.com/us/en-us/faq/thearagun-devices/faq-devices-1.html?fdid=faq&csortb1=sortOrder&csortd1=1 (last visited Feb. 15, 2023).
fsastore.com: "Battle Creek Embrace Relief Knee Wrap," Available at least as early as 2020, 2021, 19 Pages, Retrieved from URL: https://fsastore.com/battle-creek-embrace-relief-knee-wrap/29568.html.
Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.
Hotsnapz: "Back Belt Set with Free Extra Reusable Heat Pad," hotsnapz.com, Available at least as early as 2022, 11 Pages, Retrieved from URL: https://hotsnapz.com/products/hotsnapz-back-belt-set-with-free-extra-heat-pack.
hyperice.com: "Hyperice X," Available at least as early as Sep. 8, 2021, 10 Pages, Retrieved from URL: https://hyperice.com/products/hyperice-x//?wickedsource=google&wickedid=EAlaIQ.obChMlo_D5z_-4-wIV9Y5bCh284gf8EAQ.YByABEgLiRvD_BwE&wickedid=&wcid=17299137048&wv=4&gclid=EAlaIQobChMlo_D5z_-4-wIV9Y5bCh284gf8EAQ.YByABEgLiRvD_BwE.
International Search Report and Written Opinion for International Application No. PCT/US2021/064027, mailed Mar. 10, 2022, 19 Pages.
International Search Report and Written Opinion for International Application No. PCT/US2021/064048, mailed Mar. 9, 2022, 9 Pages.
KT Tape: "KT Recovery+ Ice/Heat Wrap," kttape.com, Available at least as early as Jun. 21, 2021, 06 Pages, Retrieved from URL: https://www.kttape.com/products/kt-recovery-ice-heat-wrap.
Therabody: "RecoveryTherm Hot and Cold Vibration Knee," Accessed on Jan. 30, 2023, 03 Pages, Retrieved from URL: https://www.therabody.com/us/en-us/recoverytherm-knee-massager-compression.htmlcgid=therabody-recovery-devices#start=1.
Therabody: "RecoveryTherm Hot Vibration Back and Core Wrap for Athletes—Advanced Hot Vibration for Back Pain Relief Wrap with Cryothermal Technology—One Size Fits All," Accessed on Jan. 30, 2023, 02 Pages, Retrieved from URL: https://www.therabody.com/us/en-us/recoverytherm-core-lower-back-massager-compression.html?cgid=therabody-recovery-devices#start=1.
Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.
Visual Description of Hyper Ice, Inc. Raptor Device, "Raptor Solutions 1.3 Prone," available at: https://www.youtube.com/watch?v=6i1tRqdwPU8&t=156s (last visited Feb. 15, 2023); 1 page.
Youtube: "Therabody RecoveryTherm Knee Sleeve Review—Hot, Cold, Vibration," Published on Dec. 22, 2022, 01 Page, Retrieved from URL: https://www.youtube.com/watch?v =-dHbFc_LJfw.
International Search Report and Written Opinion of the International Searching Authority directed to International Patent Application No. PCT/US2023/085190, mailed Jun. 12, 2024, 17 pages.
International Search Report and Written Opinion of the International Searching Authority, directed to related International Application No. GB2418585.2, mailed Mar. 10, 2025, 4 pages.
Supplementary Partial European Search Report directed to European Application No. EP22865745.8, dated Jun. 18, 2025, 16 pages.
International Search Report and Written Opinion directed to Great Britain Application No. GB2511118.8, dated Jul. 31, 2025, 7 pages.
Office Action issued in Chinese Application No. 202180085190.X, mailed Jan. 21, 2026, 22 pages.

* cited by examiner 10
70
28
28
70
22
24
24
24
42
42
42
42
14
14
18
40
40
16
A2
40
40
57
42
42
14
14
42
42
12
70
70
28
28
30
30

210
234
242
236
238
240
248
244
217
250
246
250

210
234
242
236
238
240
248
244
217
250
246
250
251

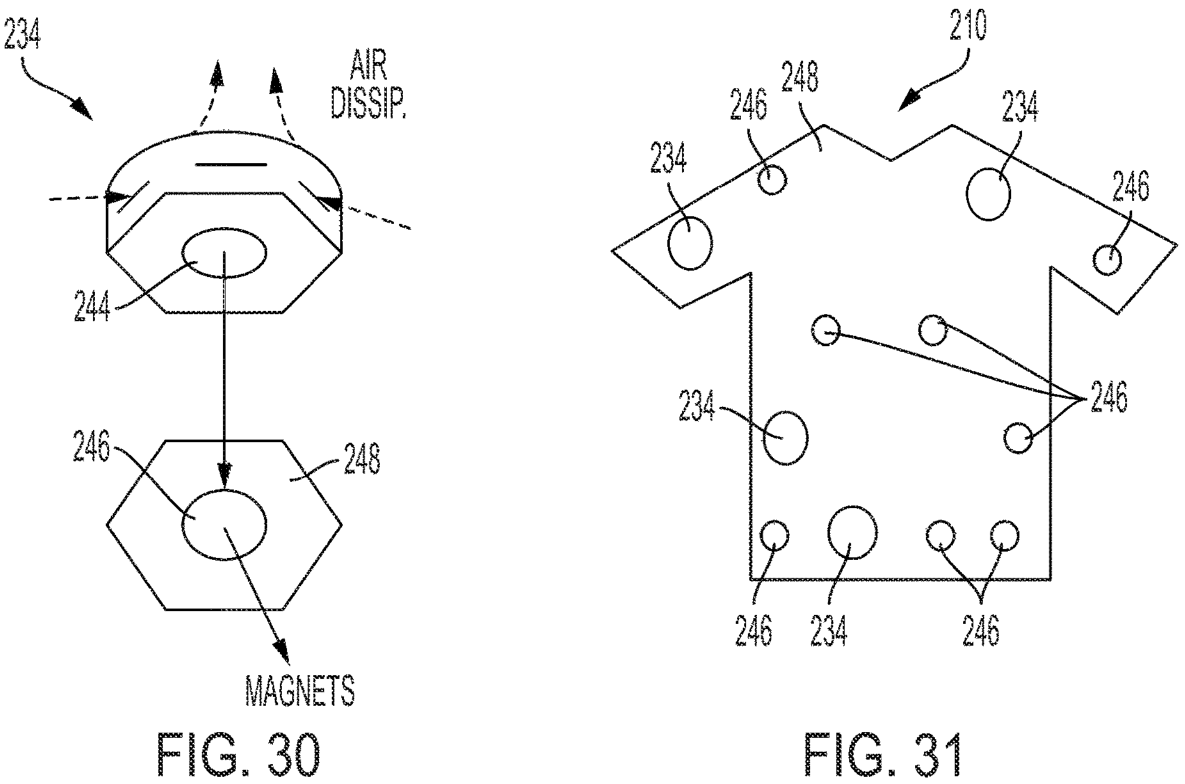
FIG. 30
FIG. 31
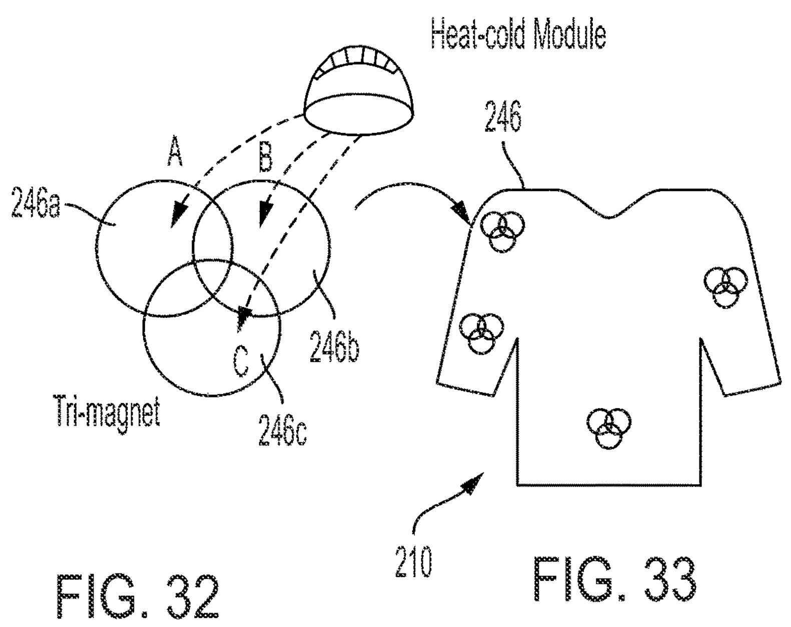
FIG. 32
FIG. 33

TEMPERATURE CONTROLLED AND VIBRATING THERAPEUTIC STRAP ASSEMBLY

CROSS-REFERENCE TO RELATED APPLICATIONS

This application is a continuation-in-part of Ser. No. 17/823,449, filed Aug. 30, 2022, which claims the benefit of U.S. Provisional Application No. 63/238,354, filed Aug. 30, 2021, the entireties of which are incorporated herein by reference.

BACKGROUND

One issue with wraps, garments and straps used for cooling or icing body parts that have a curvature to them is maintaining contact with a user's skin. The undulations or curvature can cause gaps in contact between the heating or cooling device and the skin, thereby reducing the efficiency of heat transfer between the wearer and the device. Accordingly, a need exists for a wrap that provide heat transfer to the user's body part while maintaining good contact with the user's skin.

The background description disclosed anywhere in this patent application includes information that may be useful in understanding the present disclosure. It is not an admission that any of the information provided herein is prior art or relevant to the presently claimed concepts, or that any publication specifically or implicitly referenced is prior art.

SUMMARY

Described herein is a garment that includes temperature and vibration therapy integrated therein. In some embodiments, the garment is stretchable and compresses against the wearer's skin. For example, the garment can be a shirt (long sleeve or short sleeve), pants, shorts, tank top, bra, sleeve, sock(s) or the like. In another embodiment, the garment can be a compression wrap or sleeve that surrounds a specific body part (and can include straps for securing in place), such as a knee, ankle, shoulder or the like. The compression wrap can also include heating or cooling capability The garment provides vibration therapy treatment to the wearer. The vibration devices, motors or unit cells used in the garment may generate a vibration with an amplitude smaller than 20 mm (e.g., 0.2 mm to 20 mm). The vibration can provide blood flow and oxygen increases in the wearer's body. These vibration devices are small enough that they can be integrated into wearables, fabrics, garments and pieces of clothing. As a result, the garments can be used for not only pre-exercise and post-exercise treatments, but also can be used during exercise.

The garment assembly can also be used for non-athletic uses. For example, the garments or devices may be used to reduce cellulite and for other cosmetic treatments or can also be used treat medical conditions, such as Parkinson's disease or restless leg syndrome.

In some examples, the garment or system includes a feedback function that allows the vibration treatment to be controlled and to accommodate the specific scenario or situation of the user, and turning the vibration on and off as needed. For example, during exercise or during a game, if the wearer's heart rate drops below a certain level (e.g., if the wearer is subbed out of a game or stops running for a while), the vibration can be turned on, for example, to prevent the wearer from tightening up. Therefore, the vibration can be turned on as a result of a first triggering event (e.g., when the heart rate drops below a predetermined level or a motion sensor senses that motion has stopped or dropped below a predetermined level) and can be turned off as a result of a second triggering event (e.g., when the heart rate rises above a predetermined level or a motion sensor senses that motion has started or risen above a predetermined level).

In some examples, the system includes three separate systems therein: 1. a mesh or layer of actuators (vibration devices); 2. a mesh or layer of sensors; and 3. a compressive, flexible fabric to accommodate all the elements and the electronics needed. It will be appreciated that the actuators/vibration devices and the sensors can be incorporated into a single layer.

The mesh or layer of actuators may include an array of small self-contained vibration motors. These may be brushless motors that have a depth or thickness of 1 to 4 mm and a diameter or width and length dimension of 3 to 20 mm. In some examples, the vibration motors are electronically grouped into clusters of 1 to 10 throughout the garment so that each cluster can be controlled separately from the other clusters (e.g. a sleeve wearable may have a first cluster of motors for the biceps and a second cluster for the triceps). In other examples, the motors can be distributed throughout the entire garment and different clusters can be controllable separately. In this embodiment, a single motor may be part of more than one controllable cluster. For example, on the thigh portion of the garment, there may be separate clusters for providing therapy to the quad, IT band and hamstring. However, the cluster for providing therapy to the IT band can include some of the same motors in the clusters for providing therapy to the quad and/or hamstring. Therefore, in use, a first cluster of vibration devices can be activated at a first time and for a first time period and a second cluster of vibration devices can be activated at a second time and for a second time period.

The mesh or layer of actuators may include an array of sensors. Depending on the desired application of the garment, the garment assembly or system can include one or more different types of sensors that provide feedback on different biometrics of the user. The feedback can be used to activate/deactivate the clusters of actuators (or a single actuator) throughout the garment. For example, a pair of running shorts can include motion sensors that trigger or actuate the vibration motors when it is sensed that the user has stopped or slowed down to a walking pace, is between runs in a workout series, or is cooling down after running. The garment assembly can include skin and/or muscle temperature sensor(s), pulse or heart beat sensor(s) (e.g., optical or infrared), pulse oximeter(s), motion sensor(s) (e.g., gyroscope sensor/accelerometer) and other sensors as desired.

The elastic, compressive fabric can be made of, e.g., nylon, spandex, neoprene or other flexible fabric or material. The garment can include multiple fabric layers, for example, inner and outer layers to accommodate or house the components (e.g., the actuator and sensor layer(s)) and provide a space or pathways for the electronics and circuit boards. The fabric may also include breathable areas as well as sealed sections to waterproof cabling and electronics.

In another embodiment, the garment assembly can include temperature control or modulation. In particular, the garment assembly can include temperature control modules that may be permanent or removable.

In some embodiments, the wrap assembly includes wireless communication (e.g.,

Bluetooth) so that it can communicate with a software application on a mobile device, such as a phone to provide a "smart" garment system. The wireless communication device can be housed on a PCB that is also in electrical and/or data communication with the vibration devices, temperature control modules, main control module or the like.

The wearable device or garment assembly can include temperature modulation and application, for example, via temperature control modules positioned thereon or integrated therein. The garment assembly can include both vibration and heat/cold or can include one or the other. In some examples, the wrap portion includes a magnet positioned thereon or therein. At some locations on the garment portion, temperature control modules can be secured to the magnets. Temperature control modules can be disposed throughout the garment assembly. In some examples, there is no garment or fabric layer between the temperature control module and the user's skin. Instead, the bottom layer or surface of the temperature control module or some other heat conductive portion or material contacts the user's skin.

In another embodiment, the temperature control module includes a fan, a heat sink and a Peltier module or device that are contained within the module housing. In this embodiment, the temperature control module includes a magnet on the bottom thereof that can be magnetically connected or secured to a magnet on or in the fabric portion or garment portion of the garment assembly. A frame (e.g., plastic frame) can be embedded in or attached to the garment portion for helping with connection of the temperature control module.

In another embodiment, the magnet to magnet system secures the temperature control module to the wrap or garment portion and transfers or conducts the heat or cold from the module to the user's skin as the magnets may be made of a heat and/or cold conductive material. In an embodiment, the wrap assembly can include a flexible heat or cold conductive members, such as a band, patch or the like (e.g., made of copper or aluminum) to help transfer heat or cold to increase the effective area of the heat/cold treatment. The heat conductive members may be in contact with or connected to the magnet so that the heat or cold is conducted from the magnet and through the heat conductive member.

In an embodiment with a number of connecting magnets in different locations, the user is provided with a plurality of options for where to position one or more temperature control modules. For example, if the user has a right shoulder issue they are treating, they may only place one or more temperature control modules in that location. At a later time they can use the same shirt to treat an abdominal issue. The vibration devices may be embedded in the garment portion (e.g., between inner and outer fabric layers) and can be arranged around the magnets such that temperature control modules can be connected to the magnet above and below the knee cap. This is just an example and any pattern or number of vibration devices and temperature control modules can be utilized. It will be appreciated that any configuration of vibration devices is within the scope of the present disclosure. The vibration devices can be configured to treat certain issues and can be placed in patterns around the sleeve or wrap, such as a triangle, star, circle, spiral, other pattern, etc. and can increase blood flow and provide therapeutic benefit as desired.

In another embodiment, the garment assembly includes a plurality of magnets that may be overlapping or a single magnet with a plurality of locations where the magnet on the temperature control modules can be placed in order to allow the temperature control modules to be movable or positionable within the same general area. This allows the user to move the module to the exact location of the issue. It also allows a single garment size to be usable by different uses because no two bodies are exactly the same. In another embodiment, the majority of or all of the garment can be magnetized, thus allowing the module to attach anywhere.

In another embodiment, the disclosure includes a smart vibration system. It will be appreciated by those of ordinary skill in the art that at a certain frequency (depending on the mass attached to the system), vibrations can make a user's body resonate and therefore increase the amplitude of the perceived vibration. To take advantage of this resonant frequency principle (which is different from person to person and from body part to body part), the present disclosure may include a closed loop system with sensors that scan through the different speeds of the vibration devices or motors until the resonant frequency is found. This may be accomplished by adding accelerometers near the motor locations that can measure the actual vibration it is being generated when the motor is attached to the body part. In an exemplary embodiment, strain gages that can measure displacement of the garment are included in the location of the motor.

In some examples, the garment assembly is washable and includes at least some components that are embedded in, attached to, etc. permanently in the garment (e.g., waterproof enclosed motors, cabling, etc.) and other components that are removable (battery pack, PCB). The permanent components may be sealed in the garment (e.g., between garment layers and the user can wash the garment after removing the power unit system (battery pack, PCB, etc.).

In another embodiment, the garment assembly can be a wrap or strap garment assembly that includes a heating/cooling system and localized vibration. In some embodiments, the garment assembly is incorporated in a compression wrap. One or more of the layers of the device can include vibration capability. The temperature control modules may or may not contain an integrated battery (i.e., within the module). The modules can be removed from the strap device and placed in different cavities in the strap assembly depending on the desired treatment.

The temperature control modules may be different sizes depending on the muscle group or the surface area desired be treated. The device (or separate devices) may also include different sized and shaped straps to accommodate different body parts.

The wrap assembly may be embodied in a wrist and/or knee strap assembly. In some embodiments, the wrap portion may include positions or cavities defined therein that are each configured to receive a temperature control module. The main controller can be electrically connected to and in data communication with the temperature control modules so that the modules are powered and can be controlled by the controller. The wiring can be embedded in the main body portion and plugs or jacks can be used for attaching and detaching the electrical connections. The wiring can also be external. Wireless connectivity between any and/or all components can also be included. In another embodiment, a battery can be located in the module, thus making each module independent and interchangeable such that it can be simply placed in the cavity or a strap garment assembly or secured via a magnet or other attachment mechanism to a "wearable" garment assembly.

In another embodiment, the module housing includes a groove therearound that receives a portion of the wrap portion so that it can be positioned in the cavity (or module seat). It will be appreciated that the wrap portion is made of a material that is pliable and flexible enough to allow the modules to be inserted into the cavities and removed therefrom (e.g., pressed into place and removed therefrom). In embodiments with larger and smaller modules, the one or more larger modules are the main heat or cold provider (to the user). The heat may be conducted outwardly from the larger module. The smaller modules can be used to provide extra heat or cold where it is difficult to conduct the heat from the larger module. In some examples, the main body portion and/or straps include heat conductive material therein or thereon.

In an embodiment, the wrap assembly may include different sized modules, such as one larger module and several smaller modules. Some or all of the temperature control modules may also include vibration devices or motors therein (e.g., inside the housing). In another embodiment, one or more vibrating devices can be placed on or in the heat sink. Vibration devices can also be included embedded in the main body portion or strap portions. It will be appreciated that any and all of the embodiments discussed or disclosed herein and any of the components or concepts included in the embodiments are all completely interchangeable, swappable and usable together. It will be appreciated that strap assemblies or wrap portions can be configured to fit any body part or multiple body parts, e.g., shoulder, back, knee, elbow, wrist, neck, ankle, etc.

In another embodiment, the temperature control module may include a concave module structure or bottom surface so that it can adapt to the contour of different portions of the body, such as the thigh, calf, shin, etc. In some examples, the temperature control module also includes a fan bracket and a Peltier housing that includes an upper housing portion that houses the Peltier device and a lower housing portion that houses the vibration device and a PCB. The module housing may include a lower portion that includes the concave surface on a bottom thereof. The lower portion also includes a conductive member that conducts heat or cold from the Peltier device to the concave bottom surface. The upper and lower housing portions of the Peltier housing define a vibration device recess. All temperature control modules herein include vents or openings in the module housing to allow heat to be dissipated therefrom. It will be appreciated that the straps can be include Velcro or the like for securement.

In another embodiment, the main control module or assembly includes a plurality of buttons and/or switches thereon for controlling the temperature control modules and/or vibration devices. For example, the buttons can control turning the device on and off, cooling and heating, time or duration, changing modes, controlling the vibration devices and turning them on and/or off for various body parts. LED lights can also be included as charging or time indicators. Some of the features are controlled by multiple pushes of the associated button. In an exemplary embodiment, the buttons may work as follows. Pushing the mode button may cycle through the following vibration patterns—constant, wave, regular, wave, off. The cold button—one press for 5° C. control, two presses for 10° C. control, three presses for unlimited control and four presses to turn off. The hot button—one press for 38° C. control, two presses for 40° C. control, three presses for 42° and four presses to turn off. The time button—power on sets the time to 15 minutes, one press sets to 30 minutes, two presses sets to 60 minutes, third press for unlimited time.

One of the advantages of certain concepts within the present disclosure is the ability to provide flexibility so that the modules can be used on, for example, strap devices and garment or wearable devices. Mounting the modules on strap devices provides high performance and efficacy. The strap allows for multiple modules to work together and treat a wide area. Mounting the modules on a wearable device (e.g., shirt, pants, shorts, etc.) provides the user with a vibration garment and the flexibility of adding temperature control modules when desired.

It will be appreciated that a wrap assembly according to an aspect of the present disclosure is a battery powered wearable that can replace ice packs and is shaped to treat body parts such as the waist, shoulder, and upper or lower back. The assembly can also be used for heat therapy and may have temperature control modules, vibration motors, or both, embedded in the strap or garment to boost blood flow and recovery. In some embodiments, the strap assembly includes a removable battery, one or more temperature control modules, and optionally one or more vibration motors in the garment or strap. The motors may be divided into groups, such as groups of three, and the speed or on/off functions of the groups can be controlled independently. The device may also include Bluetooth connectivity that allows it to be connected to an app on a mobile device. Exemplary use cases for athletes and non-athletes include post shoulder surgery treatment, post work-out recovery, and users with chronic shoulder, neck and upper back pain.

It will be appreciated that the body parts that the strap assemblies may be used on include curved surfaces. In some examples, the temperature control module includes extension members or finger spreaders that essentially increase the footprint of the cooling/heating modules and allow some devices according to this disclosure to distribute the desired temperature around curved areas in the body (e.g., calf, thigh, shoulder, trapezoid). In an exemplary embodiment, the finger spreaders allow treatment area to extend around a curved surface.

In some examples, the temperature control module includes modular extension legs, extension members or spreaders made of, e.g., stacks of thin copper. The spreaders can be divided into smaller fingers to add flexibility in the perpendicular direction and help adapting to the body. The spreaders can be attached to the main plate under the primary spreader by different methods, such as bolted (or other threaded receiver), riveted, hinged, welded, etc.

Vibration motors can be included in the strap, garment portion, within the housing or on the spreaders. The spreaders, spreader members, finger spreaders, legs or extension members can be made of aluminum or another metal and the pivot points or the like of the spreaders can be made of copper or other metal.

In another embodiment, the spreaders can be enclosed or sewn into the garment portion. The fabric or strap may be on top of the spreader, thereby allowing the bottom surface of the spreader to touch the skin of the user. In this embodiment, when the strap or garment portion is wrapped around the body part (e.g., leg), the spreaders will be moved or pivoted by the fabric to help the spreaders move closer to or against the leg. The user can also push the spreaders through the fabric to help the spreader to the desired position.

In some examples, the spreader member and/or finger spreaders can include a plurality of metallic layers. In such an embodiment, thin copper layers (e.g., die cut layers) are stacked on one another and form the separate primary spreader member and extension legs or finger spreaders. The extension legs can optionally be pivotable or otherwise movably connected with respect to the primary spreader, and the primary spreader may be considered part of a hub portion of the temperature control module overall. Therefore, by creating the thin layers, the desired shape, depending on the body part targeted, can be created. The stack of layers can include layers of aluminum or thicker copper above and below in the areas were rigidity needs to be increased. Also, the copper layers can be formed in different shapes to adapt exactly to the geometry of the muscle(s) to be treated.

Any type of attachment system that can be used to secure the garment assembly to the user's leg or other body part is within the scope of the present disclosure. The attachment system may include a magnetic securement and adjustment system therein. The attachment system may include a mechanical latch or securement system and magnets for aligning the components to make connection easier. For example, a Fidlock magnetic buckle or system can be used.

In another embodiment, the wrap assembly includes one or more pillow or cushion members on the inside of the wrap portion, which provide comfort for the user and may also be removable so that they can be washed or replaced. The cushion members may include magnets or other attachment mechanism (Velcro, snaps, buttons, etc.) so that the cushion members can be secured or removably attached to the wrap portion. Upper and lower or first and second cushion portions can be included for the upper and lower portions. The cushion members provide a layer generally parallel to the thermal spreader surface that improves comfort and may be a layer that is sacrificed or replaced due to the buildup of sweat and moisture over time. Any soft material is within the scope of the disclosure. In some examples, the cushion member includes a memory foam layer wrapped in a fabric enclosure. The magnets may be embedded in the memory foam or between layers (and a complementary magnet is included in the wrap portion). The thickness is selected to provide comfort while allowing the vibration motors to contact the user's skin.

The wrap assembly may include a mounting skirt and/or mounting member for mounting or otherwise attaching the temperature control modules and/or main control module to the wrap portion (e.g., by sewing). A donut or ring member may be positioned around the knee or central opening and helps align the wrap assembly on the user's knee cap when worn. The ring member may be semi-rigid to rigid and allows the knee cap of the user to at least partially extend therethrough to help support the wrap assembly on the user's leg and to help prevent the strap from sliding down the user's leg. The ring member may be made of a plastic material so that it is rigid for support, but somewhat flexible so it can move and bend when the user bends their knee. The wrap portion may include inner and outer layers so that some of the components (e.g., wiring, the donut for the central opening, etc.) can be sandwiched therebetween.

It will be appreciated that any type of system for holding the temperature control modules in place on a body part is within the scope of the present disclosure. Any type of straps, clamps, buckles and the like or combination thereof is within the scope of the present disclosure. Furthermore, the wrap portion or fabric portion of the assembly can be modified or changed to make the product smaller, streamlined or generally of a lighter weight. In some examples, any portion or all of the wrap assembly/fabric portion can include, be comprised of, include a layer of or use a far infrared reflecting or FIR fabric.

In another aspect, a wearable temperature control assembly may comprise a primary strap including an opening extending through the primary strap and a tunnel extending along a length of the primary strap. The tunnel may include two tunnel ends. The assembly may also comprise a secondary strap configured to be disposed through the tunnel and including two secondary strap ends that are configured to be securable to the primary strap. Each of the secondary strap ends may be configured to extend beyond the respective tunnel ends when coupled together. The wearable temperature control assembly may also comprise a temperature control module configured to be disposed through the opening. The temperature control module may comprise a contact and a thermal element configured to heat or cool the contact.

In some arrangements according to any of the foregoing, the tunnel may be a first tunnel, the secondary strap may be a first secondary strap, the primary strap may include a second tunnel extending along the length of the primary strap and located on an opposite side of the opening from the first secondary strap, and the assembly may comprise a second secondary strap configured to be disposed through the second tunnel.

In some arrangements according to any of the foregoing, the opening may be a first opening, the temperature control module may be a first temperature control module, the primary strap may include a second opening located between the first tunnel and the second tunnel, and the assembly may comprise a second temperature control module configured to be disposed through the second opening.

In some arrangements according to any of the foregoing, the contact may include a spreader configured to extend transverse to a thickness of the primary strap beyond a perimeter of the opening when the temperature control module is disposed through the opening. The extending spreader may optionally be a finger spreader, and the contact may optionally also include a central spreader away from which the finger spreader extends.

In some arrangements according to any of the foregoing, the first tunnel and the second tunnel may be spaced apart across the opening by a spacing distance, and the spreader may be configured to extend relative to the temperature control module in a direction that is transverse to the length of the primary strap when the temperature control module is disposed through the opening such that a total width of the contact in a direction parallel to the spacing distance is greater than the spacing distance.

In some arrangements according to any of the foregoing, the spreader may be one spreader among a plurality of spreaders included by the contact and configured to be located proximate the opening when the temperature control module is disposed through the opening. Accordingly, the contact may optionally include a plurality of individual finger spreaders.

In some arrangements according to any of the foregoing, the spreaders among the plurality of spreaders may each be configured to be movably connected to a hub portion of the temperature control module at a respective connection point and configured to be biased about the respective connection point in a direction relative to the hub portion of the control module that is away from the primary strap when the temperature control module is disposed through the opening.

In some arrangements according to any of the foregoing, the secondary strap may have a greater elasticity than the primary strap.

In some arrangements according to any of the foregoing, the secondary strap may have a lower spring constant than the primary strap.

In some arrangements according to any of the foregoing, the secondary strap may be shorter in all directions than the primary strap.

In some arrangements according to any of the foregoing, the thermal element may be a thermoelectric heater or cooler.

In some arrangements according to any of the foregoing, the thermal element may be a heat pump.

In some arrangements according to any of the foregoing, the primary strap may include a first pair of fasteners configured to releasably connect two portions of the first strap to one another so as to enable the primary strap to be secured around a torso. Additionally, the secondary strap may include a second pair of fasteners configured to releasably connect two portions of the secondary strap to the primary strap in a configuration wherein the secondary strap extends around the torso and a portion of the temperature control module.

In some arrangements according to any of the foregoing, the first pair of fasteners and the second pair of fasteners may each include a patch of hook material and a patch of loop material configured to form a hook and loop connection with one another when pressed together.

In some arrangements according to any of the foregoing, the contact may include a spreader configured to extend transverse to a thickness of the primary strap across a perimeter of the opening and configured to be movably connected to a hub portion of the temperature control module at a connection point and biased about the connection point in a direction relative to the hub portion of the temperature control module that is away from the primary strap when the temperature control module is disposed through the opening.

In another aspect, a wearable temperature control assembly may comprise a temperature control module comprising a contact and a thermal element configured to heat or cool the contact. The assembly may also comprise a removable battery associated with the temperature control module. The assembly may also comprise a primary strap configured to receive the temperature control module and secure the contact against a subject. The assembly may also comprise a secondary strap configured to be connected to the primary strap and further configured to provide adjustment of a pressure between the contact and the subject when the primary strap secures the contact to the subject.

In some arrangements according to any of the foregoing, the primary strap may be an elongate article including two portions that are configured to be releasably connectable to one another so that the primary strap forms a loop when the two portions are connected to one another.

In some arrangements according to any of the foregoing, the temperature control module may be configured to extend through the primary strap and includes a heat sink located relative to the contact so as to be positioned on an opposite side of the primary strap from the contact when the heat sink is disposed through the opening.

In some arrangements according to any of the foregoing, the secondary strap may be a first secondary strap and the assembly comprises a second secondary strap that is configured to be located on an opposite side of the temperature control module from the first secondary strap, connected to the primary strap, and further configured to adjust a pressure between the contact and the subject when the primary strap encircles the subject.

In some arrangements according to any of the foregoing, the first secondary strap and the second secondary strap may be configured to be spaced apart by a distance in a width direction, and the contact is wider than the distance.

In another aspect, a wearable therapeutic device may comprise a strap configured to wrap around a wearer's abdomen and comprising a middle portion, a first end portion extending from the middle portion, and a second portion extending from an opposite side of the middle portion as the first end portion. The device may also comprise a control module located on the strap, and the control module may comprise a removable battery. The device may also comprise a first fastener attached to the first end portion and a second fastener that is complementary to the first fastener and attached to the second end portion. The device may also comprise a first heating element located in the first end portion and a second heating element located in the middle portion.

In some arrangements according to any of the foregoing, vibration motors may be embedded within the middle portion.

In some arrangements according to any of the foregoing, the vibration motors may be located to overlap the second heating element.

In some arrangements according to any of the foregoing, the device may comprise a layer of knitted fabric that includes fibers containing germanium.

In some arrangements according to any of the foregoing, the device may comprise a layer of infrared radiation emitting fabric.

In some arrangements according to any of the foregoing, the infrared radiation emitting fabric may emit the infrared radiation passively.

In some arrangements according to any of the foregoing, the device may comprise a pad between each motor and the second heating element.

In some arrangements according to any of the foregoing, the device may comprise a padding layer between the heating element and a surface of the strap.

In some arrangements according to any of the foregoing, the vibration motors may be located between the second heating element and the padding layer.

In some arrangements according to any of the foregoing, the first heating element and the second heating element may be panels of carbon fiber or carbon fiber mesh.

In some arrangements according to any of the foregoing, a gap may exist between the first heating element and the second heating element.

In some arrangements according to any of the foregoing, the second end portion may be free of any heating elements.

In another aspect, a wearable therapeutic device may comprise a strap configured for wrapping around a wearer's abdomen and including a wearer facing surface layer that is made at least partially of germanium. The device may also comprise a control module located on the strap. The control module may comprise a removable battery. The device may also comprise at least one vibration motor embedded in the strap.

In some arrangements according to any of the foregoing, the wearer facing surface layer may be a knitted fabric including fibers of germanium or germanium alloy.

In some arrangements according to any of the foregoing, the device may comprise heating features for heating a wearer's back and stomach.

In some arrangements according to any of the foregoing, the heating features may include a first heating element in a middle portion of the strap and a second heating element spaced from the first heating element and located in a first end portion of the strap, and the strap includes a second end portion extending from an opposite side of the middle portion as the first end portion.

In some arrangements according to any of the foregoing, the heating features may include a panel of carbon fiber or carbon fiber mesh.

BRIEF DESCRIPTION OF THE DRAWINGS

FIG. 30 illustrates a feature for connecting temperature control modules to the therapeutic garments of FIGS. 21 and 29;

FIG. 31 illustrates a therapeutic garment having the connecting feature of FIG. 30;

FIG. 32 illustrates a therapeutic garment having connecting features according to another arrangement;

FIG. 33 is an enlarged illustration of a connecting feature of the therapeutic garment of FIG. 32;

Like numerals refer to like parts throughout the several views of the drawings.

DETAILED DESCRIPTION OF THE INVENTION

Figure 1:
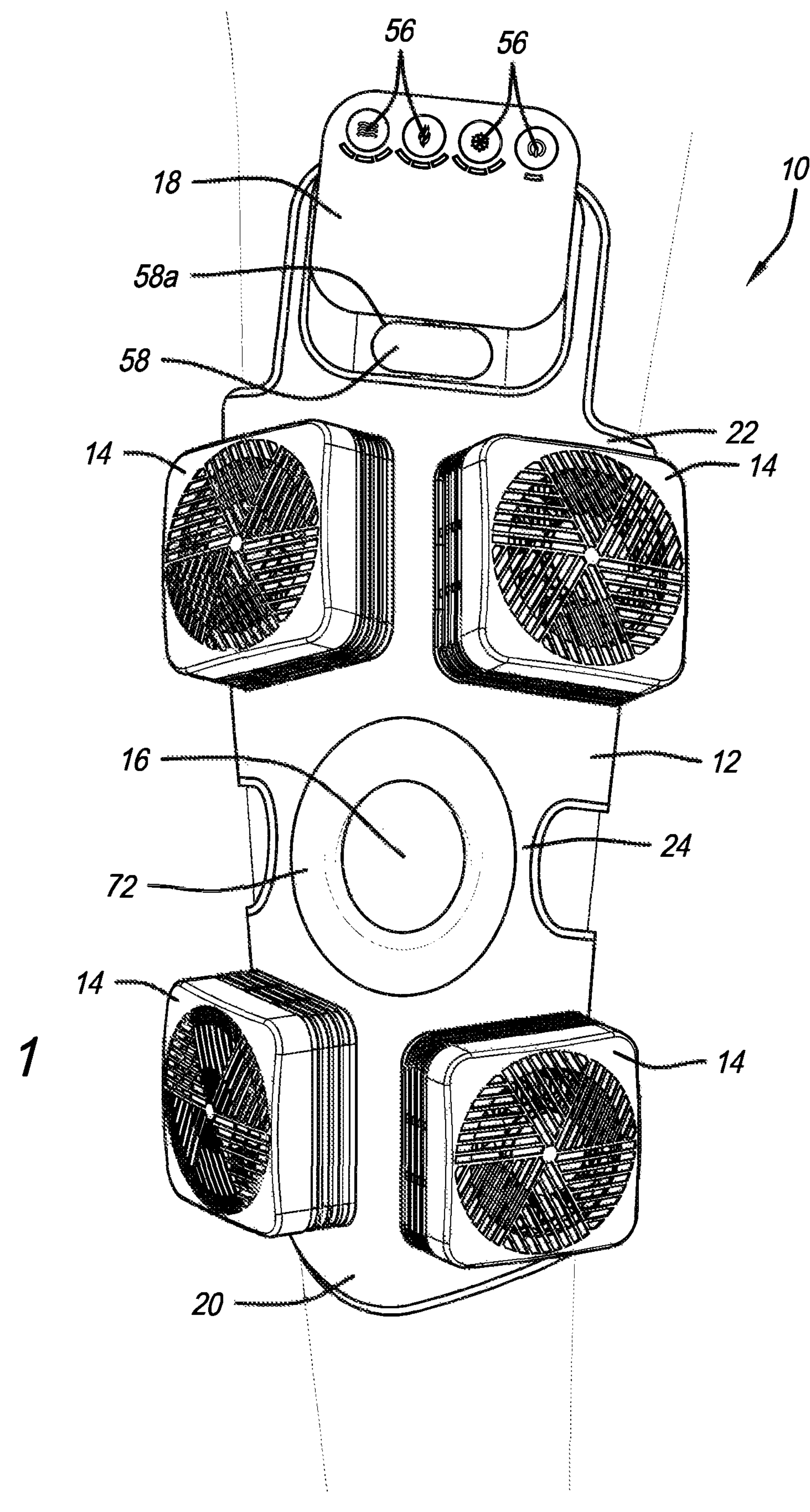
FIG. 1 is a perspective view of a temperature controllable wrap assembly secured on a user's leg in accordance with a device according to an aspect of the present disclosure attached thereto.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the disclosure may be applied to another aspect or embodiment of the disclosure. Similarly, where appropriate any of the features discussed herein in relation to one aspect or embodiment of the disclosure may be optional with respect to and/or omitted from that aspect or embodiment of the disclosure or any other aspect or embodiment of the disclosure discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present disclosure.

Described herein and shown in FIGS. 1-10 is a temperature controllable wrap assembly 10 that may include temperature control and vibration therapy integrated therein. FIGS. 1-10 show the garment assembly embodied in a closeable sleeve or wrap that is configured to be used on a wearer's knee. However, it will be appreciated that this is not a limitation on the present disclosure and the wrap assembly 10 can be any type of wearable garment, wrap or strap that includes the temperature control modules disclosed herein.

Figure 2:
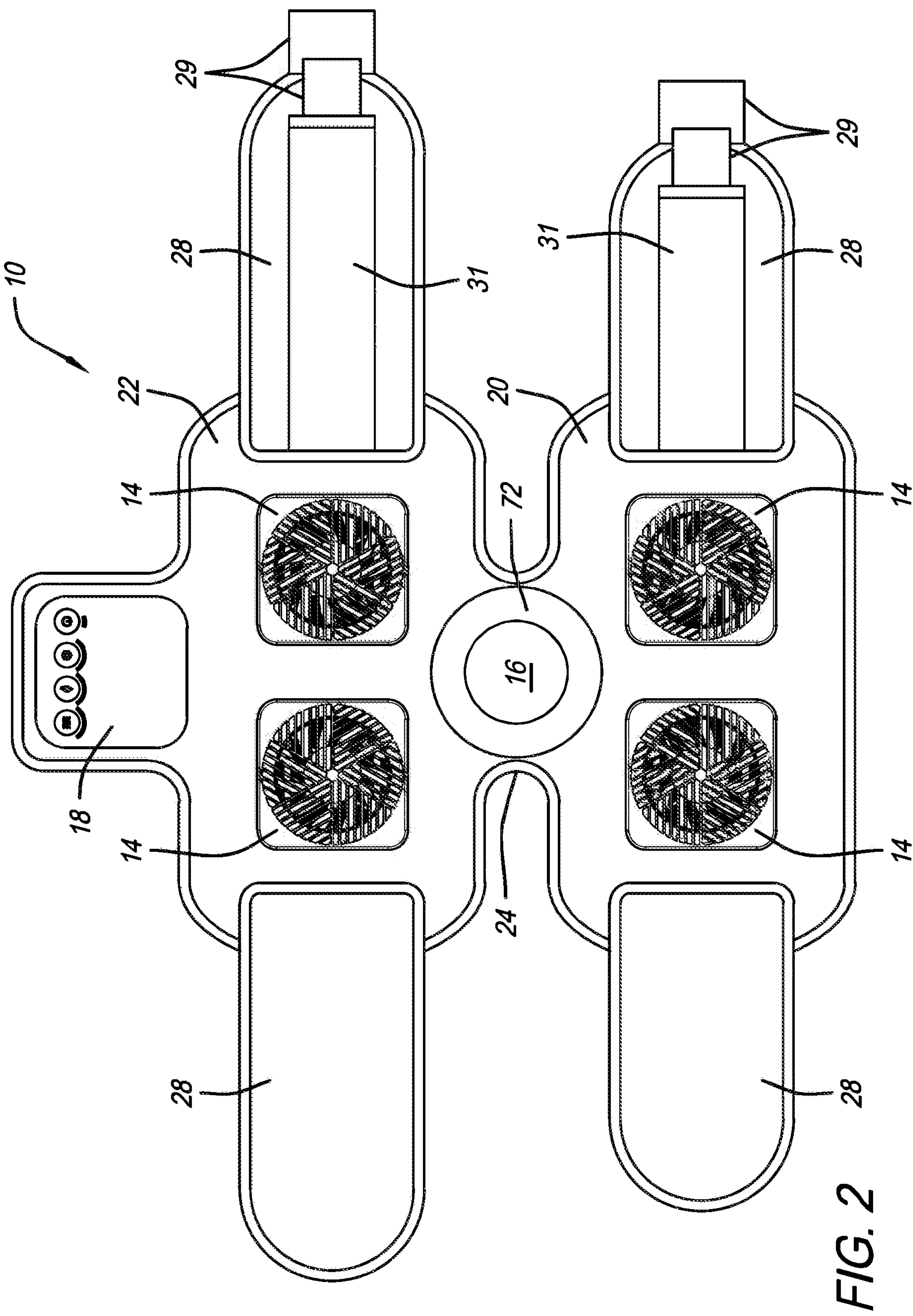
FIG. 2 is a front elevational view of the temperature controllable wrap assembly of FIG. 1.
Figure 3:
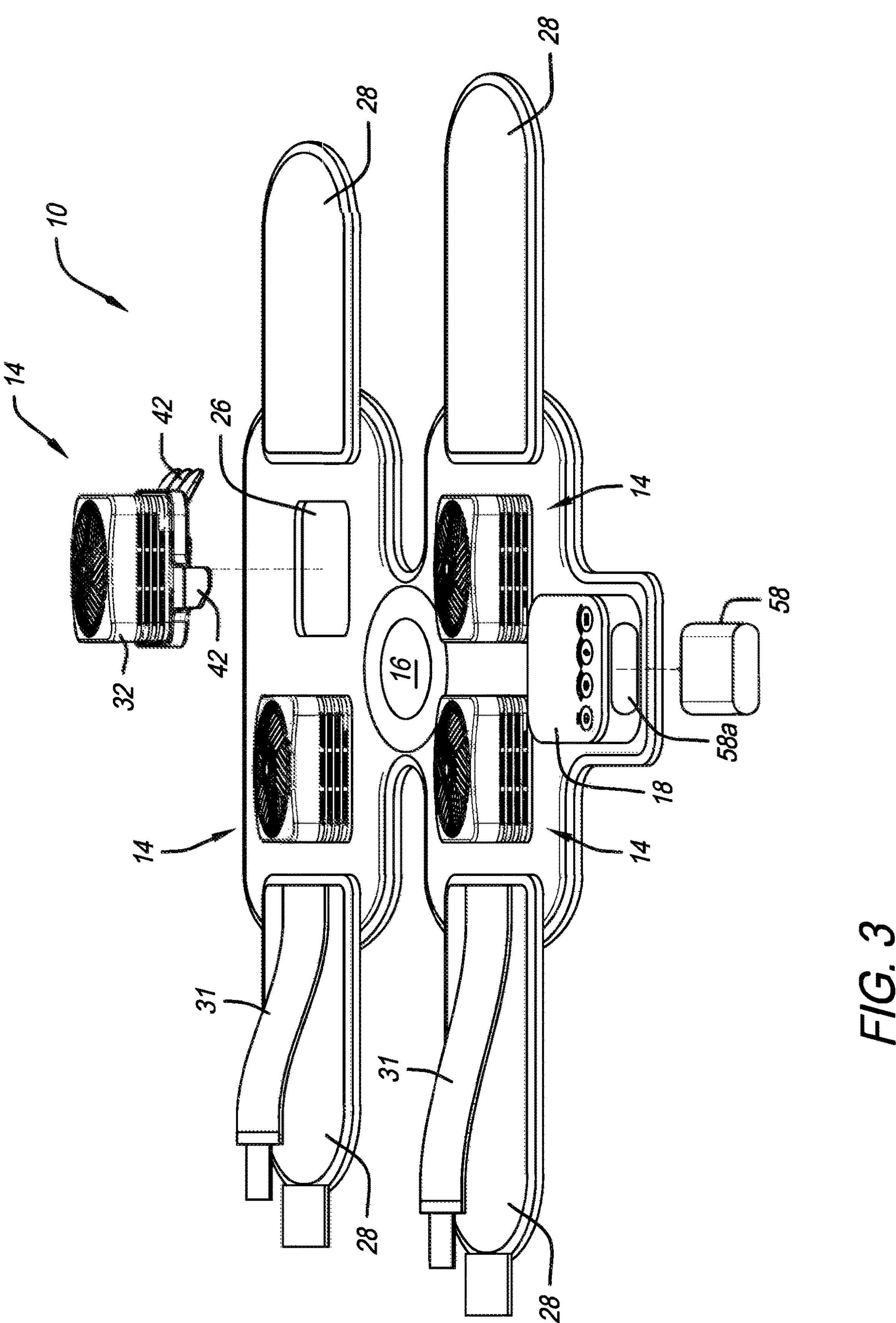
FIG. 3 is a front perspective view of the temperature controllable wrap assembly of FIG. 1 in the open position.

As shown in FIG. 1, in some examples, the temperature controllable wrap assembly 10 includes a garment or wrap portion 12 configured to be worn around a user's leg, a plurality of temperature control modules 14 positioned on or extending through the wrap portion 12, a central opening 16, and a main control module 18. As shown in FIGS. 2 and 3, in some examples, the wrap portion 12 includes a lower portion 20, an upper portion 22 and a knee portion 24 extending between the lower portion 20 and the upper portion 22. The central opening 16 may be at least partially defined in or through the knee portion 24.

The temperature control modules 14 may be mounted in retention openings 26 defined in the wrap portion 12 (which may include one or more layers). As shown in FIG. 2, two temperature control modules 14 and the main control module 18 may be positioned on the upper portion 22 and two temperature control modules 14 are positioned on the lower portion 20. In some embodiments, strap portions 28 extend outwardly from the upper and lower leg portions. One of the strap portions 28 may include a handle 29 for pulling the strap portion to provide the desired amount of tension and securing to the strap portion on the other side. The strap portions 28 may include hook and loop material 30 (Velcro) thereon so that the temperature controllable wrap assembly 10 can be secured around the user's leg. As shown in FIG. 2, the wrap portion 12 can also include secondary straps 31 that provide the ability to further tighten the straps on one side to the Velcro strap on the other side. any arrangement of hook material on one strap and loop material on another strap is within the scope of the present disclosure to allow the strap portions 28 and secondary straps 31 to work is within the scope of the present disclosure. In another embodiment, the strap portions can be omitted and the wrap portion can be a closed sleeve that is stretchable to fit over the user's leg. It will be appreciated that any type of system for holding the temperature control modules in place on a body part is within the scope of the present disclosure. Any type of straps, clamps, buckles and the like or combination thereof is within the scope of the present disclosure.

Figure 4:
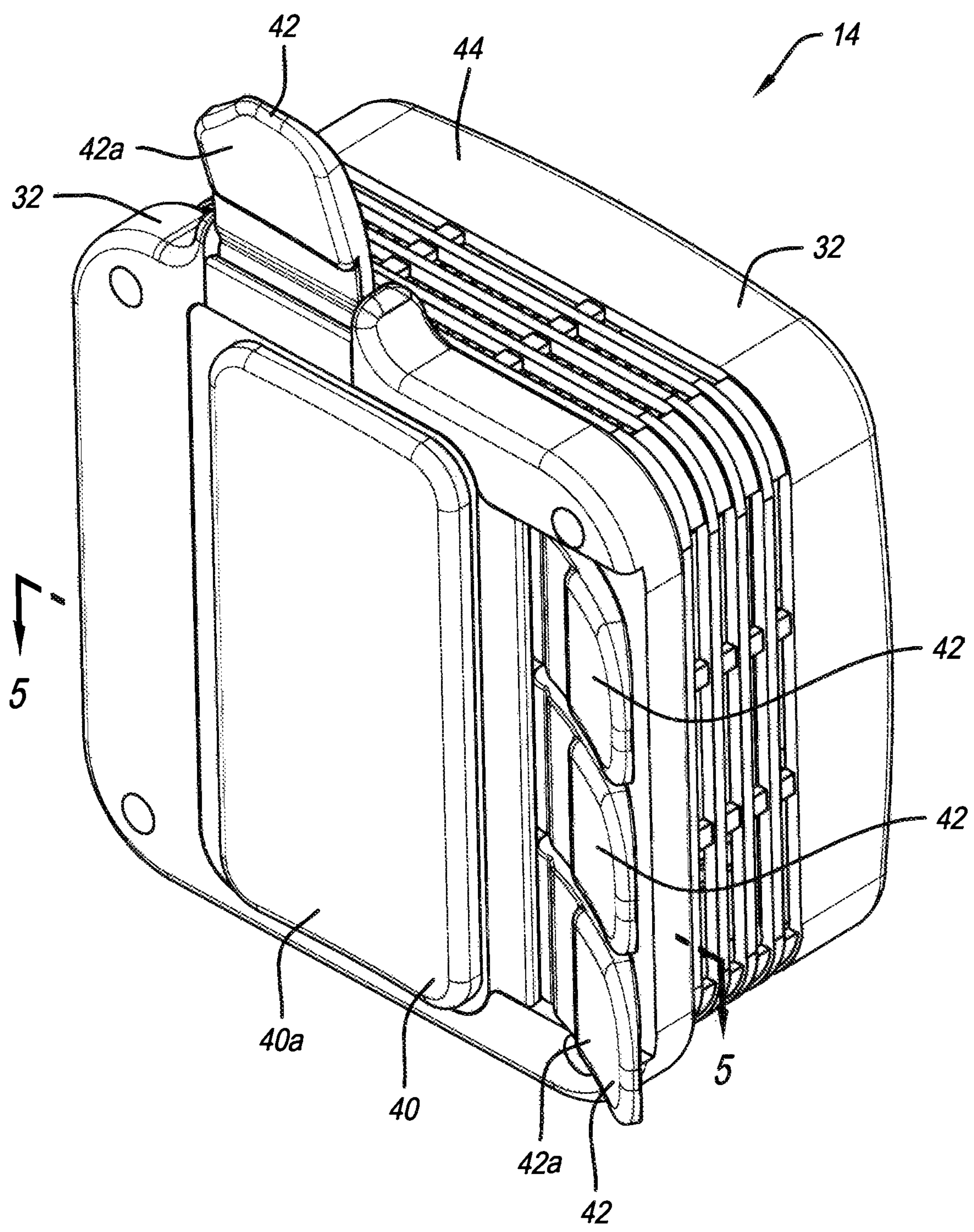
FIG. 4 is a perspective view of a temperature control module in accordance with an aspect of the present disclosure.
Figure 5:
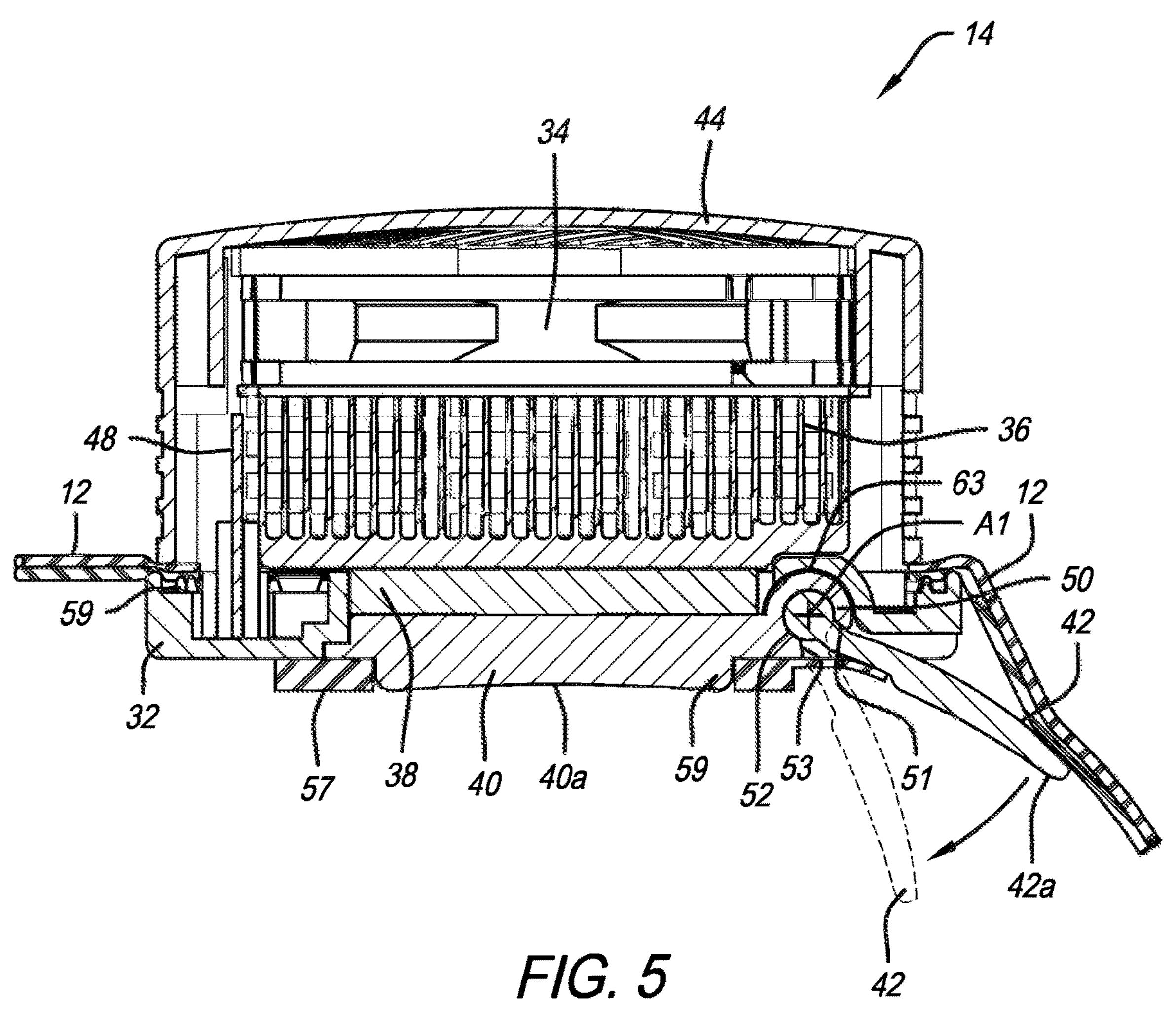
FIG. 5 is a cross-sectional view of the temperature control module.
Figure 6:
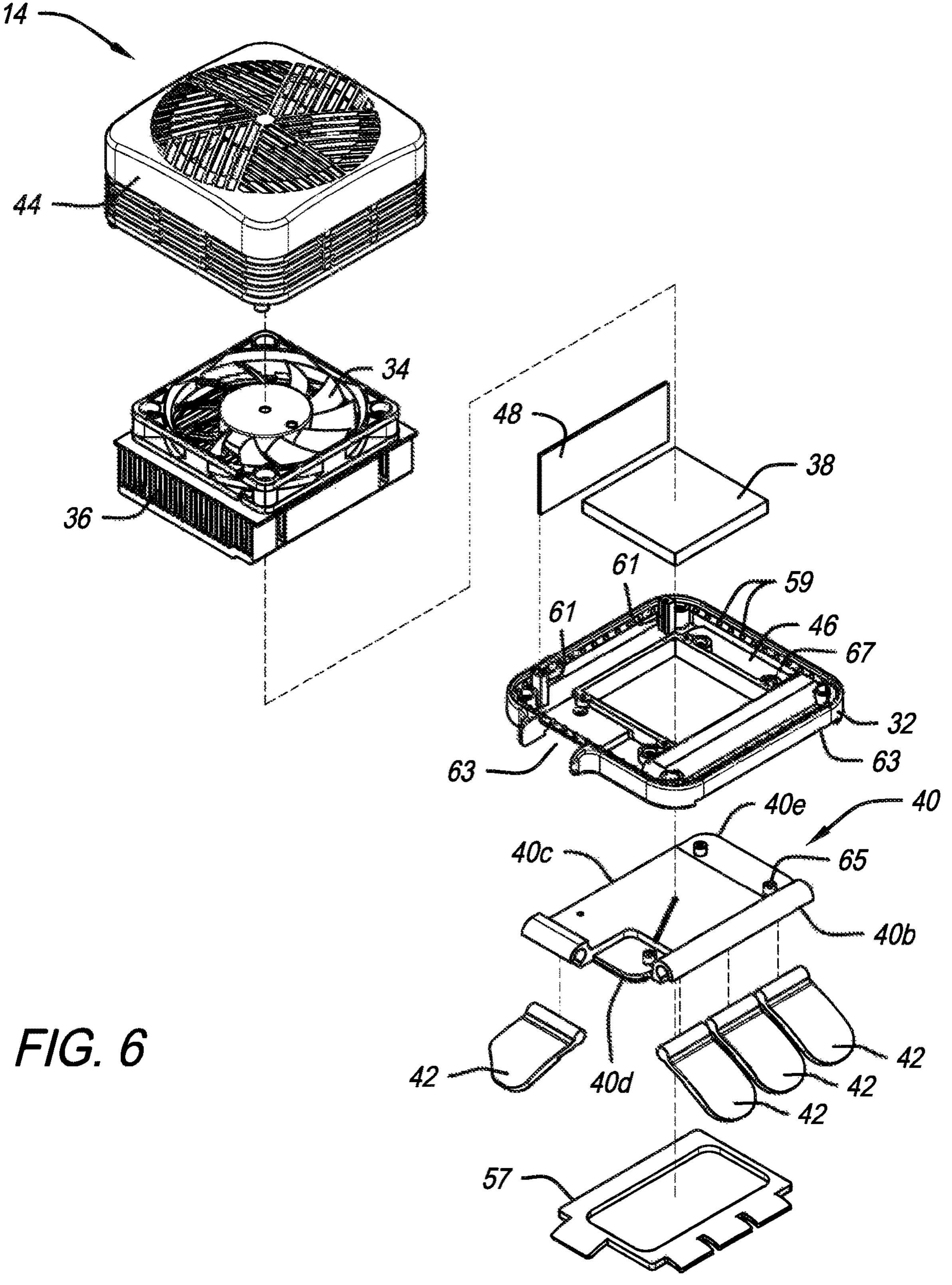
FIG. 6 is a an exploded perspective view of the temperature control module.

FIGS. 4-6 show a temperature control module 14. In a some embodiments, the temperature control module 14 includes a housing 32, a fan 34, a heat sink 36, a thermoelectric cooler, Peltier device or controllable temperature element 38, a spreader plate or member 40 and a plurality of finger spreaders 42 that are pivotably attached to the spreader member 40. In some embodiments, the housing 32 includes an upper portion 44 and a lower portion 46. In use, the lower surface 40 a of the spreader member 40 and the inner or lower surface 42*a* are positioned to contact and transfer thermal energy (hot or cold) to the user's body part. As discussed above and herein, the lower surface of the controllable temperature element 38 is configured to transfer thermal energy to the upper surface of the spreader member 40 and heat sink 36 is configured to pull heat from the upper surface of the controllable temperature element 38. The fan 34 helps dissipate heat from the heat sink 36 and other components. In use, the primary spreader member 40 is cooled or heated by the controllable temperature element 38 and the heat or cold is conducted from the primary spreader 40 to the finger spreaders 42. In some embodiments, the temperature control module 14 also includes a PCB 48 for electrical and data communication (with the main control module 18 or other controller) and controlling the module.

In some embodiments, the spreader member 40 is configured to conduct thermal energy to the finger spreaders 42. The spreader member 40 includes first and second opposing edges 40*b* and 40*c* and third and fourth opposing edges 40*d* and 40*e*. In some embodiments, finger spreaders 42 extend from and/or past a plurality of the outer edges of the spreader member. For example, as shown in FIG. 6, three finger spreaders 42 extend from the first edge 40 b and one finger spreader extends from the third edge 40*d*. In another embodiment, one or more finger spreaders can extend from all or three edges.

Any type of pivotable connection between the finger spreaders and the spreader member is within the scope of the present disclosure. In some embodiments, as shown in FIGS. 4 and 5, the finger spreaders 42 are hingedly attached to the spreader member 40. To provide the hinged connection, the spreader member 40 includes one or more knuckle portions 50 and the finger spreaders 42 include a pin portion 52 that is received in the knuckle portion 50. The contact portion 54 of the finger spreader 42 extends outside of knuckle portion 50 and the pin portion 52 is rotatable within the knuckle portion 50. FIG. 5 shows the finger spreader 42 in a first position in solid lines and a second position in dashed lines. In some embodiments, in at least the second position, a distal end 42*a* of the finger spreader(s) 42 is positioned below the lower surface 40 a of the spreader member 40.

Figure 9:
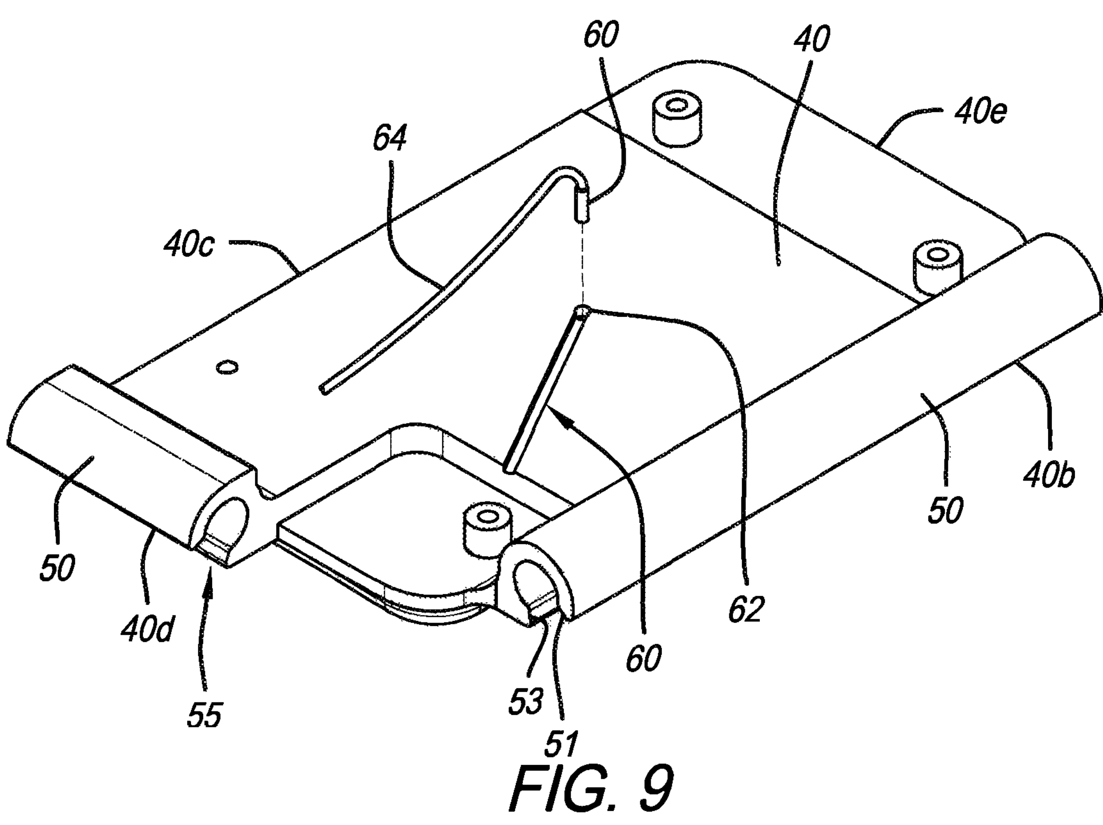
FIG. 9 is a perspective view of a spreader member with a thermistor exploded therefrom.

In some embodiments, the knuckle portion 50 includes upper and lower stop members 51 and 53 that include a pivot space 55 therebetween (see FIG. 9). The finger spreaders 42 are pivotable within the pivot space 55 and between the upper and lower stop members 51 and 53. The upper and lower stop members 51 and 53 define the upper and lower limits of the pivot angle of the finger spreaders. FIG. 5 shows the finger spreader 42 in the first position in solid lines and with the upper surface against the upper stop member 51 and in the second position in dashed lines with the lower surface against the lower stop member 53.

Figure 7:
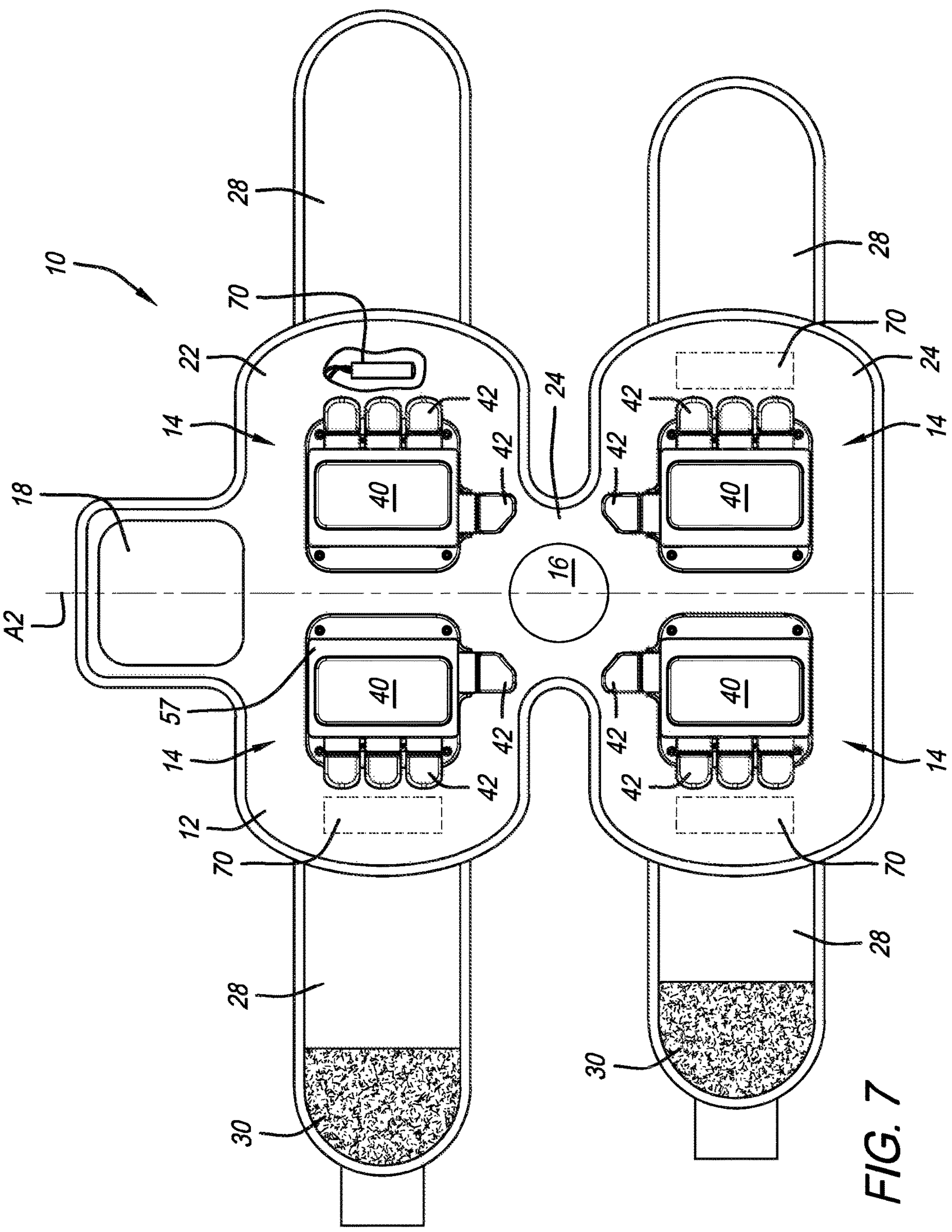
FIG. 7 is a rear elevational view of the temperature controllable wrap assembly of FIG. 1.

As shown in FIGS. 5 and 7, in some embodiments, the temperature control module 14 includes a pad member 57 that at least partially covers the spreader member 40 and allows the contact portion 59 of the spreader member 42 to extend there around (see FIG. 7). The pad member 57 can be included to improve comfort. For example, it can be made of a soft material, such as TPE rubber or other rubber and overmolded onto the plastic lower portion of the housing.

It will be appreciated that in wrap assemblies for different portions of the body, different numbers of finger spreaders can be used in different places or extending from different sides of the main spreader member 40 in order to accommodate different portions, parts or shapes of the human anatomy. For example, as shown in FIG. 7, each of the temperature control modules 14 include three finger spreaders 42 extending outwardly therefrom and in a generally circumferential direction around the user's leg when the wrap assembly 10 is secured to a user's leg (they adapt to and are secured against the user's quadricep and calf) and one finger spreader 42 extending upwardly or downwardly toward the user's knee cap, such that they surround the knee cap when the wrap assembly is secured to the user's leg. The separate finger spreaders 42 provide flexibility to adapt to different sized user's body parts and geometries. When the wrap portion 12 is wrapped around the user's leg, the lower or inner surface of the wrap portion 12 contacts the upper surface of the finger spreader 42 and pivots the finger spreader 42 into contact with the user's skin.

As shown in FIG. 5, in some embodiments, the wrap portion 12 is sandwiched between the upper portion 44 and the lower portion 46 of the housing 32. The lower portion 46 may include a plurality of spike members 59 that engage the wrap portion 12 and help hold the temperature control module 14 on the wrap portion 12. As shown in FIG. 6, the lower portion 46 also includes rails 61 that contain the ends of the PCB 48. The lower portion 46 also includes knuckle portion recesses 63 in which the knuckle portions 50 of the spreader member 40 is received. Registration members 65 may extend upwardly from the upper surface of the spreader member 40 and are received in registration openings 67 defined in the lower portion 46 of the housing 32.

Figure 8:
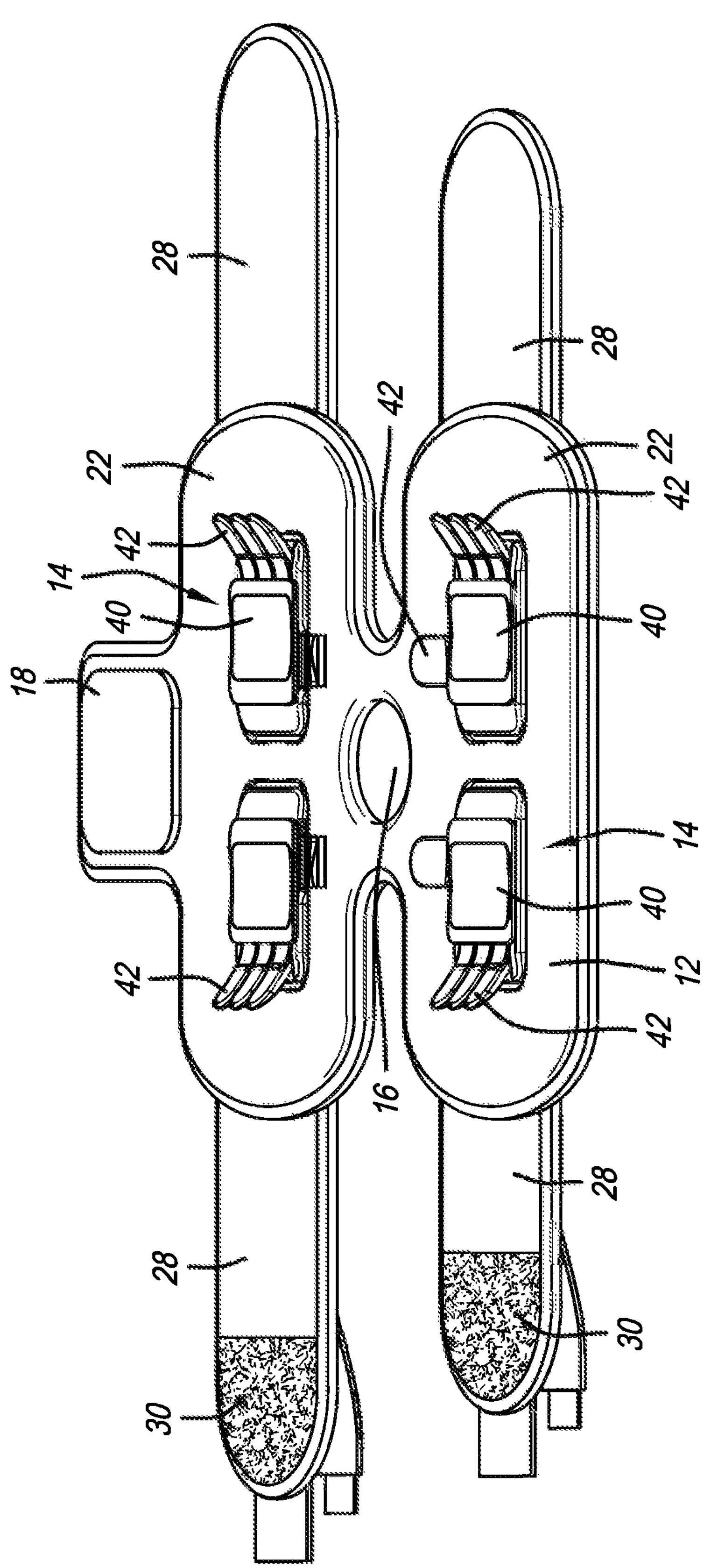
FIG. 8 is a rear perspective view of the temperature controllable wrap assembly of FIG. 1 in the open position.

As shown in FIGS. 7-8, the wrap assembly 10 includes temperature control modules 14 on opposite sides that include finger spreaders 42 extending outwardly in generally opposite directions (the three finger spreaders). It will be appreciated that because the finger spreaders are pivotable, they do not always extend or point in the same direction. Therefore, it should be understood by a person of ordinary skill in the art that, as shown in FIG. 7, three finger spreaders extend outwardly to the left and three finger spreaders extend outwardly to the right, but are not exactly 180° opposite to one another. And, anywhere within their range of pivotable motion, the three finger spreaders on the left still extend outwardly to the left and the three finger spreaders on the right still extend outwardly to the right. These arrangements meet the definition of generally outwardly and generally opposite from one another or in generally opposite directions. The finger spreaders 42 are each pivotable or movable along a pivot axis A1 (see FIG. 5) so that the bottom or contact surface of the finger spreader 42 is against the desired body part. It will be appreciated that in an embodiment with a plurality of finger spreaders 42, each of the finger spreaders 42 can individually be pivoted, moved or bent to provide further flexibility to make contact with a user's skin and to distribute the heat or cold.

As shown in FIGS. 7-8, in some embodiments, the wrap assembly 10 also includes a plurality of vibration motors or devices 70 disposed in or on the wrap portion 12 and or the strap portions 28. FIGS. 7-8 show the vibration devices 70 in hidden lines, with one vibration device 70 in FIG. 7 exploded out therefrom to show an exemplary type of vibration device used therein. In some embodiments, the vibration devices are located outside of the temperature control modules 14. In other words, the wrap portion 12 comprises a center axis A2 that extends between the temperature control modules 14 on either side. The temperature control modules 14 on the left are positioned between the vibration device(s) 70 on the left and the center axis and the temperature control modules 14 on the right are positioned between the vibration device(s) 70 on the right and the center axis.

Figure 10:
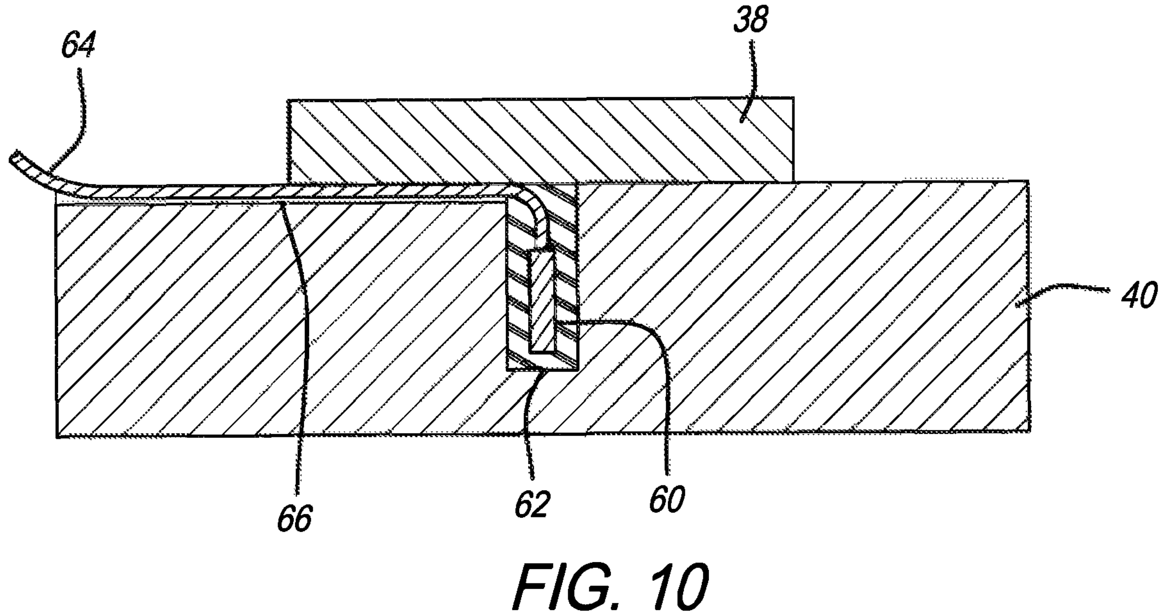
FIG. 10 is a cross-sectional view of the spreader member and thermistor.

As shown in FIGS. 9-10, in some embodiments, a thermistor 60 or other temperature measurement device or sensor is positioned or embedded underneath the controllable temperature element 38 and optionally adjacent to the center of the controllable temperature element 38. FIG. 9 shows the thermistor 60 exploded from a thermistor opening 62 defined in the controllable temperature element 38. The thermistor 38 is in communication with the control system/main control module 18 (see wire 64, which extends through groove 66 defined in the upper surface of the spreader member 40) and contributes to the control of the temperature of the spreader member 40 and the temperature of the lower surface 40 a that is against the user's skin. Positioning the thermistor 38 at or near the center of the spreader member 40 and/or controllable temperature element 38 allows monitoring of the hottest and coldest points at all times, thus increasing the accuracy of the control system and avoiding the spreader member 40 from becoming too hot or too cold and causing damage to the skin. FIG. 10 shows the thermistor 38 embedded in a material (epoxy, glue or other material) in thermistor opening 62.

As shown in FIGS. 1-3, the main control module 18 includes a plurality of buttons/switches 56 for controlling the wrap assembly 10. The main control module 18 is in electrical communication with the temperature control modules 14. In the exemplary embodiment shown in FIG. 1, the main control module 18 includes four buttons for controlling, from left to right, vibration, heat, cold and on/off. Shown below the vibration, heat and cold buttons are three LED lights for each. These represent different levels of vibration, heat and cold intensity when the buttons are pushed multiple times. In some embodiments, the main control module 18 includes a removable battery module 58, as shown exploded outwardly in FIG. 3. The battery module 58 can be pushed from one side (the opposite side in FIG. 3, as shown in FIG. 1) so that the battery module 144 slides out of the battery opening 58 a defined in the main control module 18. The battery module 58 or main control module can include lights (e.g., LEDs) thereon that show the amount of charge remaining in the battery. In some embodiments, the battery module 144 is magnetically secured within the battery opening 58 a in the main control module and pushing the battery module with a predetermined amount of force overcomes the magnetic force so remove the battery module from the main control module.

In some embodiments, the wrap assembly 10 includes a donut or ring member 72 positioned around the central opening 16. The ring member 16 may be embedded in the wrap portion 12 and may help align the wrap assembly on the user's knee cap when worn.

Figure 11:
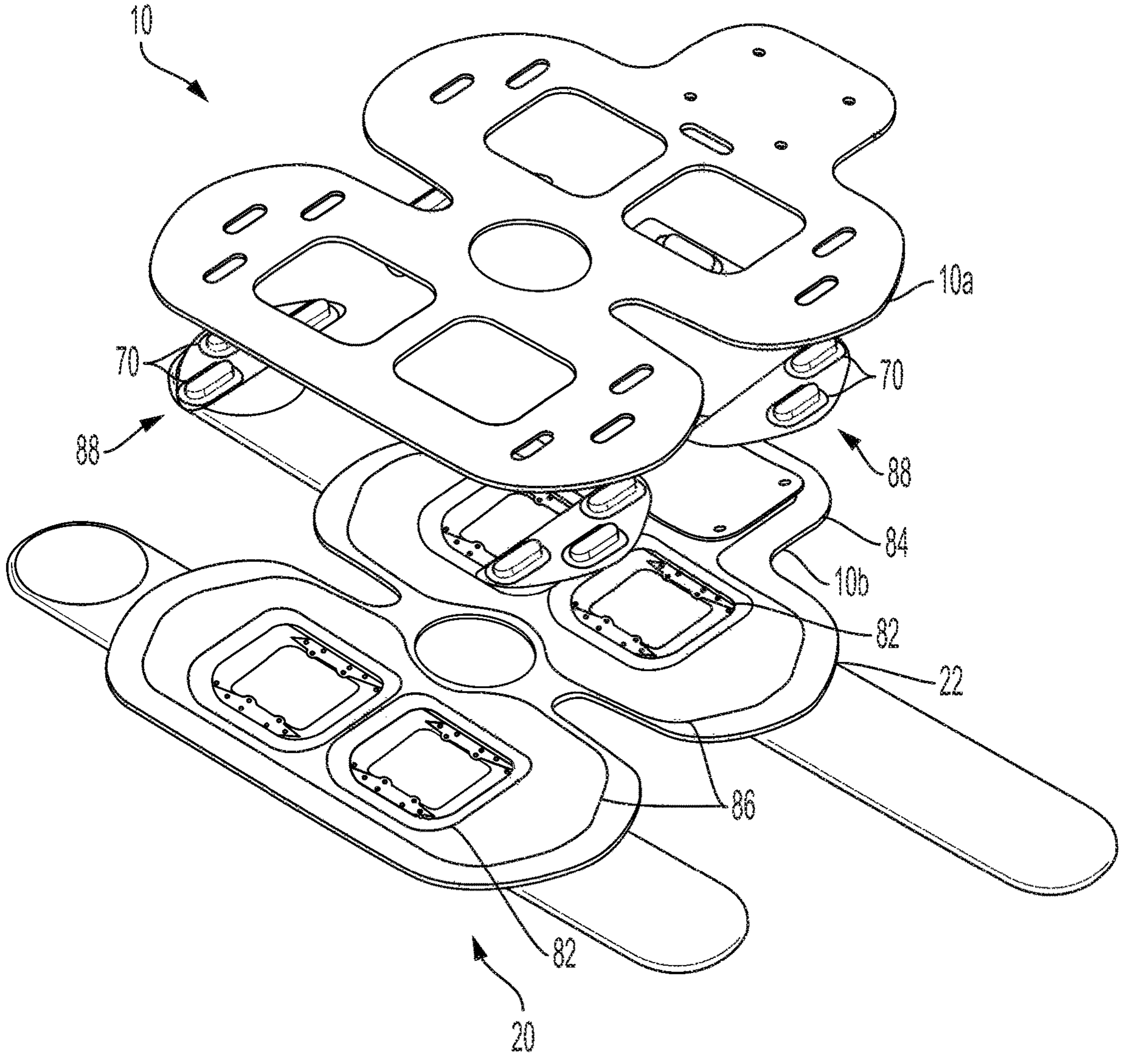
FIG. 11 is an exploded view of the temperature controllable wrap assembly of FIG. 1.
Figure 12:
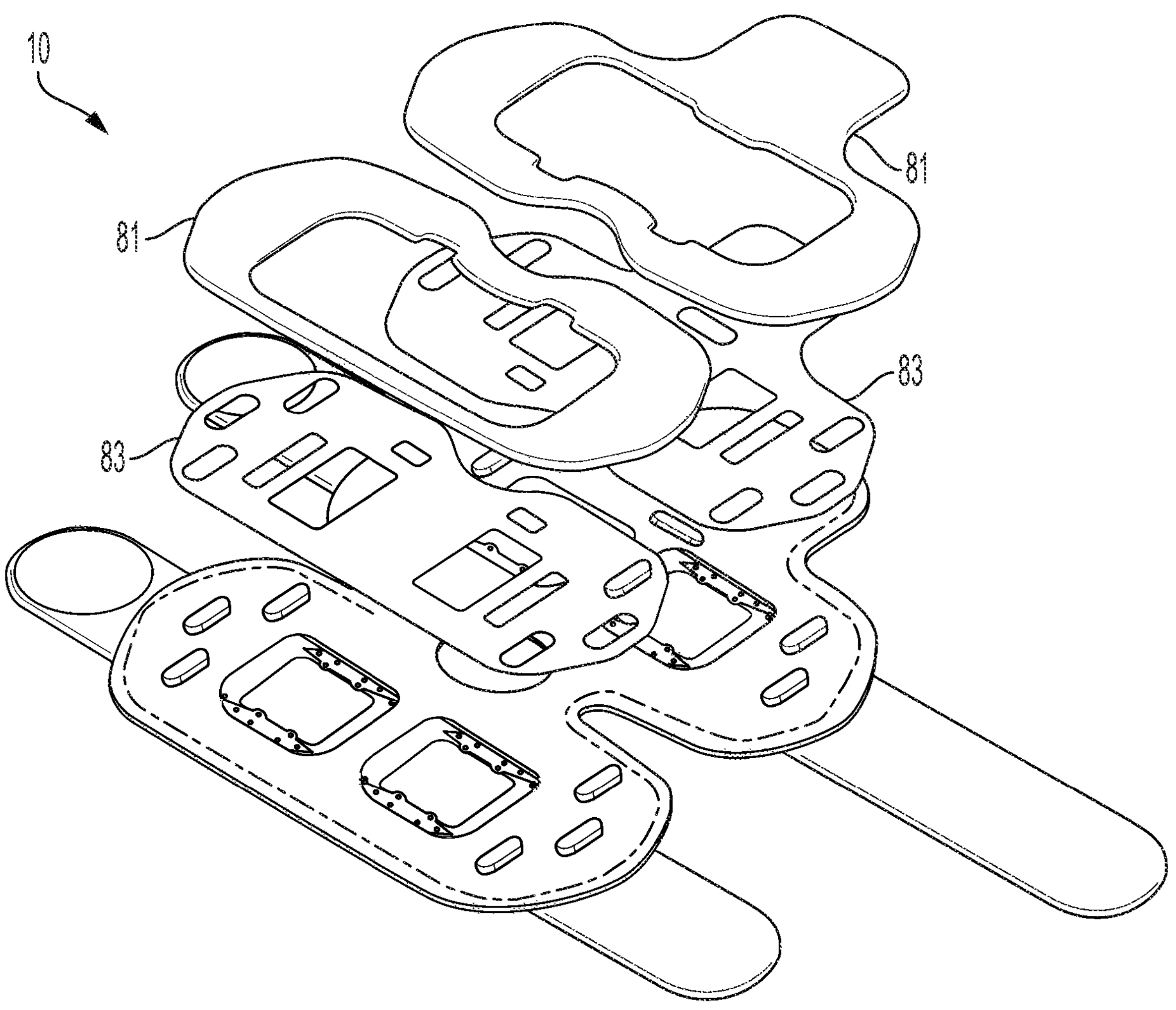
FIG. 12 is an exploded view of a cushion attachment and the temperature controllable wrap assembly of claim 1.

FIGS. 11 and 12 show optional constructional details of the temperature controllable wrap assembly 10 described above. FIG. 11 shows mounting skirts 82 and a mounting member 84 for mounting or otherwise attaching the temperature control modules 14 and control module 18, respectively, to the upper and lower strap portions 22, 20. For example, the mounting skirts 82 and mounting member 84 may be sewn to the upper and lower strap portions 22, 20, and may mechanically engage the temperature control modules 14 and control module 18 to retain the modules to the assembly 10. FIG. 11 also shows stiffener members 86 that are positioned between the mounting skirts 82 and mounting member 84 and the upper and lower strap portions 22, 20 to aid with securement. FIG. 11 also shows that the vibration motors 70 may all be included in vibration modules that each include a mounting panel 88 and one or more of the vibration motors 70 mounted on the mounting panel 88. The strap assembly 10 includes an inner strap layer 10*a* and outer strap layer 10*b* between which the vibration modules, a majority of each mounting skirt 82, and a majority of the mounting member 84 is located.

FIG. 12 shows cushion members 81 that may be attached to an inner, or wearer-facing, side of the strap assembly 10. The cushion members 81 may optionally be provided with stiffener members 83 to be disposed between the cushion members 81 and the strap assembly 10. The cushion members 81 and, if present, the stiffener members 83 may be removably attachable to the strap assembly 10 by any suitable mechanism, such as, for example, hook and loop fastening, snapping buttons, or magnets.

Figure 13:
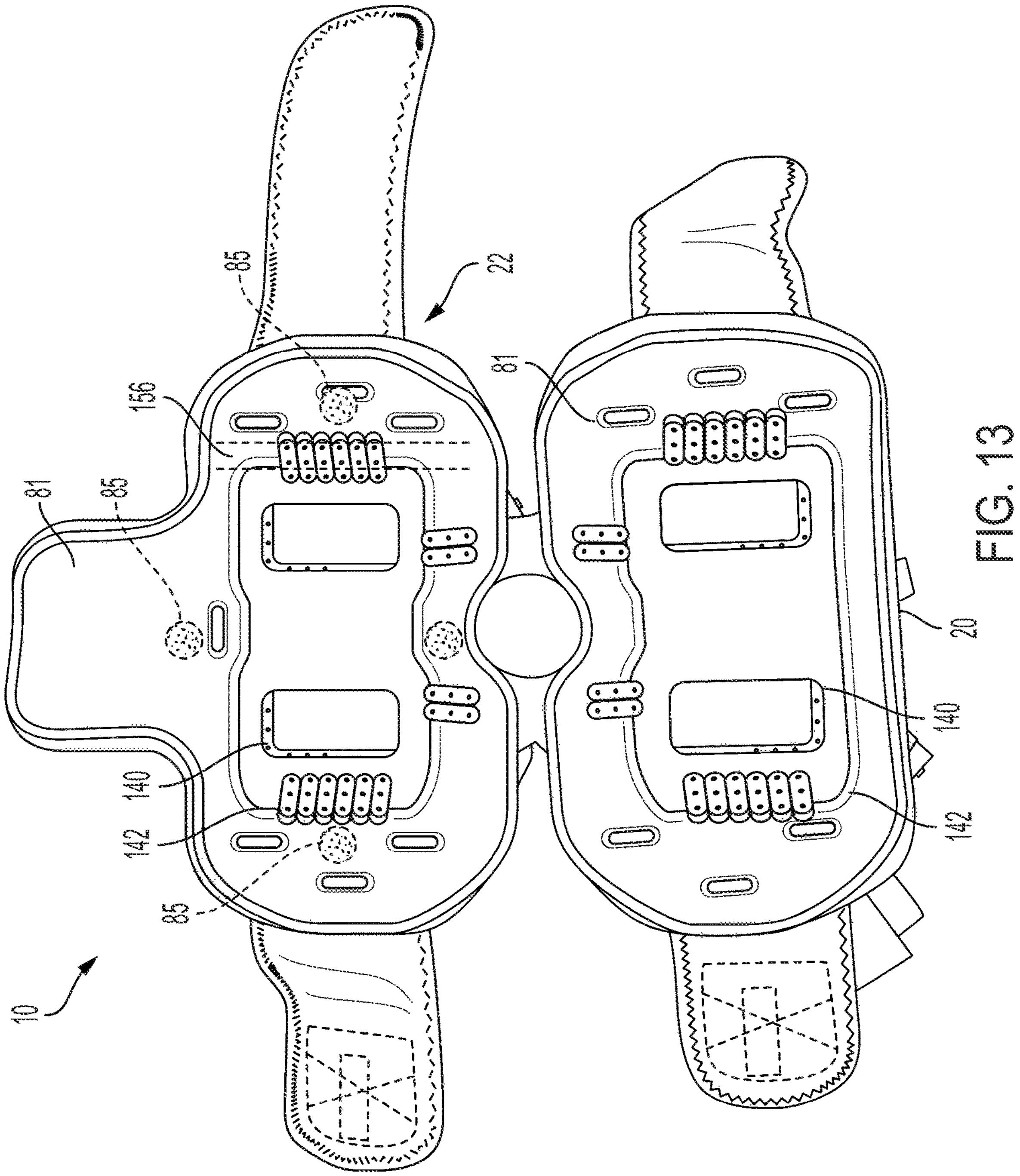
FIG. 13 is a plan view of the temperature controllable wrap assembly of FIG. 1 with a cushion attached thereto.

FIG. 13 shows the strap assembly 10 with the one or more pillow or cushion members 81 attached thereto, which provide comfort for the user and may also be removable so that they can be washed or replaced. The cushion members 81 may include magnets 85 (shown as four dots) or other attachment mechanism (Velcro, snaps, buttons, etc.) so that the cushion members can be secured or removably attached to the strap portion 88. Upper and lower or first and second cushion portions can be included for the upper and lower portions 22 and 20 of the strap assembly 10. The cushion members provide a layer generally parallel to the thermal spreader surface that improves comfort and may be a layer that is sacrificed or replaced due to the buildup of sweat and moisture over time. Any soft material, such as foam or fabric padding, is within the scope of the disclosure. In some embodiments, the cushion member includes a memory foam layer wrapped in a fabric enclosure. The magnets may be embedded in the memory foam or between layers (and a complementary magnet is included in the corresponding strap portion 20 or 22). The thickness is selected to provide comfort while allowing the vibration from the vibration motors to reach the user's skin. The cushion or strap may optionally contain a tunnel for a secondary strap 456 for pressing the temperature control module against the skin, as will be detailed further below.

FIG. 13 also shows the strap assembly 10 having temperature control modules with twice as many finger spreaders 142 as the temperature control modules 14 in the previous examples installed therein. Specifically, the temperature control modules of FIG. 13 each have four sides, with six finger spreaders 142 extending from one of the four sides and two finger spreaders 142 extending from an adjacent one of the four sides. The temperature control modules of FIG. 13 are otherwise alike to the temperature control modules 14 describe above in all respects.

Figure 14:
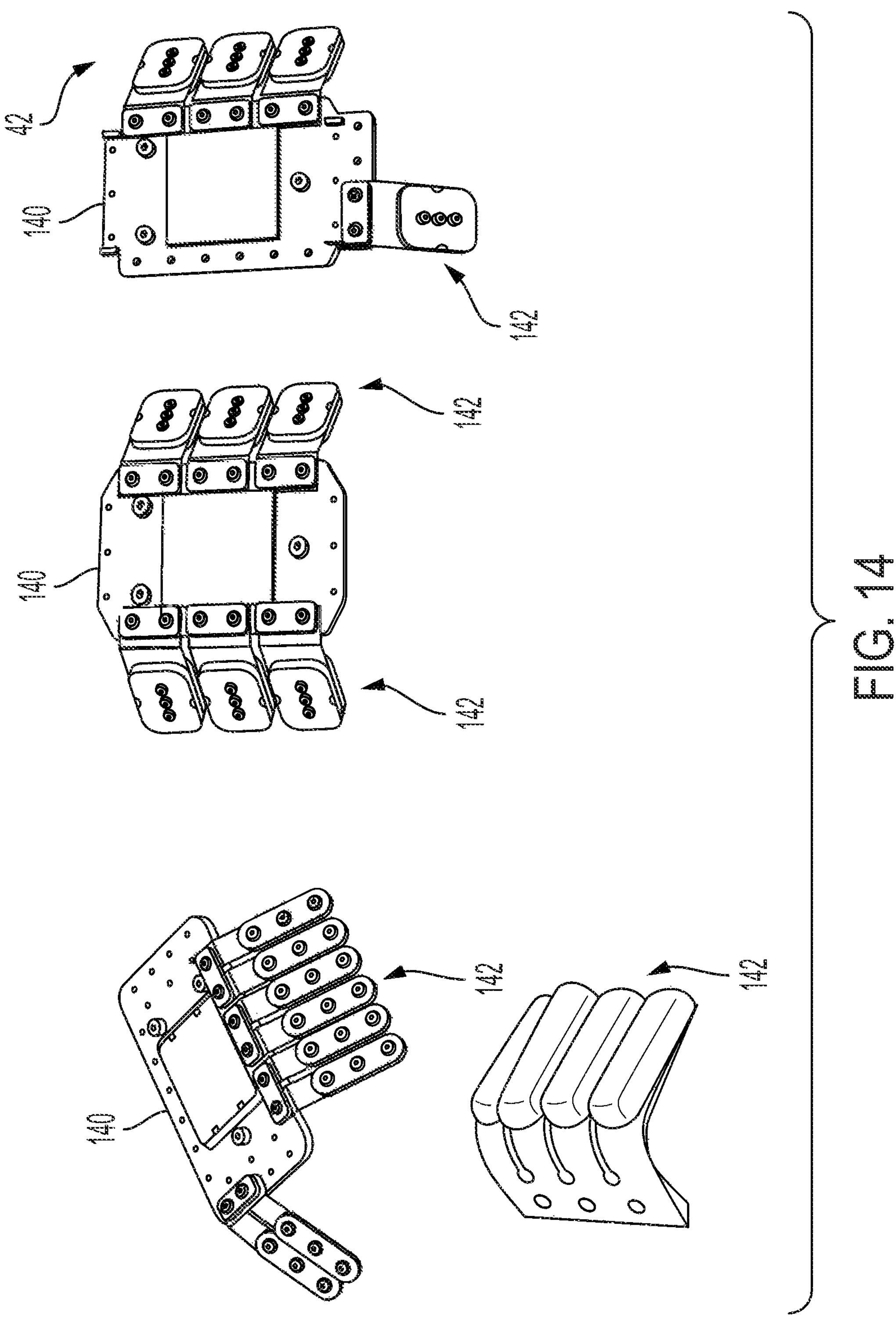
FIG. 14 illustrates a variety of contact spreaders usable with the temperature control module of FIG. 4.

Spreader arrangements according to a wide variety of other configurations are equally suitable for use with the temperature control modules of any of the foregoing examples. Thus, the strap assembly 10 described above may be used with temperature control modules having any of the spreader arrangements, which may also be referred to as contacts or contact portions, disclosed herein. Similarly, any other assemblies or garments shown herein to be usable with any particular temperature control module may be used with temperature control modules having any of the contacts or spreader arrangements disclosed elsewhere herein. FIG. 14 shows several varieties of contacts or contact portions usable with the temperature control modules 14 described above in place of the specific spreader member 40 shown in the foregoing examples. Each such contact or contact portion includes a main spreader 140 and finger spreaders 142 that extend from the main spreader 140. Different numbers of spreaders 142 of varying widths and lengths can be used in different places or extending from different sides of the main spreader 140 in order to accommodate different portions, parts or shapes of the human anatomy. For example, as shown in FIG. 13, each of the temperature control modules 14 include six finger spreaders 42 extending outwardly therefrom and in a generally circumferential direction when the strap assembly is secured to a user's leg and two finger spreaders 42 (they adapt to and are secured against the user's quadricep and calf) extending upwardly or downwardly toward the user's knee cap, such that they surround the knee cap when the strap assembly is secured to the user's leg. The separate finger spreaders provide flexibility to adapt to different sized user's body parts and geometries. The finger spreaders 142 are biased to the position shown in FIGS. 13-19 either by their own inherent resilience or by a spring or other external biasing element.

Figure 15:
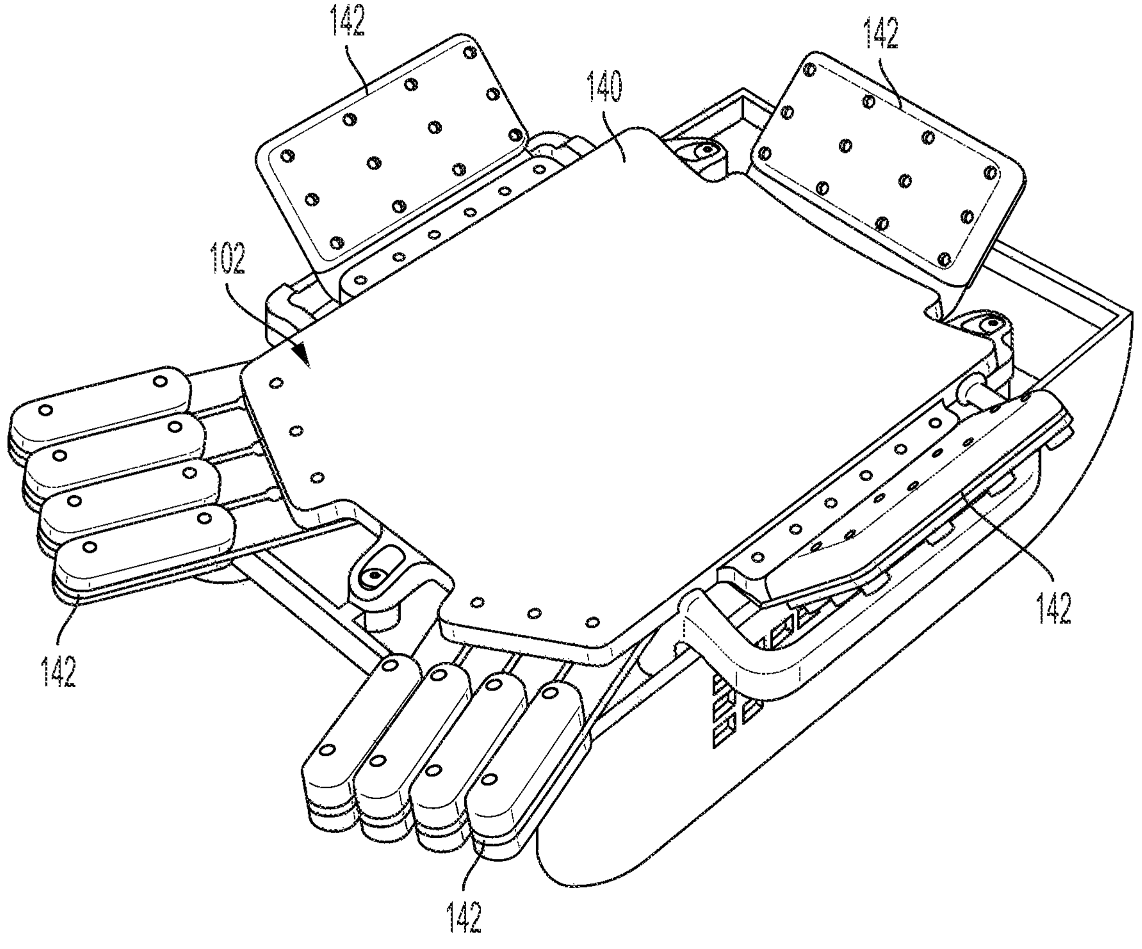
FIG. 15 is an oblique perspective view of a contact side of a temperature control module according to another arrangement.

FIG. 15 shows a bottom view of a temperature control module with a curved main spreader 140, three wide finger spreaders 142, and groups of four narrow finger spreaders 142. The four smaller finger spreaders 142 in each group can each individually be pivoted or bent to provide further flexibility to make contact with a user's skin and to distribute the heat or cold.

Figures 16, 17:
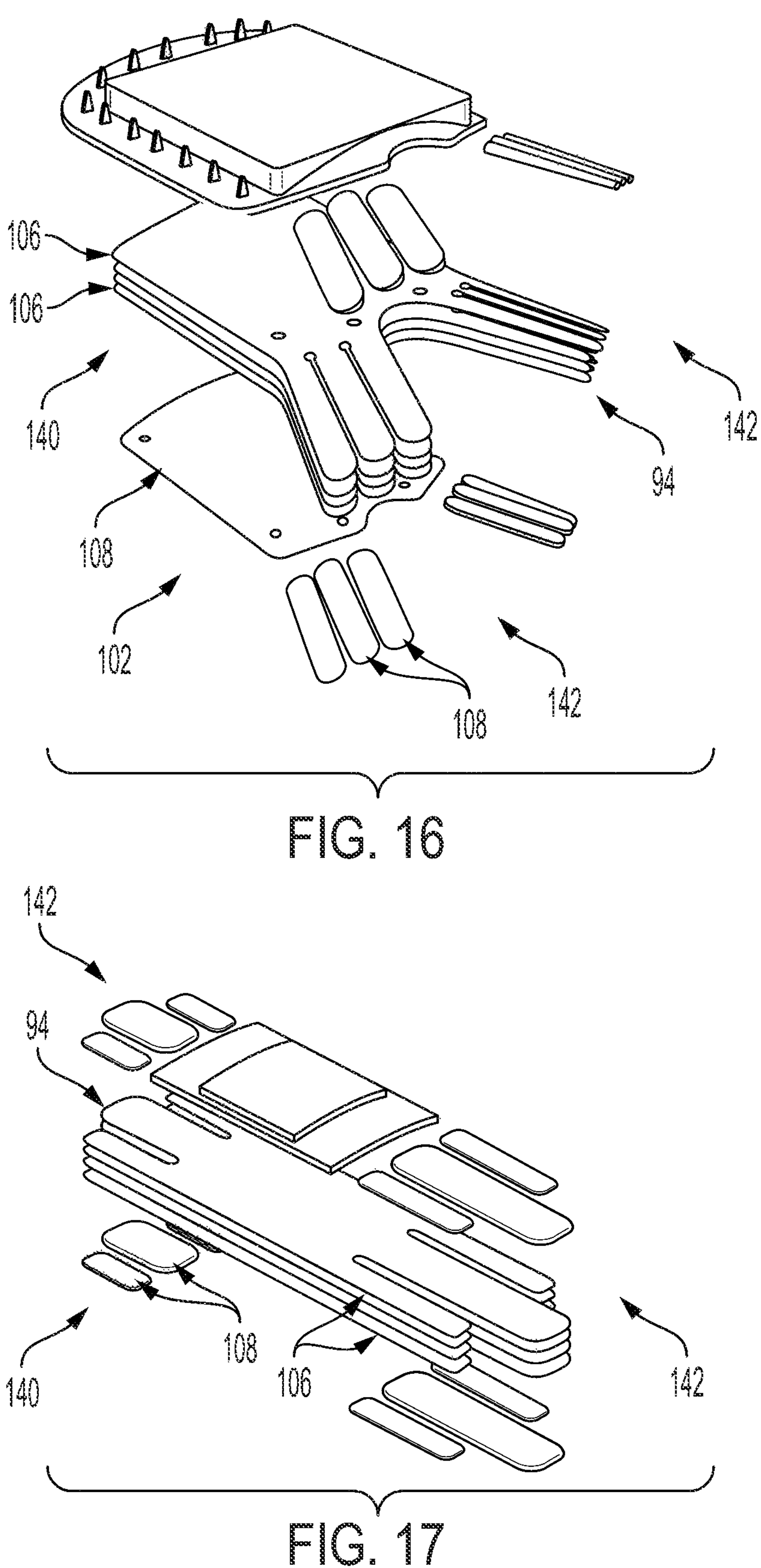
FIGS. 16-18 are exploded views of contact spreaders usable with the temperature control modules of FIGS. 4 and 15.
Figure 18:
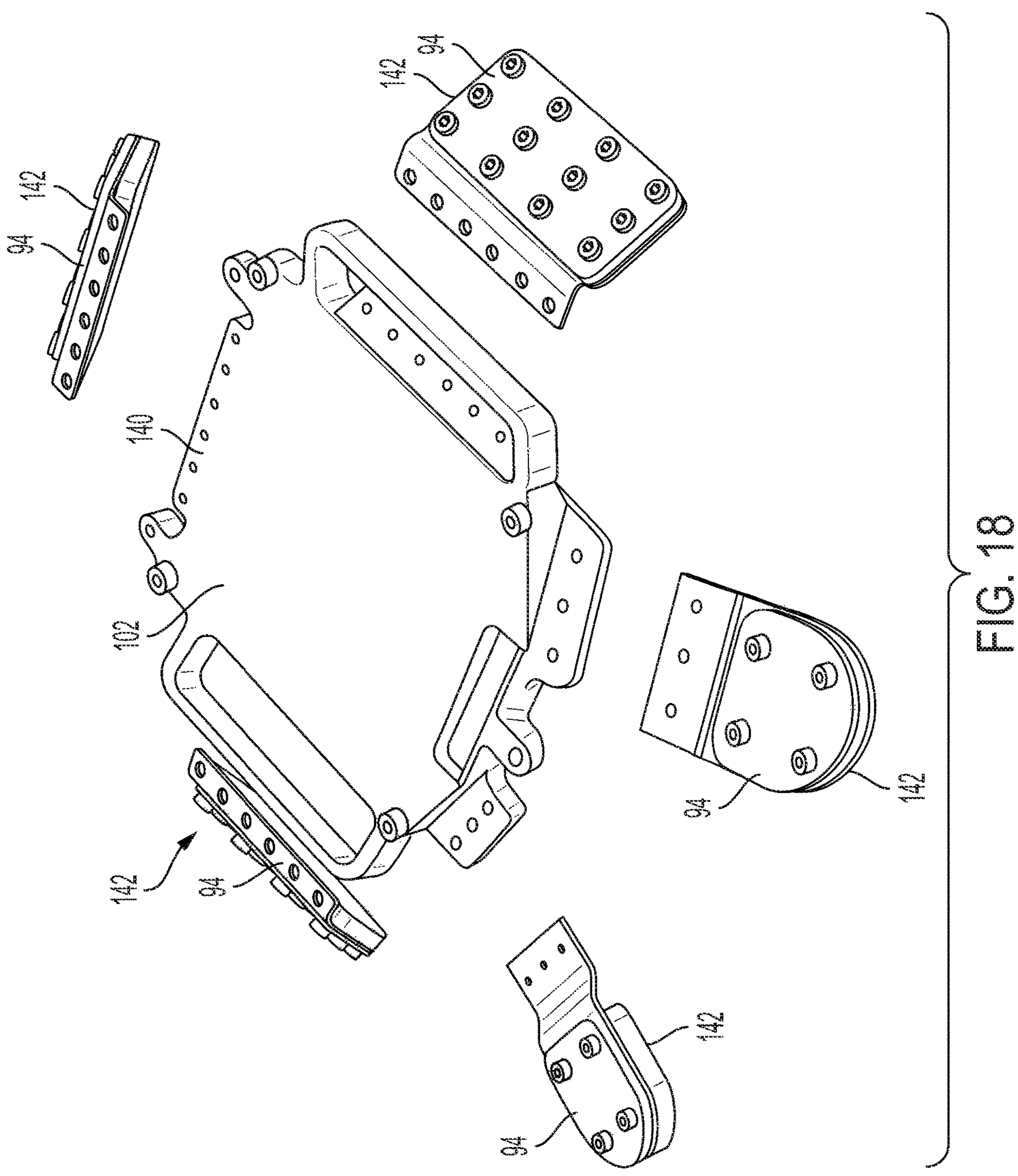

FIGS. 16-18 show exploded views of other examples of contacts that can be used with temperature control modules 14. In these embodiments, thin copper layers 106 (e.g., die cut layers) are stacked on one another and form the separate main spreader 140 and finger spreaders 142 discussed above. The finger spreaders 142 can be pivotable with respect to the main spreader 140 or they may not be. Therefore by creating the thin layers 106, the desired shape (depending on the body part targeted) can be created. The stack of layers can include layers of aluminum or thicker copper 108 above and below in the areas were rigidity needs to be increased. Also, the copper layers can be formed in different shapes to adapt exactly to the geometry of the muscle(s) to be treated. Moreover, the number of layers and the materials of the layers are merely examples, and either or both may be varied in other arrangements.

FIG. 16 shows a contact shaped similarly to that shown in FIG. 15 above, but with a different number of finger spreaders 142. Specifically, the contact of FIG. 16 includes only two groups of three finger spreaders 142, which the finger spreaders in each group extending parallel to one another and at an acute angle relative to the finger spreaders in the other group. The contact of FIG. 16 is particularly suitable for being used on the calf muscle or in the strap assembly 150 described below. FIG. 17 shows a contact that can be used on a hamstring.

Figure 19:
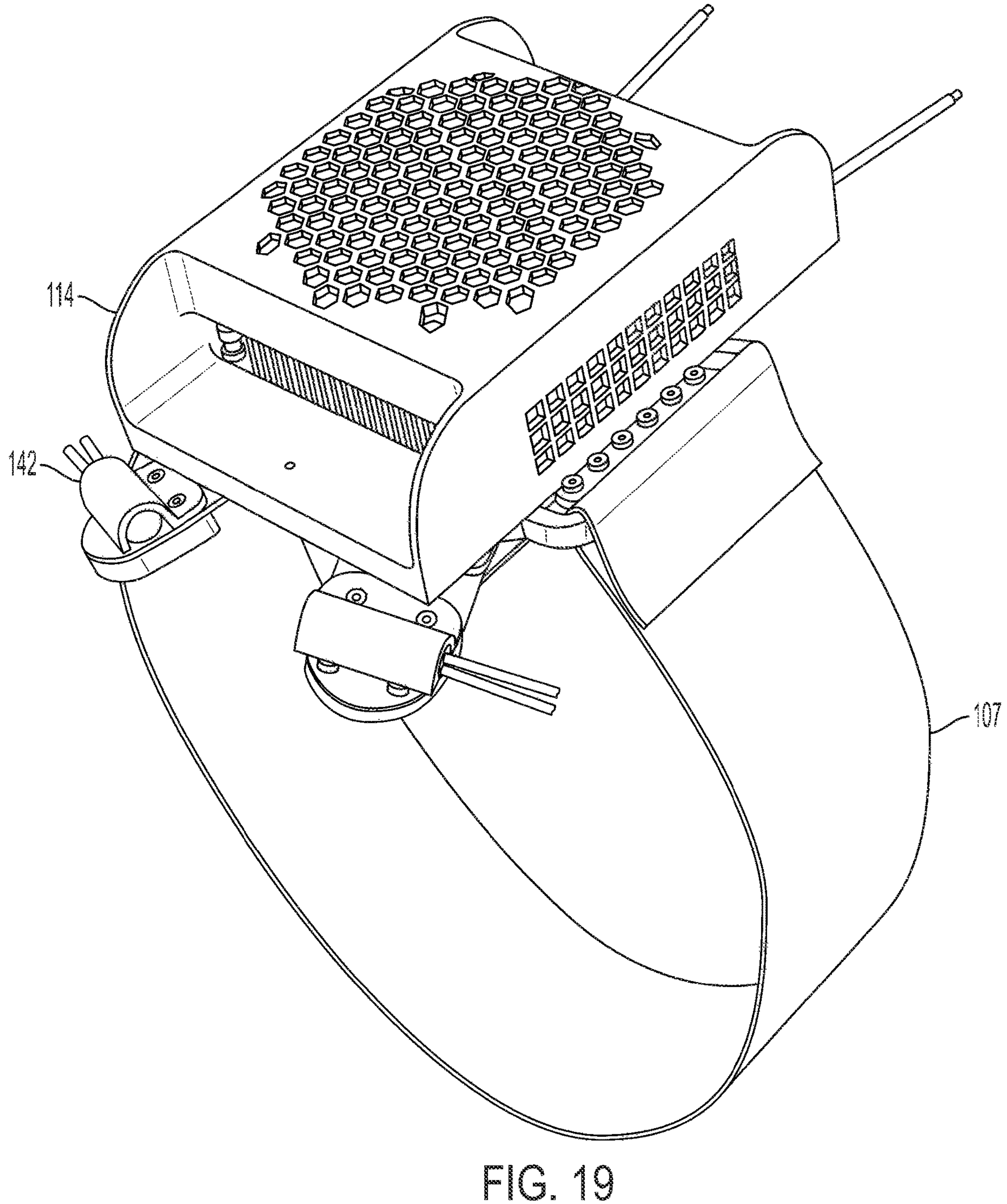
FIG. 19 is an oblique perspective view of a temperature control module according to another arrangement with an elastic band connected thereto.
Figure 20:
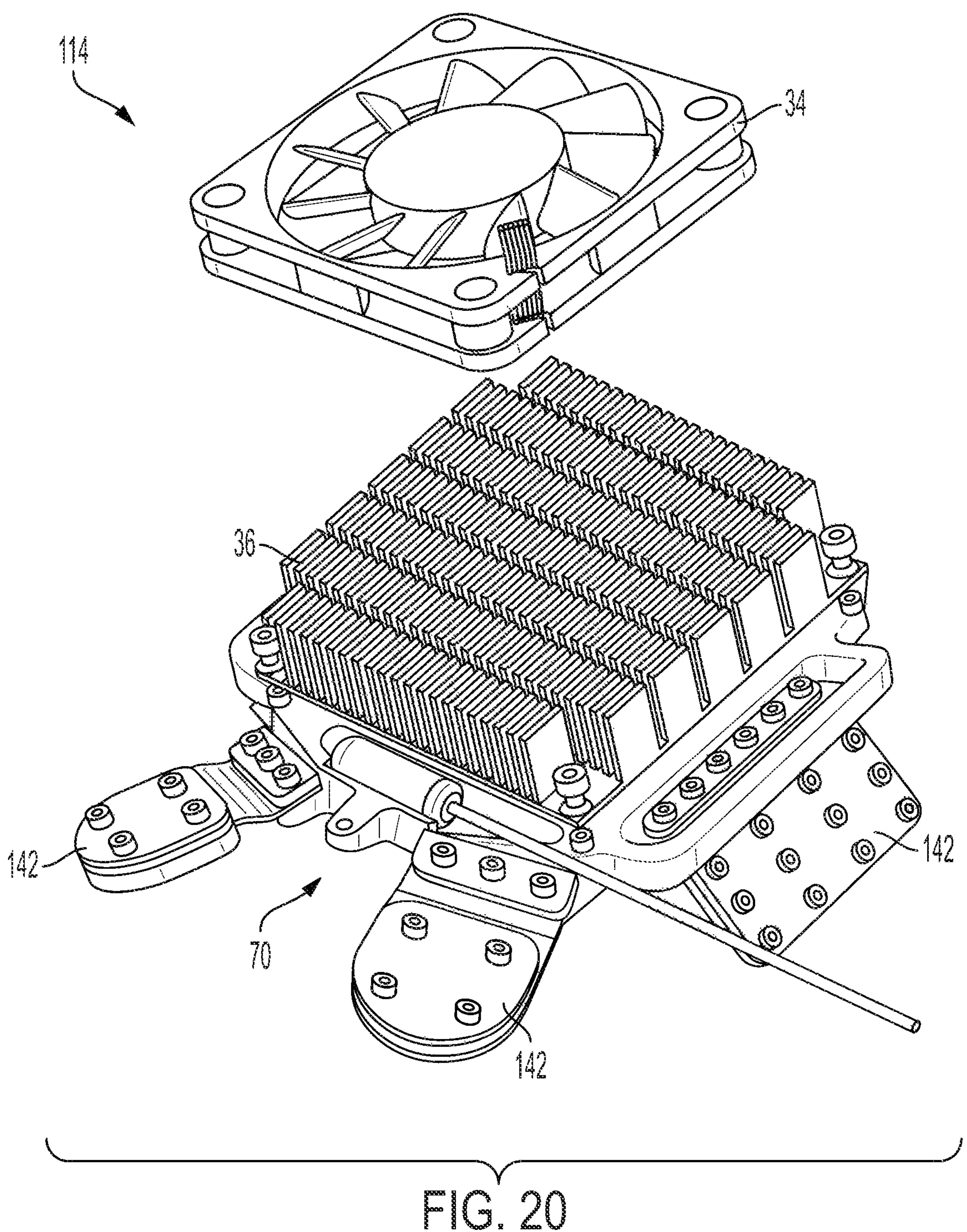
FIG. 20 is an exploded view of the temperature control module of FIG. 19.

FIGS. 19 and 20 show a temperature control module 114 with an elastic band 107 mounted thereto. Temperature control module 114 is alike to temperature control module 14 in all respects except those explicitly stated or illustrated herein, and may therefore include a Peltier device or other thermal element, heat sink 36, and fan 34 such as those described above with regard to the temperature control module 14 of previous examples. The temperature control module 114 therefore includes a contact that itself includes a main spreader 140 and movable or bendable finger spreaders 140. FIG. 20 shows the temperature control module 114 partially exploded and without a housing, showing that the temperature control module 114 includes at least one vibration motor 70 on the main spreader 140. A Peltier device is positioned on the main spreader 140 so that the contact can conduct heat or cold to the user. In use, the primary spreader 140 is cooled or heated by the Peltier device and the heat or cold is conducted from the main spreader 140 to the finger spreaders 142. Vibration motors 70 can alternatively or additionally be included in the strap 107, a garment portion, within the housing of the temperature control module 114, or on the spreaders 140 or 142. As with the contacts according to other examples herein, the spreaders, spreader members, legs or extension members can be made of aluminum or another metal and the pivot points or the like of the spreaders can be made of copper or other metal.

The attachment of an elastic band 107 allows the temperature control module 114 to be easily worn on any limb. Moreover, because the strap 107 is adaptable to many shapes, the temperature control module 114 can be easily repositioned about the limb to enable hot or cold treatment of specific points. The elastic band 107 can be used with temperature control modules lacking onboard vibration motors 70 such as the one present in the illustrated example, but the addition of a vibration motor 70 to the temperature control module attached to the band 107 allows the user to combine thermal and vibration treatment easily and precisely to any limb.

The contact of a temperature control module 14, 114 of any of the foregoing examples, including main spreader 40, 140 and finger spreaders 42, 142, can be enclosed or sewn into garment portion. The fabric or strap may be on top of the spreader, thereby allowing the bottom surface of the spreader to touch the skin of the user. In this embodiment, when the strap or garment portion is wrapped around the body part (e.g., leg), the finger spreaders 142 will be moved or pivoted by the fabric to help the spreaders move closer to or against the leg. The user can also push the spreaders through the fabric to help the spreader to the desired position.

Described herein and shown in FIGS. 21-24 is a garment assembly 210 that includes vibration therapy integrated therein. FIGS. 21-24 show the garment assembly embodied in a sleeve. However, it will be appreciated that this is not a limitation on the present disclosure and the garment assembly 210 can be any type of wearable garment.

Figure 21:
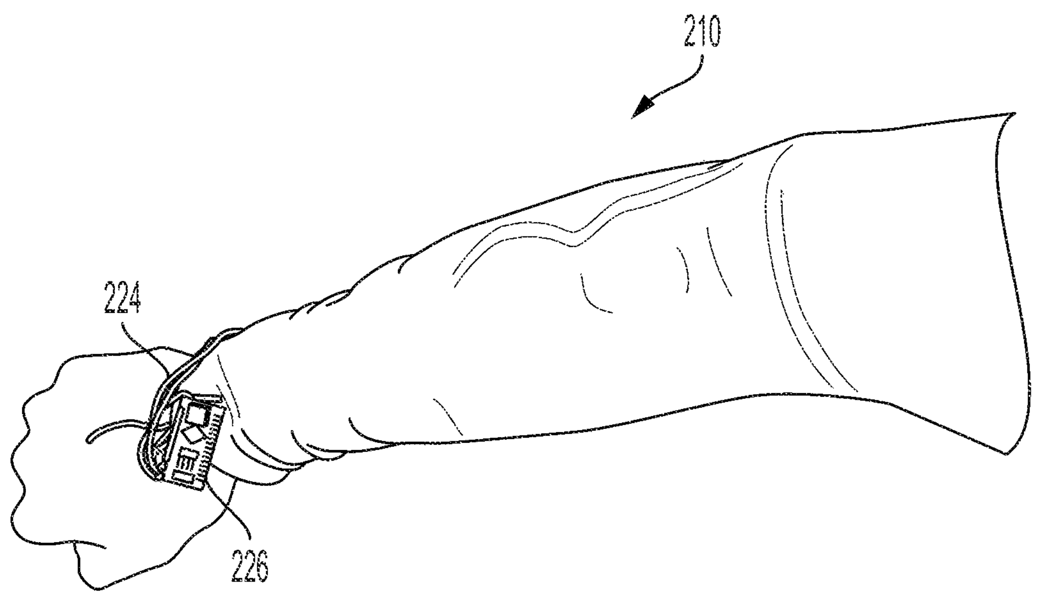
FIG. 21 illustrates an arm wearing a therapeutic garment according to another aspect of the disclosure.
Figure 22:
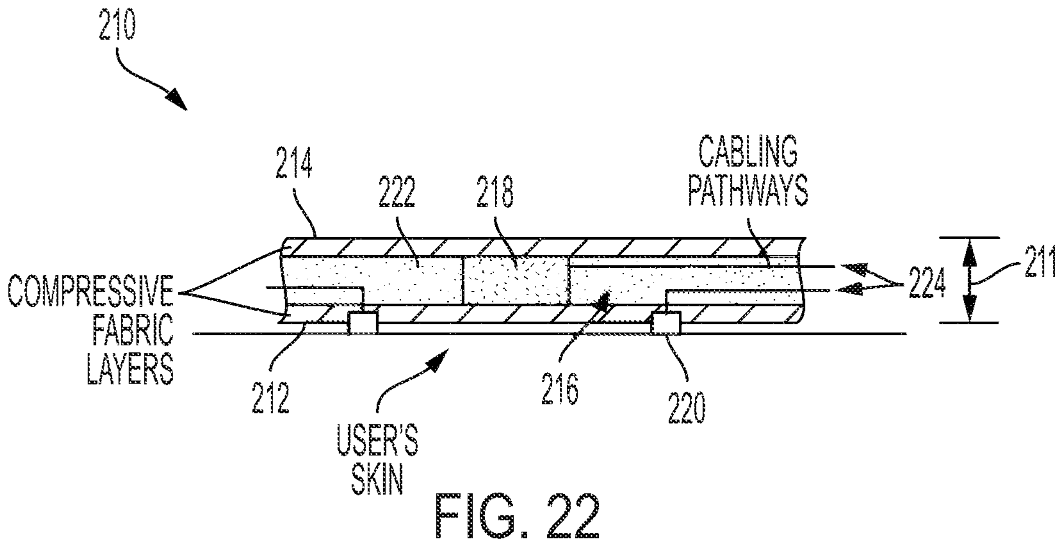
FIG. 22 is a cross-sectional view of a portion of the garment of FIG. 21.

FIG. 21 shows an example of the garment assembly 210. As shown in FIG. 22, in some embodiments, the garment assembly 210 includes an inner fabric layer 212, an outer fabric layer 214 and a vibration layer 216 that includes a plurality of vibration devices 218. The inner and outer fabric layers 212 and 214 sandwich the vibration layer 16 and the vibration devices 218 therebetween. The vibration devices 218 and related components can be housed in a housing (flexible or hard) or secured on a bracket, PCB, or layer. As shown in FIG. 22, a thickness 211 of the garment assembly 210 is defined as the distance between an inner side of the inner layer 212 and an outer side of the outer layer 214.

Figure 23:
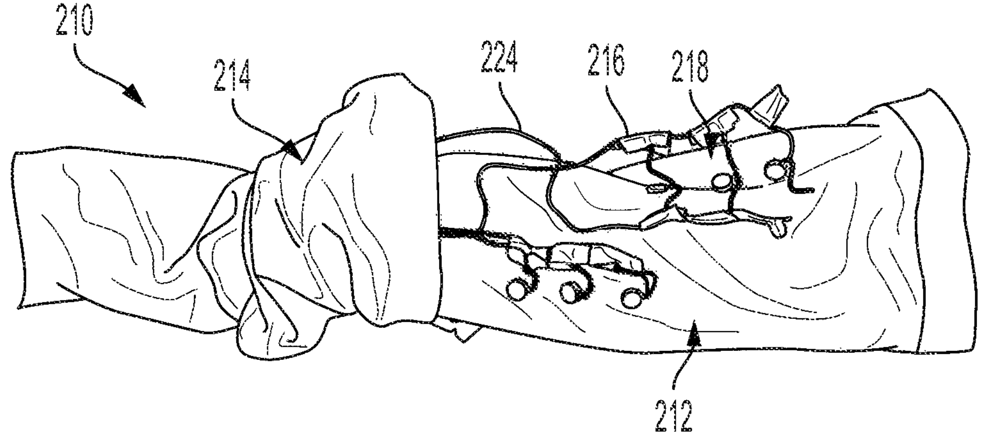
FIG. 23 is a plan view of the garment of FIG. 21.
Figure 24:
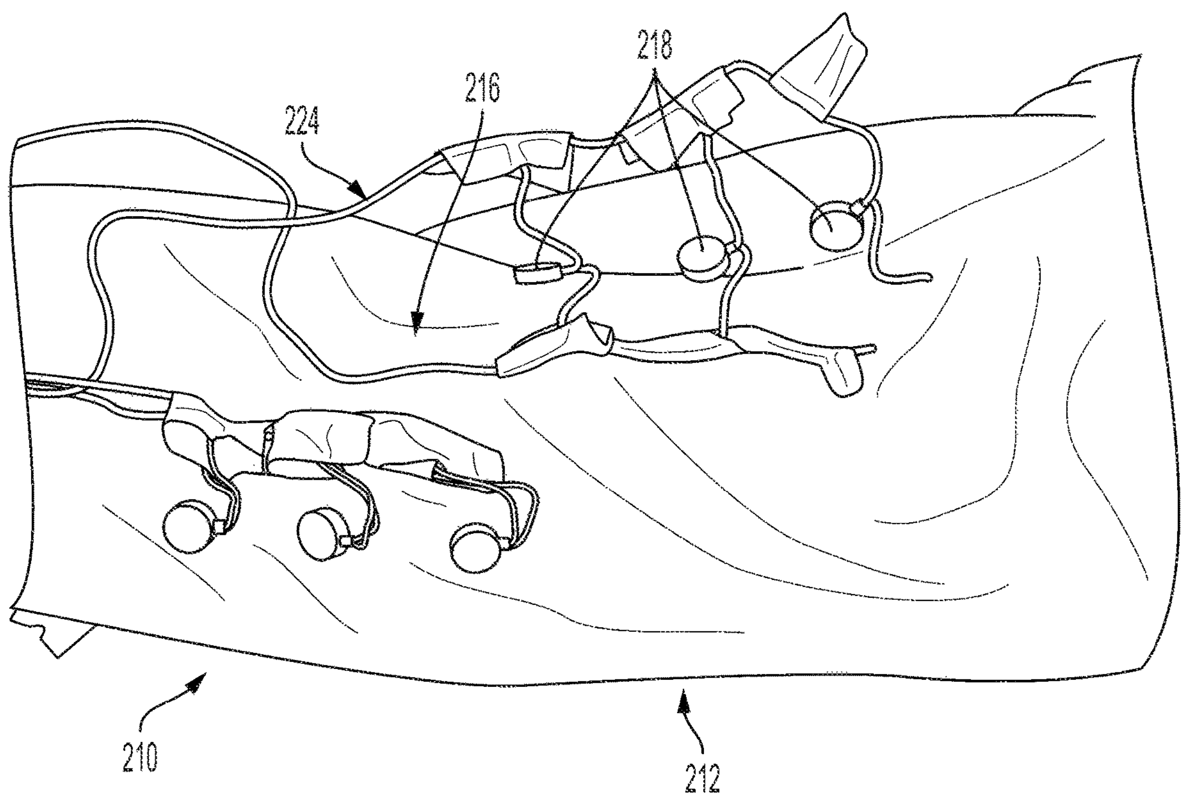
FIG. 24 illustrates the garment of FIG. 21 in a partially disassembled state.

In some embodiments, the garment assembly 210 also includes sensors 220. The sensors 220 can be part of the vibration layer 216, the sensors 220 can be a separate layer or, as shown in FIG. 22, at least some of the sensors 220 can be embedded in or positioned on the inner surface of the inner fabric layer 212 so that the sensor or sensors are positioned adjacent to or in contact with the wearer's skin (e.g., to sense the wearer's heart rate). The sensors 220 may be any type of sensor, including any of the types of sensors discussed herein. The vibration layer 216 can include a fill material 222 in which the vibration devices 18 are embedded, as shown in FIG. 22. FIGS. 23 and 24 show the vibration layer 16 without a fill material. The vibration layer 216 (or any of the other layers) also include cabling or wiring 224 (and defined pathways therefor) for electrical or data connection or communication between the various components, as necessary.

The vibration devices 218 can be secured to the surface of the inner and/or outer layer.

A vibration suppression layer can be included outside of the vibration devices 218 (e.g., between the vibration devices 218 and the outer layer 214 or outward from the outer layer 214) to prevent the outer layer or outside of the garment assembly from vibrating or to lessen the vibrations on the outside. A vibration amplifying layer can be included inward from the vibration devices 218 (e.g., between the vibration devices 218 and the inner layer 212 or inside of the inner layer 212) to transmit and distribute or spread out the vibrations from the plurality of vibration devices to further be transmitted to the wearer.

In some embodiments, the garment assembly 210 includes wireless communication (e.g., Bluetooth) so that it can communicate with a software application on a mobile device, such as a phone to provide a "smart" garment system. The wireless communication device can be housed on a PCB 226 (see FIG. 21) that is also in electrical and/or data communication with the vibration devices 218 and various sensors 220.

Figure 25:
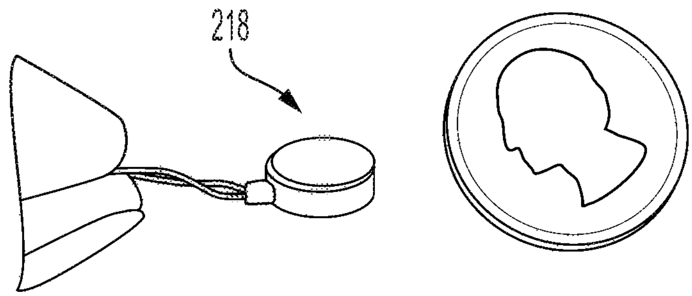
FIG. 25 illustrates a vibration motor of the garment of FIG. 21.
Figure 26:
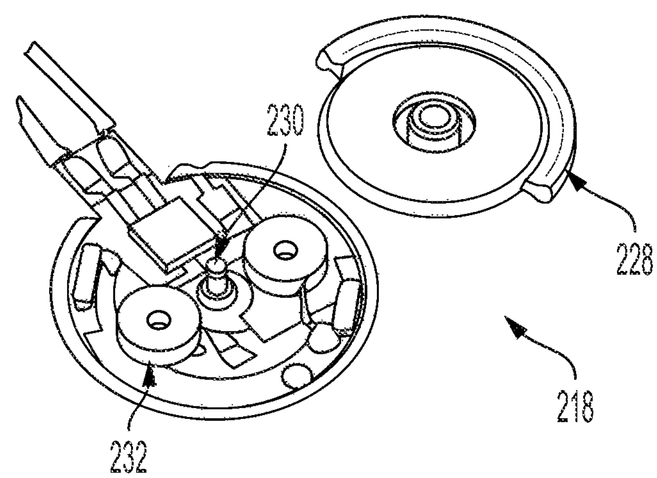
FIG. 26 illustrates the vibration motor of FIG. 25 in a partially disassembled state.

FIGS. 25 and 26 show an exemplary vibration device actuator or motor 218 that can be used in the present disclosure. FIG. 25 shows the vibration device 218 next to a U.S. quarter for exemplary scale purposes. FIG. 26 shows the interior of the vibration device 218, including a rotating weight 228 that provides the vibration, a rotating shaft 230 for rotating the weight and coils 232 that generate a magnetic field to rotate the shaft 230. Thus, in examples where the vibration devices 218 according to the illustrated embodiment are positioned to lie flat between the inner layer 212 and the outer layer 214 of the garment assembly 210, or to lie flat against the wearer's skin when the garment assembly 210 is worn, the shaft 230 will be aligned with the thickness 211 of the garment assembly 210 shown in FIG. 22. In such examples, each vibration device 218 will rotate the weight 228 about an axis normal to a plane on which the respective portion of the garment assembly 210 lies or to the nearest underlying portion of the wearer's skin. It will be appreciated that this type of motor is not a limitation on the present disclosure. Any type of motor that provides the desired vibration or amplitude is within the scope of the present disclosure. For example, the motor can include an electromagnet coil through which a shaft extends and where the shaft reciprocates (is pushed and pulled) linearly as a result of the magnetic field produced by the coil. The shaft can include some type of member or portion thereon that provides the vibration or percussion on the wearer's skin. Such linearly reciprocating motors may be oriented to cause the shaft to reciprocate on axes having any angular relationship with the thickness direction of the garment assembly 210 or the wearer's skin. For example, such linearly reciprocating motors may be arranged to cause the shaft to reciprocate parallel to the thickness 211 of the garment assembly 210 and perpendicular to the surface of the wearer's skin or, alternatively, perpendicular to the thickness 211 of the garment assembly 210 and parallel to the surface of the wearer's skin.

As discussed above, in another embodiment, the wearable device or garment assembly can include temperature modulation and application, for example, via integrated temperature control modules. The temperature control modules may be configured to provide heating, cooling, or both heating and cooling. The garment assembly can include either or both of vibration devices 218 and temperatures control modules, such as temperature control modules 234 described below.

Figures 27, 28:
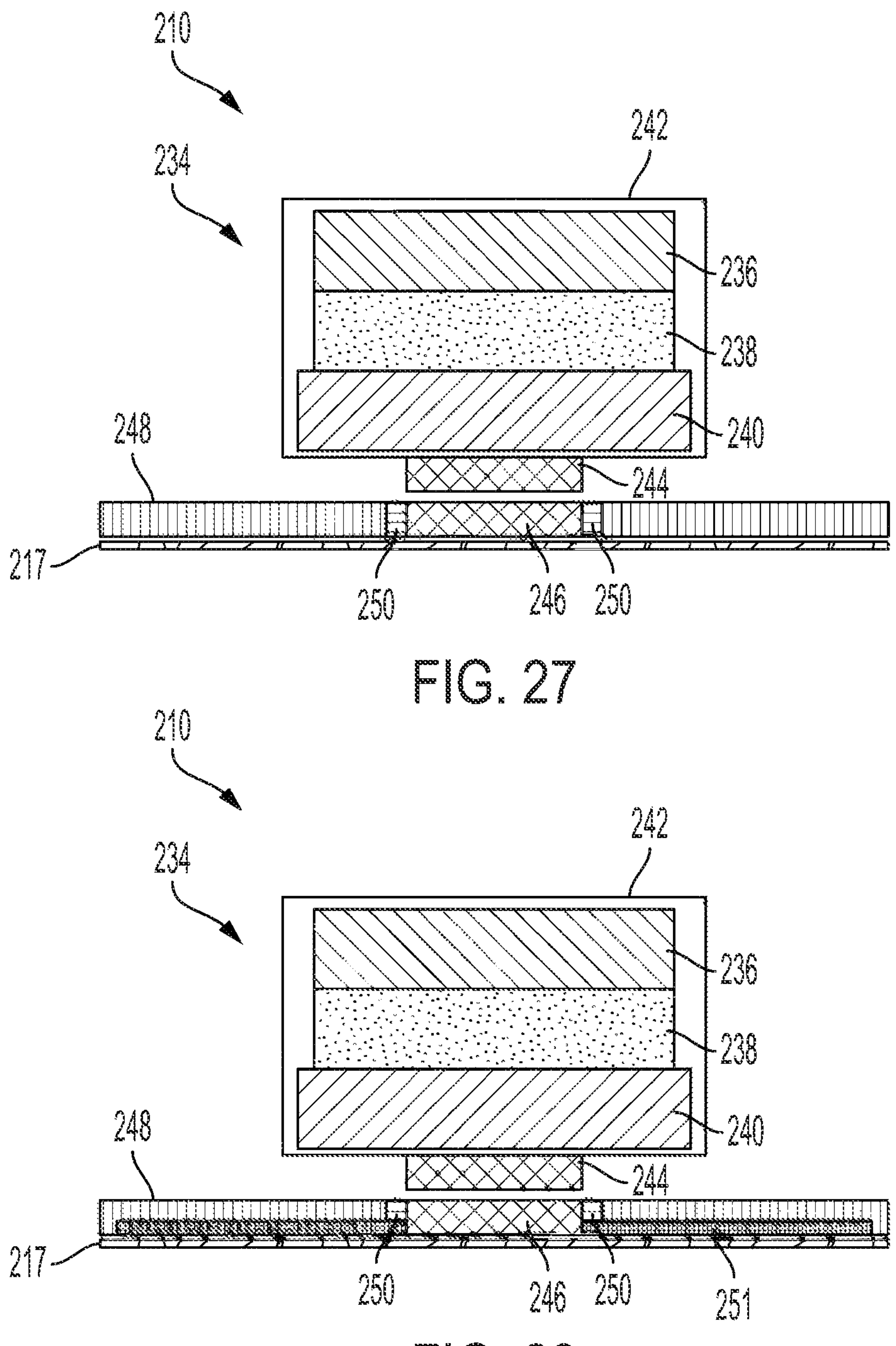
FIG. 27 is a cross-sectional elevation view of a temperature control module of the garment of FIG. 21.
FIG. 28 is a cross-sectional elevation view of a temperature control module of the garment of FIG. 21 according to another arrangement.
Figure 29:
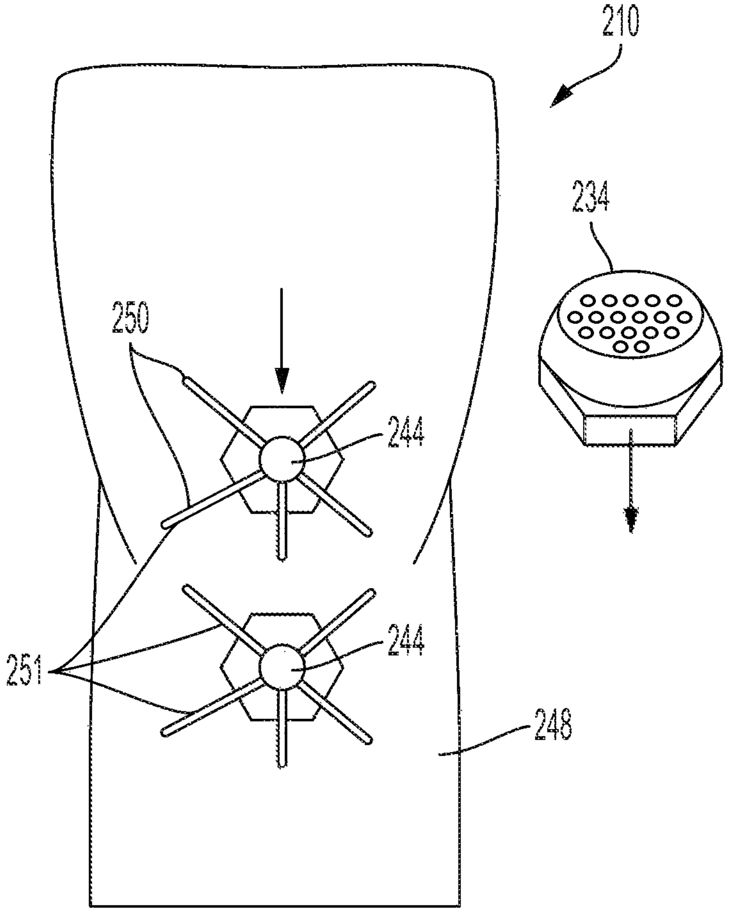
FIG. 29 illustrates a therapeutic garment according to another arrangement.

FIGS. 27-31 show an exemplary garment assembly 210, which may have any one or any combination of the features describe above with regard to the garment assembly 210, or which may be different from garment assembly 210 except for any commonalities described below. Garment assembly 210 is provided with a plurality of temperature control modules 234 positioned thereon or integrated therein. Temperature control modules 234 may be generally alike to temperature control modules 14, 114 describe elsewhere herein except for specifically stated or illustrated differences. FIG. 27 shows an embodiment where a garment portion 248 of the garment assembly 210 includes a magnet 246 positioned thereon or therein. At some locations on the garment portion, temperature control modules 234 are secured to the magnets 246. For example, as shown in FIG. 27, the garment assembly 210 can include temperature control modules 234 that are disposed throughout the garment assembly 210. In some embodiments, there is no garment or fabric layer between the temperature control module 234 and the user's skin 217. Instead, the bottom layer or surface of the temperature control module 234 or some other heat conductive portion or material contacts the user's skin 217.

As shown in FIG. 27, in the illustrated embodiment, the temperature control module 234 includes a fan 236, a heat sink 238 and a thermal element 240, such as, for example, as a Peltier module or device, another type of thermoelectric heater, cooler, or heat pump, or a chemical heater or cooler, that are contained within the module housing 242. In this embodiment, the temperature control module 234 includes a magnet 244 on the bottom thereof that can be magnetically connected or secured to a magnet 246 on or in the fabric portion or garment portion 48 of the garment assembly 210. A frame 250 configured for retaining the magnet 246, such as, for example, a plastic frame, metal collar, or any other retaining structure, can be embedded in or attached to the garment portion 248.

In some embodiments, the magnet to magnet system (i.e., magnets 244 and 246) secures the temperature control module 234 to the garment portion 248 and transfers or conducts the heat or cold from the module to the user's skin as the magnets may be made of a heat and/or cold conductive material.

FIG. 28 shows an embodiment similar to FIG. 27, but with flexible thermally conductive members 250, such as a band, patch or the like made from thermally conductive material, such as, for example, copper, aluminum, or other metals or metal alloys, or certain ceramics, to help transfer heat or cold to increase the effective area of heating or cooling treatment. The thermally conductive members 250 may be in contact with or connected to the magnet so that the heat or cold is conducted from the magnet and through the heat conductive member 250. FIG. 9 shows a temperature control module 234 exploded from a garment portion 248 with a matrix of bands 251, which may themselves be thermally conductive members 250, surrounding the magnet 246. FIG. 210 shows a temperature control module 234 exploded from the magnet 246 on the garment portion 248 and illustrates how the temperature control module 34 may be attached to the magnet 246.

FIG. 31 shows a schematic view of a garment assembly with a plurality of locations where a temperature control module 234 can be secured or attached thereto. FIG. 211 shows a number of the locations without a temperature control module 34 and thus shows the connecting magnet 246 and a number of the locations where a temperature control module 234 is attached to the garment assembly. This gives the user wearing the garment (a shirt in FIG. 30) a plurality of options for where to position one or more temperature control modules 234. For example, if the user has a right shoulder issue they are treating, they may only place one or more temperature control modules 234 in that location to heat or cool the right shoulder. At a later time they can use the same shirt to treat a different condition, such as, for example, an abdominal issue.

FIG. 32 shows a garment assembly 210 that embodies a knee wrap or sleeve that includes both vibration devices 218 and temperature control modules 234. As is shown in FIG. 33, the vibration devices 218 are embedded in the garment portion 248 (e.g., between inner and outer fabric layers) and are arranged around the magnets 246 such that temperature control modules 234 can be connected to the magnet 246 above and below the knee cap. This is just an example and any pattern or number of vibration devices 218 and temperature control modules 234 can be utilized. It will be appreciated that any configuration of vibration devices 218 is within the scope of the present disclosure. The vibration devices can be configured to treat certain issues and can be placed in patterns around the sleeve or wrap, such as a triangle, star, circle, spiral, other pattern, etc. and can increase blood flow and provide therapeutic benefit as desired.

As shown in FIG. 33, in some embodiments, the garment assembly may 210 include a plurality of magnets 246 in groups of overlapping magnets, designated **246*a*, 246*b* and 246*c* in the illustrated arrangement having three magnets per group, or a single magnet with a plurality of locations where the magnet 244 on the temperature control modules 234 can be placed in order to allow the temperature control modules 234** to be movable or positionable within the same general area. This allows the user to move the module to the exact location of the issue. It also allows a single garment size to be usable by different uses (because no two bodies are exactly the same). In another embodiment, the majority of or all of the garment can be magnetized, thus allowing the module to attach anywhere.

In the embodiment shown in FIG. 33, three magnetic circles or locations **246*a*, 246*b* and 246*c* are provided and give the user three positions for placing the temperature control modules 234**, for example, on the shoulder.

Devices according to some aspects of the present disclosure include a smart vibration system. It will be appreciated by those of ordinary skill in the art that at a certain frequency (depending on the mass attached to the system), vibrations can make a user's body resonate and therefore increase the amplitude of the perceived vibration. To take advantage of this resonant frequency principle (which is different from person to person and from body part to body part), devices according to the present disclosure may include a closed loop system with sensors that scan through the different speeds of the vibration devices or motors until the resonant frequency is found. This can be achieved by adding accelerometers near the motor locations to can measure the actual vibration that is being generated when the motor is attached to the body part. In an exemplary embodiment, strain gages that can measure displacement of the garment are included in the location of the motor.

In some embodiments, the garment assembly is washable and includes at least some components that are embedded in, attached to, etc. permanently in the garment (e.g., waterproof enclosed motors, cabling, etc.) and other components that are removable (battery pack, PCB). The permanent components may be sealed in the garment (e.g., between garment layers and the user can wash the garment after removing the power unit system (battery pack, PCB, etc.).

In some embodiments, the garment assembly can be a wrap or strap garment assembly 52 that includes a temperature control system and localized vibration. The garment assembly may be incorporated in a compression wrap. One or more of the layers of the device can include vibration capability. Furthermore, any of the concepts disclosed herein can be applied to a compression wrap (e.g., smart technology, clusters of vibration devices, temperature control module(s), etc.). The temperature control modules may or may not contain an integrated battery (i.e., within the module). The modules can be removed from the strap device and placed in different cavities 53 in the strap assembly 52 depending on the desired treatment.

The temperature control modules may be different sizes depending on the muscle group or the surface area desired be treated. The device (or separate devices) may also include different sized and shaped straps to accommodate different body parts.

Figure 35:
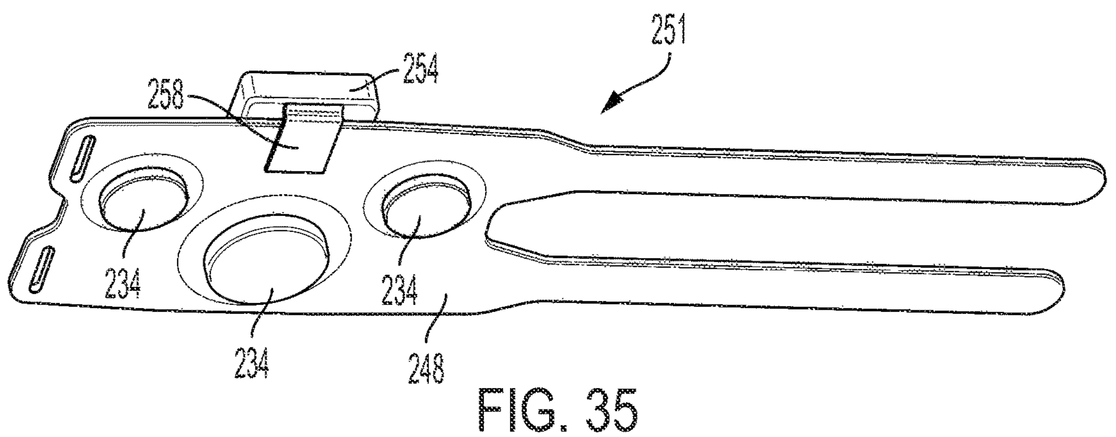
FIG. 35 is an oblique perspective view of an under side of the strap of FIG. 34.
Figure 36:
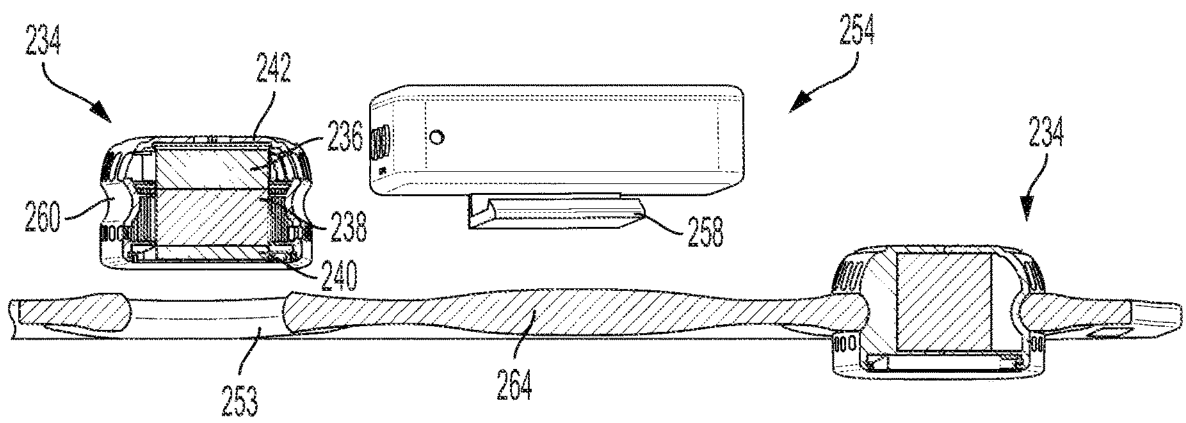
FIG. 36 is a cross-sectional view of the strap of FIG. 34.
Figure 37:
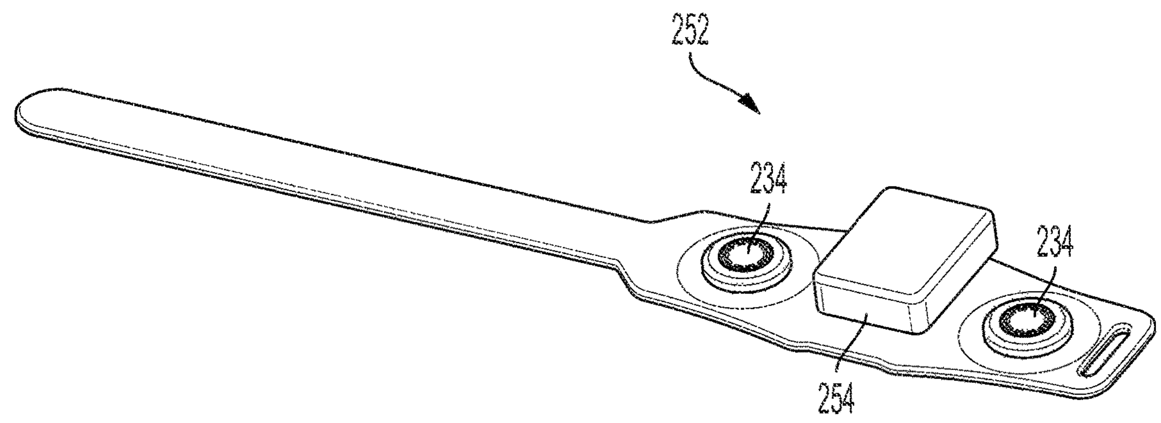
FIGS. 37-39 are oblique perspective views of a top side of straps according to other arrangements retaining temperature control modules.

FIGS. 34-36, 38, and 39 show knee straps 251, 257, 259 and FIG. 37 shows a wrist strap 252 with openings or cavities for receiving temperature control modules. FIGS. 34-39 are illustrated to scale, and thus show specific arrangements of larger and smaller temperature control modules 234. However, the illustrated arrangements of the larger and smaller temperature control modules 234, and the proportions of the subjects shown in FIGS. 34-39 generally, are merely specific examples, and variations on the relative sizes of all such features are contemplated. The straps 251, 252, 257, 259 may be generally alike to the straps of the strap assembly 10 described above except for any differences specifically illustrated or described herein. The straps 251, 252, 257, 259 each include openings or cavities for receiving temperature control modules. FIGS. 34-39 illustrate the straps 251, 252, 257, 259 with the openings filled with temperature control modules 234 according to the examples described immediately above, but the according to various examples the straps can have openings for receiving any type of temperature control modules described herein. A control member and/or battery pack 254 is also secured to each strap 251, 252, 257, 259. In this embodiment the battery pack 254 is also removable (it is clipped onto the strap via a clip 258). The controller 254 can be electrically connected to and in data communication with the modules 234 so that the modules are powered and can be controlled by the controller 254. Wiring is shown connecting the battery pack/controller 254 to the modules 234. The wiring can be embedded in the main body portion 264 and plugs or jacks can be used for attaching and detaching the electrical connections. The wiring can also be external. Wireless connectivity between any and/or all components can also be included.

Figure 34:
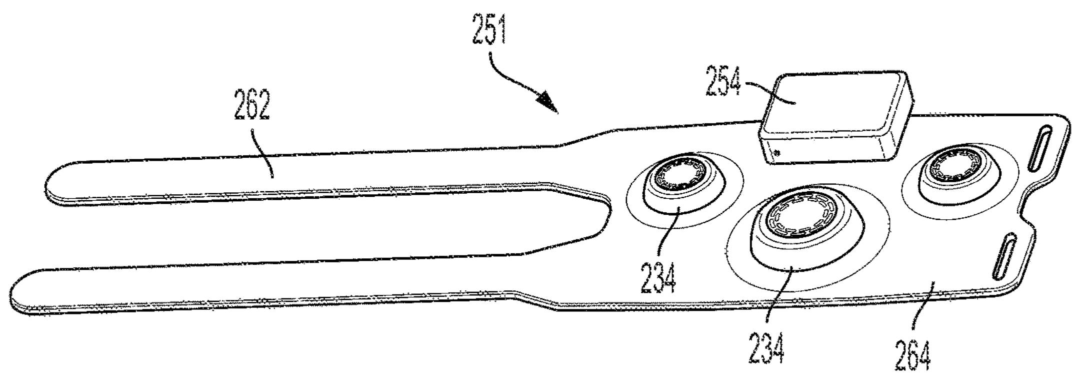
FIG. 34 is an oblique perspective view of a top side of a strap retaining temperature control modules.

FIGS. 34-36 show three temperature control modules 234 in the openings of the knee strap 251, which includes strap extensions 62 and a main body portion 264 where the modules are located. Modules can also be located on the straps. In another embodiment, a battery can be located in the module, thus making each module independent and interchangeable such that it can be simply placed in the cavity or a strap garment assembly or secured via a magnet or other attachment mechanism to a "wearable" garment assembly, such as garment assembly 210.

As shown in FIGS. 36, in some embodiments, the module housing 242 includes a groove 260 that receives a portion of the main body portion 264 so that it can be positioned in the cavity 253 (or module seat). It will be appreciated that the main body portion 264 is made of a material that is pliable and flexible enough to allow the modules 234 to be inserted into the cavities 253 and removed therefrom (e.g., pressed into place and removed therefrom). In embodiments with larger and smaller modules, the one or more larger modules are the main heat or cold provider (to the user). The heat may be conducted outwardly from the larger module. The smaller modules can be used to provide extra heat or cold where it is difficult to conduct the heat from the larger module. In some embodiments, the main body portion and/or straps include heat conductive material therein or thereon.

Figure 38:
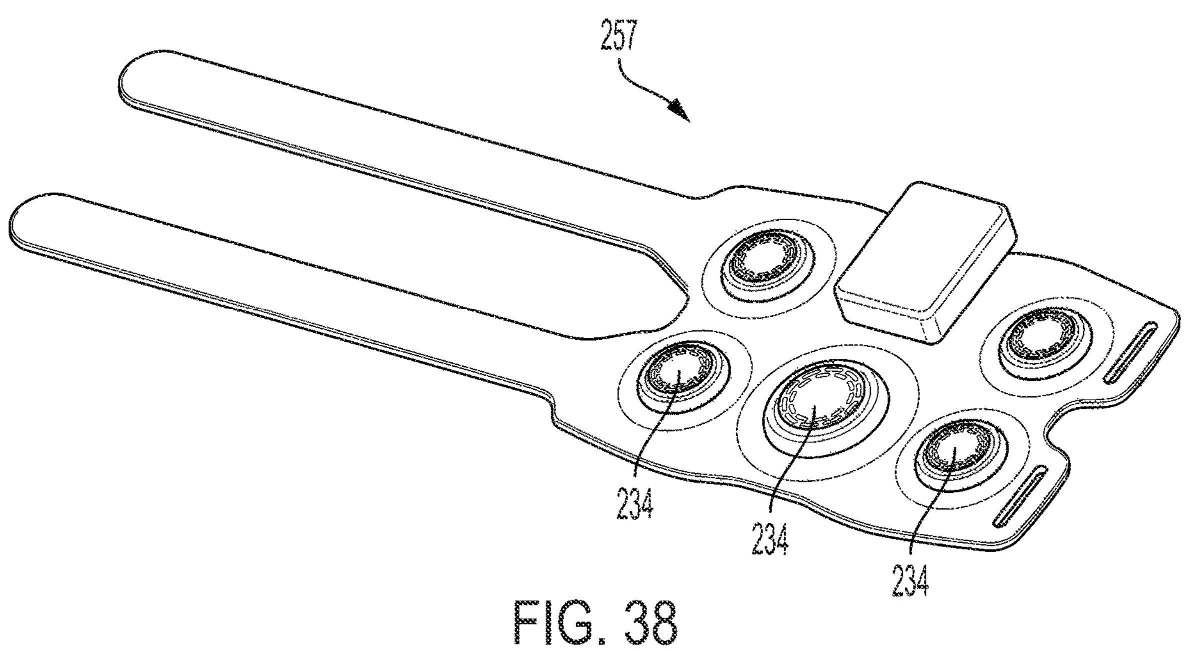
Figure 39:
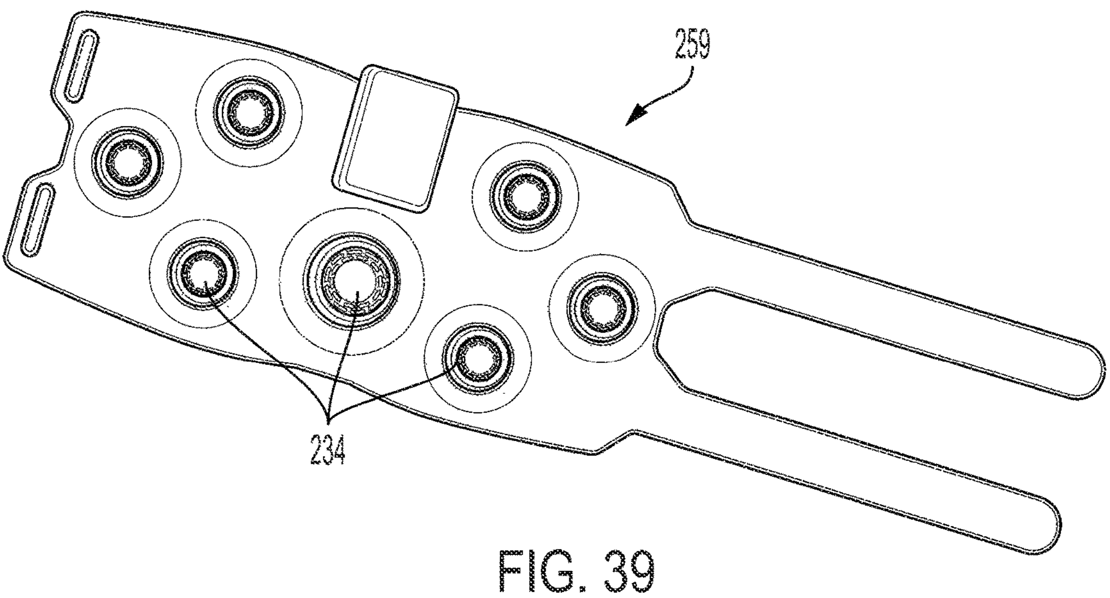

FIGS. 37-39 show other configurations of strap assemblies 252, 257, 259 including two, five and seven temperature control modules 234, respectively.

Figure 40:
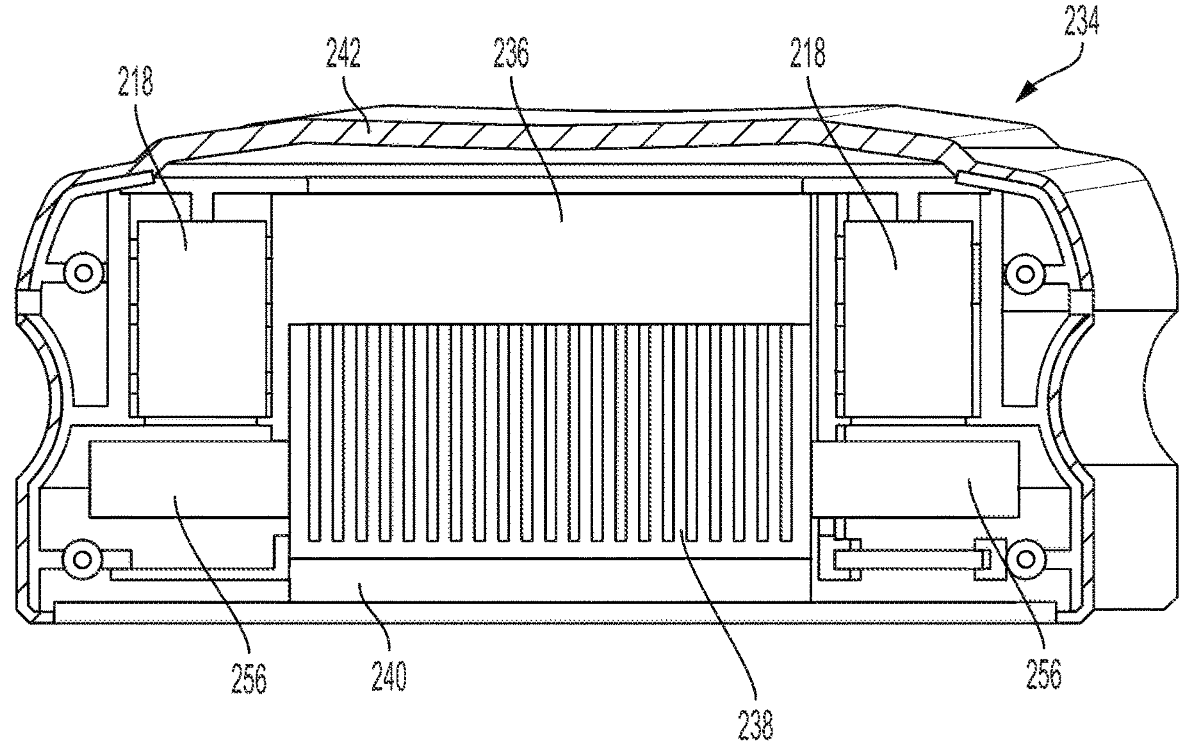
FIG. 40 is a cross-sectional view of a temperature control module according to another arrangement.
Figure 41:
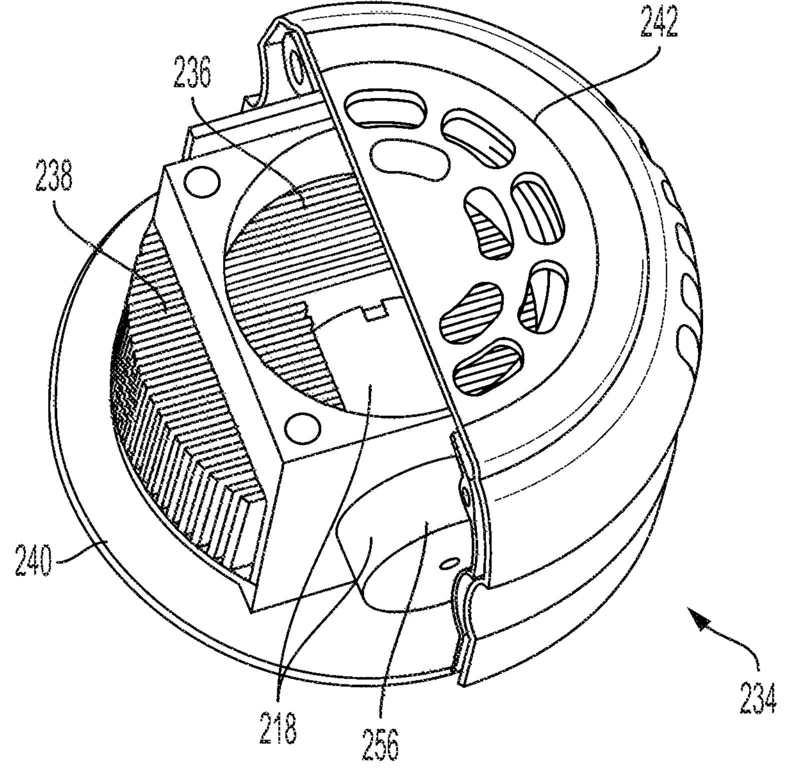
FIG. 41 is a partially cut away view of a temperature control module according to another arrangement.

As can be seen in FIG. 34, the embodiment shown includes a larger module 234 and several smaller modules 234. FIG. 40 is a cross-section of the larger temperature control module 234 and showing that it contains similar components to all of the above described temperature control modules 14, 114 for the heating and cooling, but also includes vibration devices or motors 218 therein with a counterweight 256. The smaller modules may have the same configuration or may omit the vibration devices. In another embodiment, as shown in FIG. 41 shows another embodiment of a temperature control module 234, where one or more vibrating devices 218 can be placed on or in the heat sink 238. Vibration devices can also be included embedded in the main body portion or strap portions. It will be appreciated that any and all of the embodiments discussed or disclosed herein and any of the components or concepts included in the embodiments are all completely interchangeable, swappable and usable together.

Similar strap assemblies or wraps can be configured to fit any body part or multiple body parts, e.g., shoulder, back, knee, elbow, wrist, neck, ankle, etc.

Figure 42:
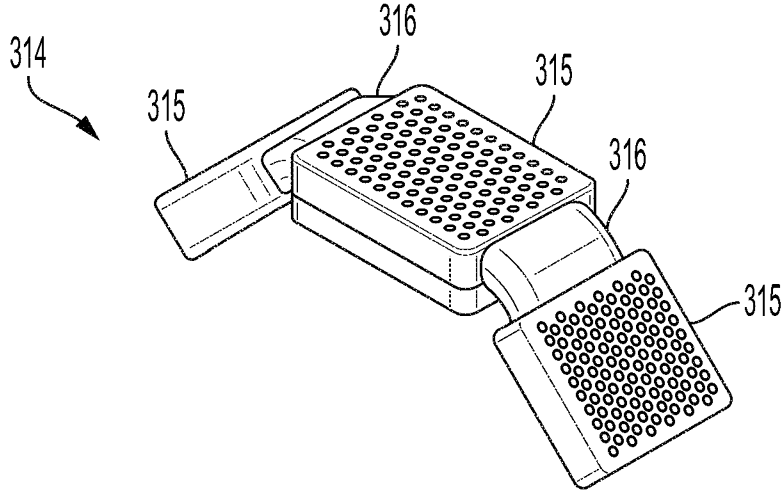
FIG. 42 is an oblique perspective view of a temperature control module according to another arrangement.

FIG. 42 shows a temperature control module 314 according to another example. Temperature control module 314 includes three sub-modules 315, each of which includes a contact, thermal element, heat sink, and optionally a fan as describe above with regard to any of the other temperature modules 14, 114, 214 above. The sub-modules 315 are connected in a row by flexible connectors 316, which may be any type of resiliently flexible material such as, for example, metal or plastic. Any of the foregoing garments, straps, or assemblies usable with any type of temperature control module may be adapted to receive the temperature control module 314 in the same way.

Figure 43:
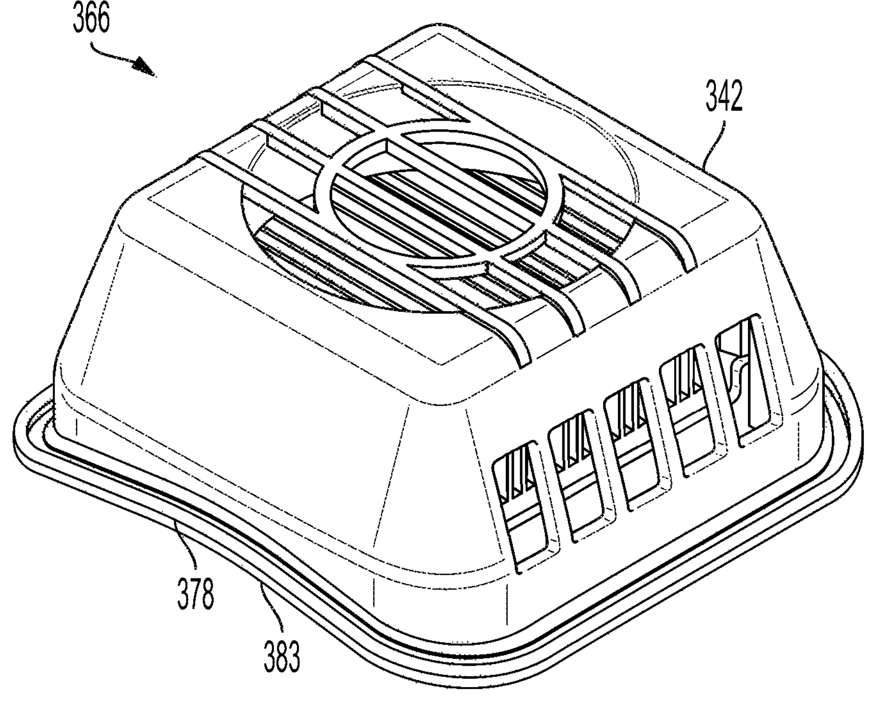
FIG. 43 is an oblique perspective view of a temperature control module according to another arrangement.
Figure 44:
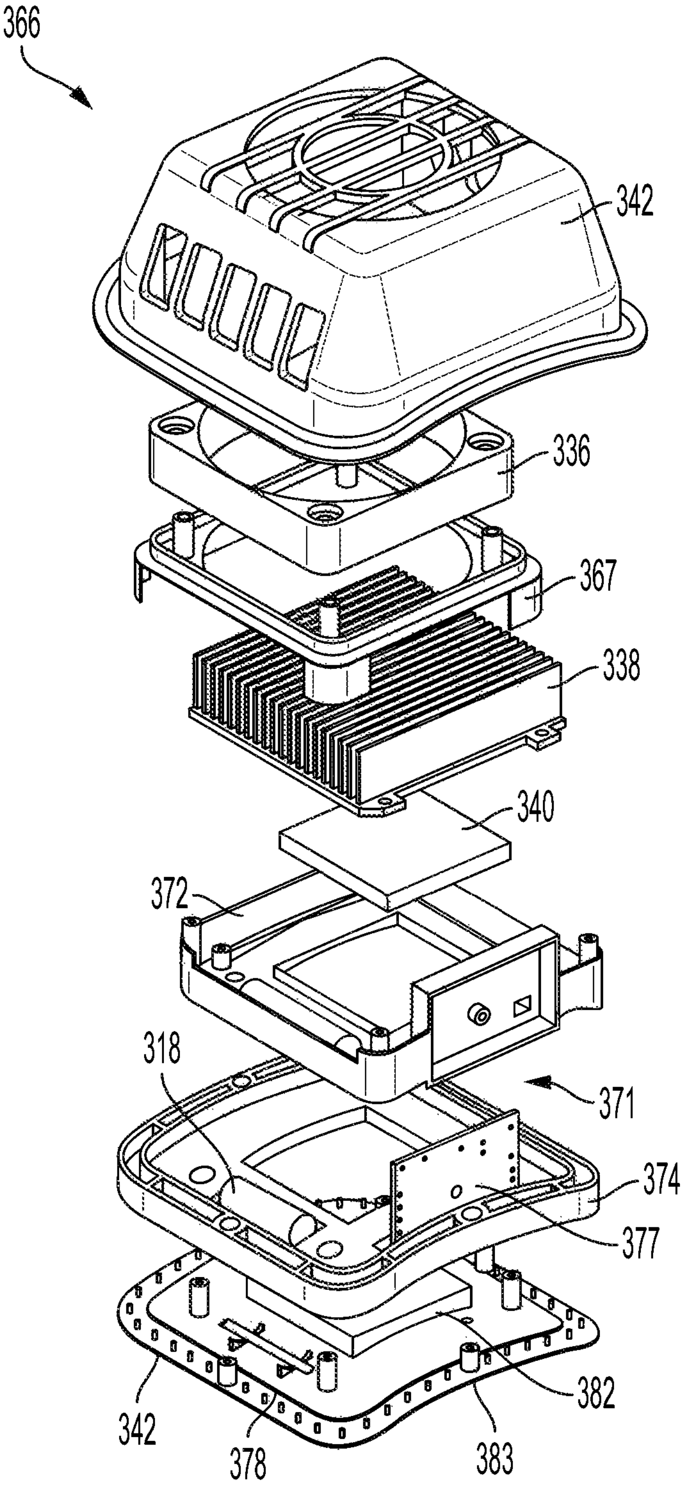
FIG. 44 is an exploded view of the temperature control module of FIG. 43.
Figures 45, 46:
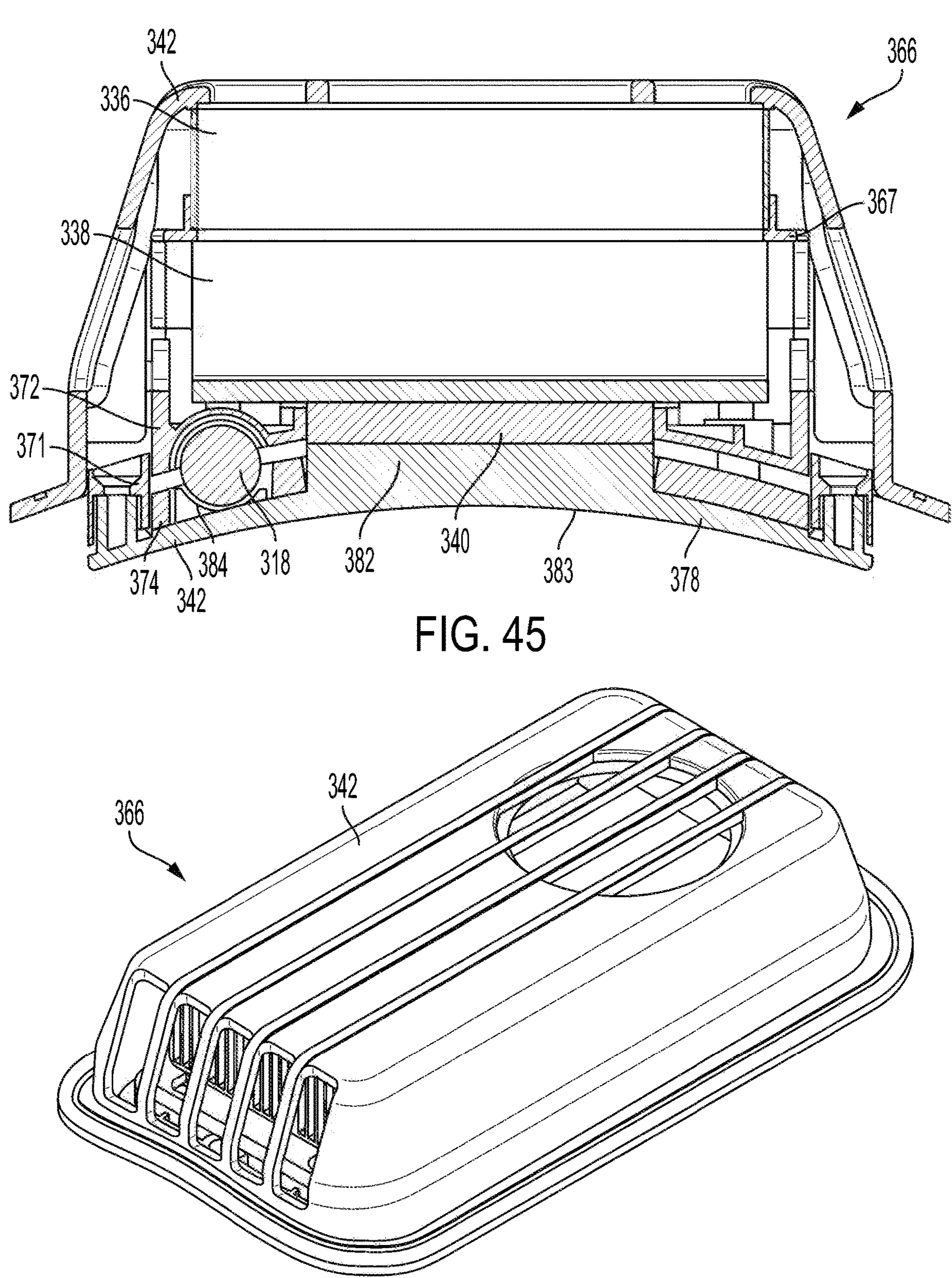
FIG. 45 is a cross-section of the temperature control module of FIG. 43.
FIG. 46 is an oblique perspective view of a temperature control module according to another arrangement.

FIGS. 43-45 show another embodiment of a temperature control module 366 that includes a concave module structure or bottom surface so that it can adapt to the contour of different portions of the body, such as the thigh, calf, etc. Many of the components of temperature control module 366 are similar to temperature control module 234 and the other temperature control modules discussed herein except where explicitly stated or shown otherwise. As shown in FIG. 44, the temperature control module 366 includes module housing 342, fan 336, heat sink 338, Peltier device 340, vibration device 318 and counterweight 356. In some embodiments, temperature control module 366 also includes a fan bracket 367 and a Peltier housing 371 that includes an upper housing portion 372 that houses the Peltier device and a lower housing portion 374 that houses the vibration device 318 and a PCB 377. The module housing 342 may optionally include a lower portion 378 that includes the concave surface 383 on a bottom thereof. The lower portion 378 also includes a conductive member 382 that conducts heat or cold from the Peltier device 340 to the concave bottom surface. The upper and lower housing portions of the Peltier housing 371 define a motor recess 384.

Figures 47, 48:
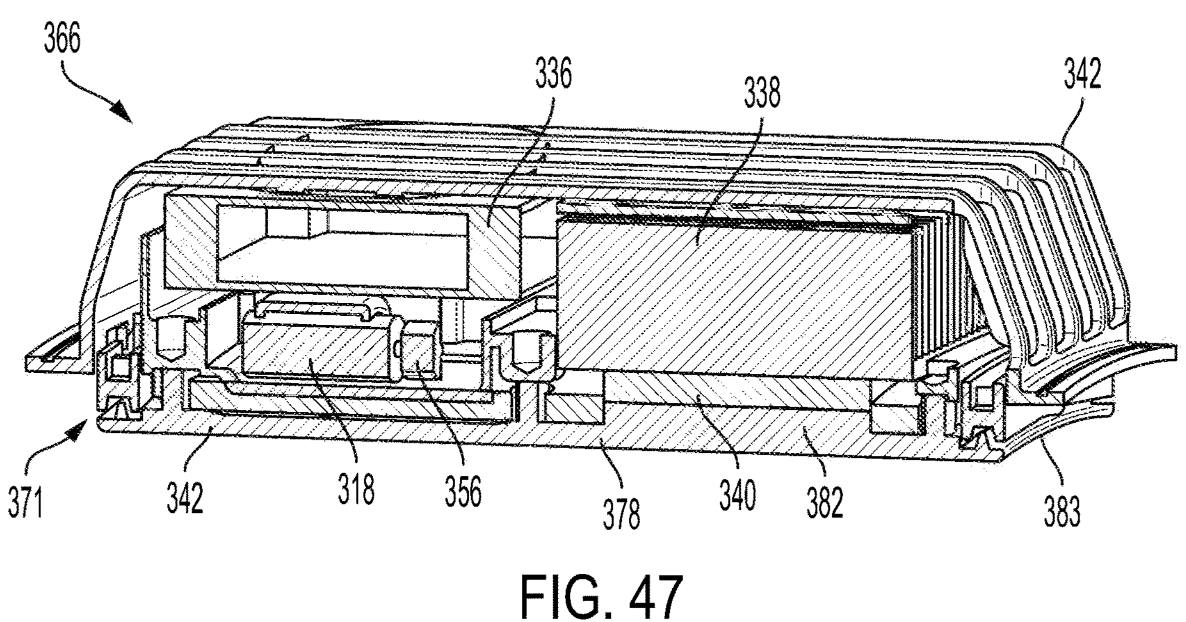
FIG. 47 is cross-section of the temperature control module of FIG. 46.
FIG. 48 is a cross-section of the temperature control module of FIG. 46 on a plane normal to the cross-section of FIG. 47.

FIGS. 46-48 show temperature control module 368 that is similar to temperature control module 366 and other temperature control modules discussed herein except where explicitly stated or shown otherwise. Temperature control module 368 is longer than temperature control module 366 and includes the fan 336 next to the heat sink 338 instead of on top of the heat sink 338. All temperature control modules herein include vents or openings in the module housing to allow heat to be dissipated therefrom.

Figure 49:
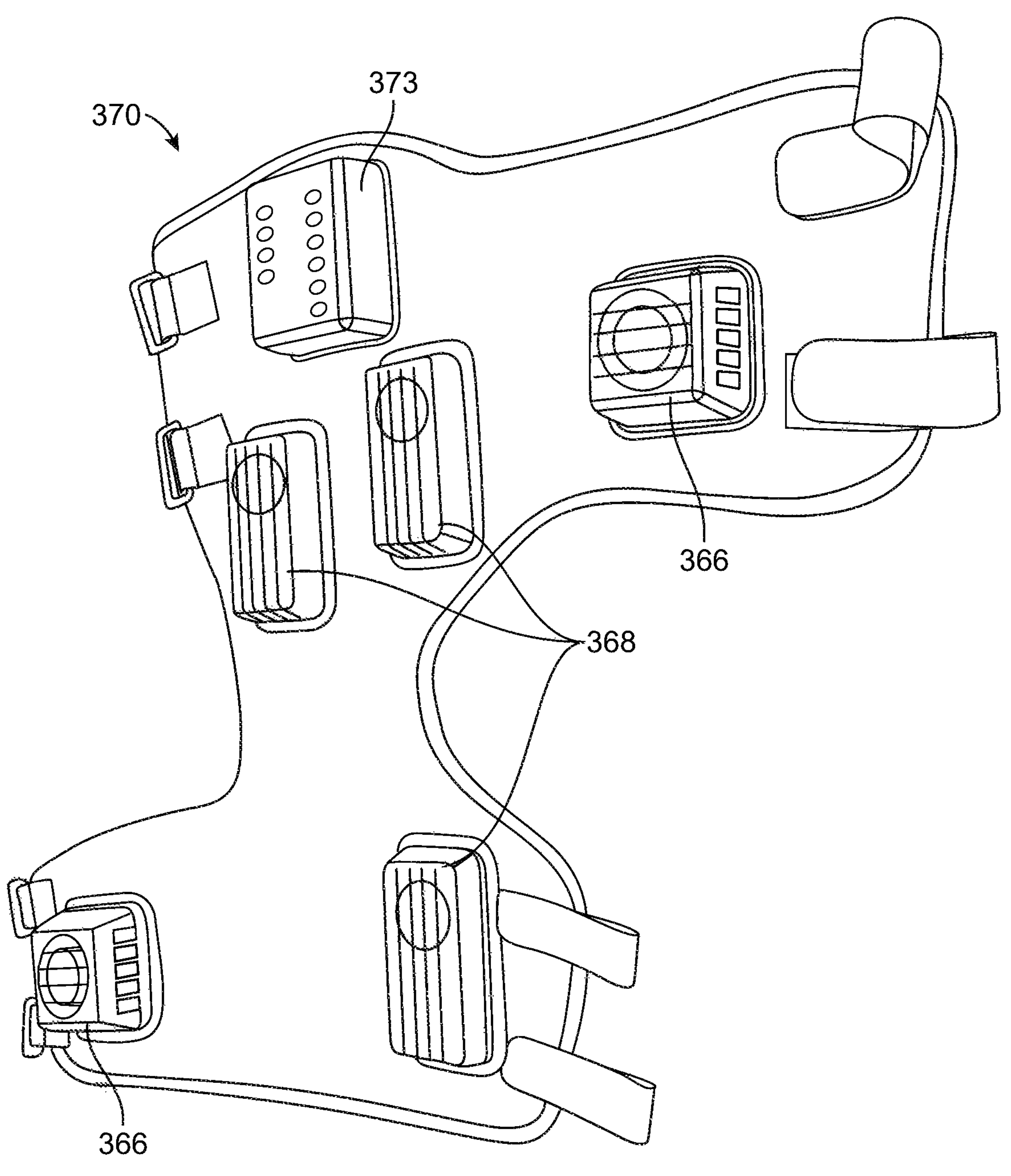
FIG. 49 is an oblique perspective view of an outer side of a garment retaining the temperature control modules of FIGS. 43 and 46.
Figure 50:
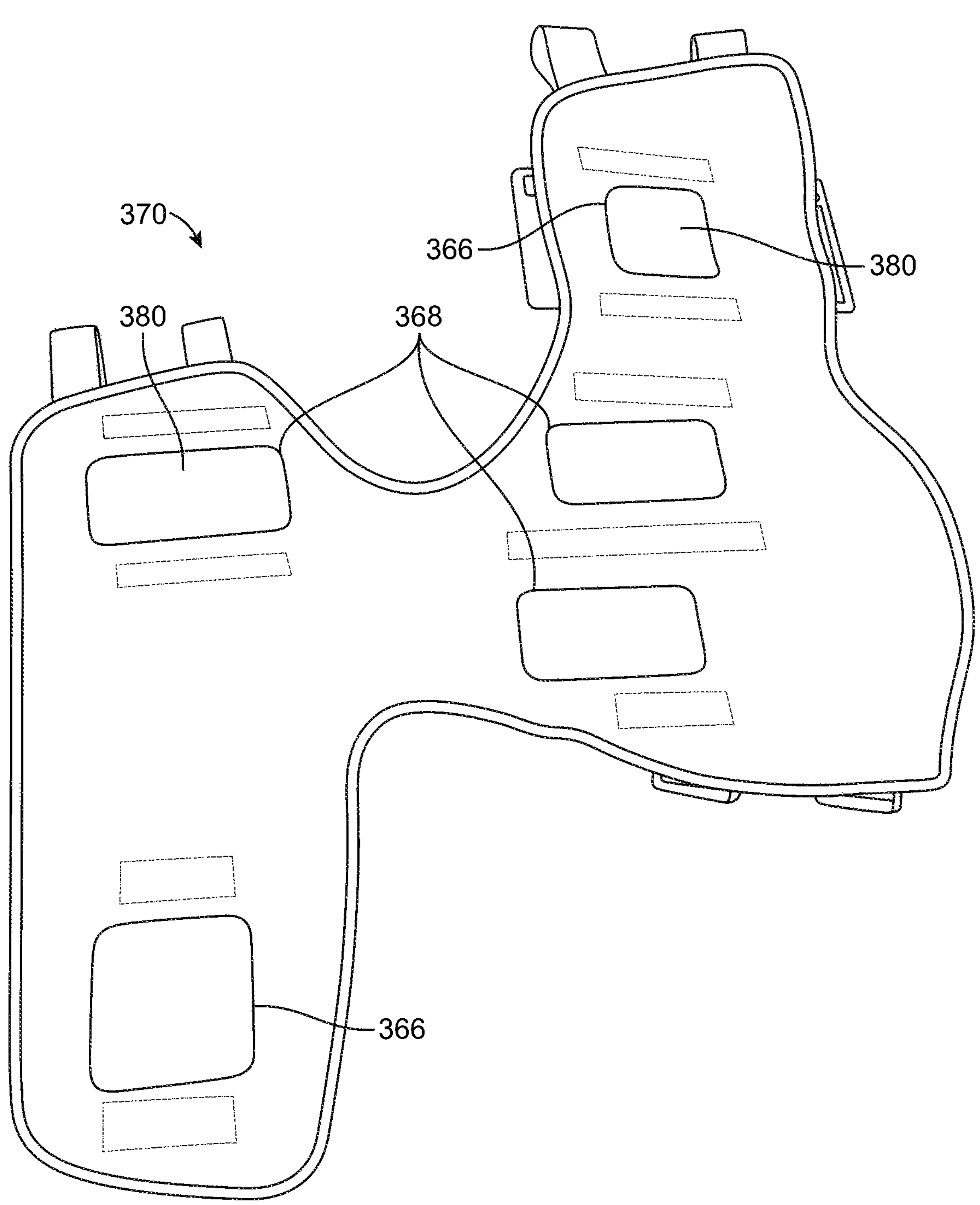
FIG. 50 is an oblique perspective view of an inner side of the garment of FIG. 49.

FIGS. 49-50 show the temperature control modules 366 and 368 included in a leg strap assembly 370. As shown in FIGS. 49 and 50, the strap assembly 370 includes three of the longer temperature control modules 368, two temperature control modules 366 and a controller or control assembly 373. From a review of FIG. 50 it can be seen that the bottom surface 383 of the temperature control modules 366 and 368 are curved so that they follow the contours of the leg. It will be appreciated that the straps can be include Velcro or the like for securement.

Figure 51:
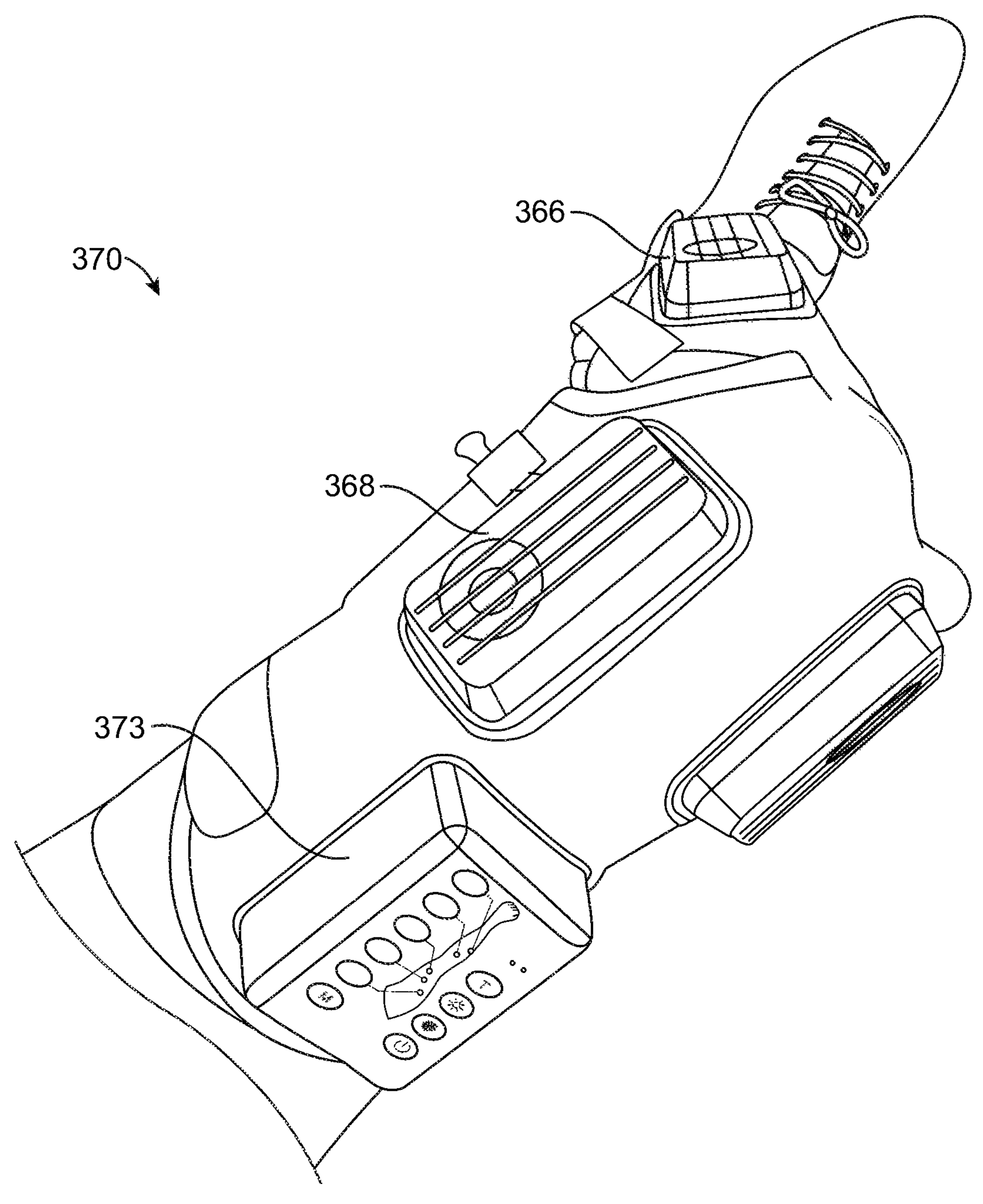
FIGS. 51 and 52 illustrate the garment of FIG. 49 being worn on a leg.
Figure 52:
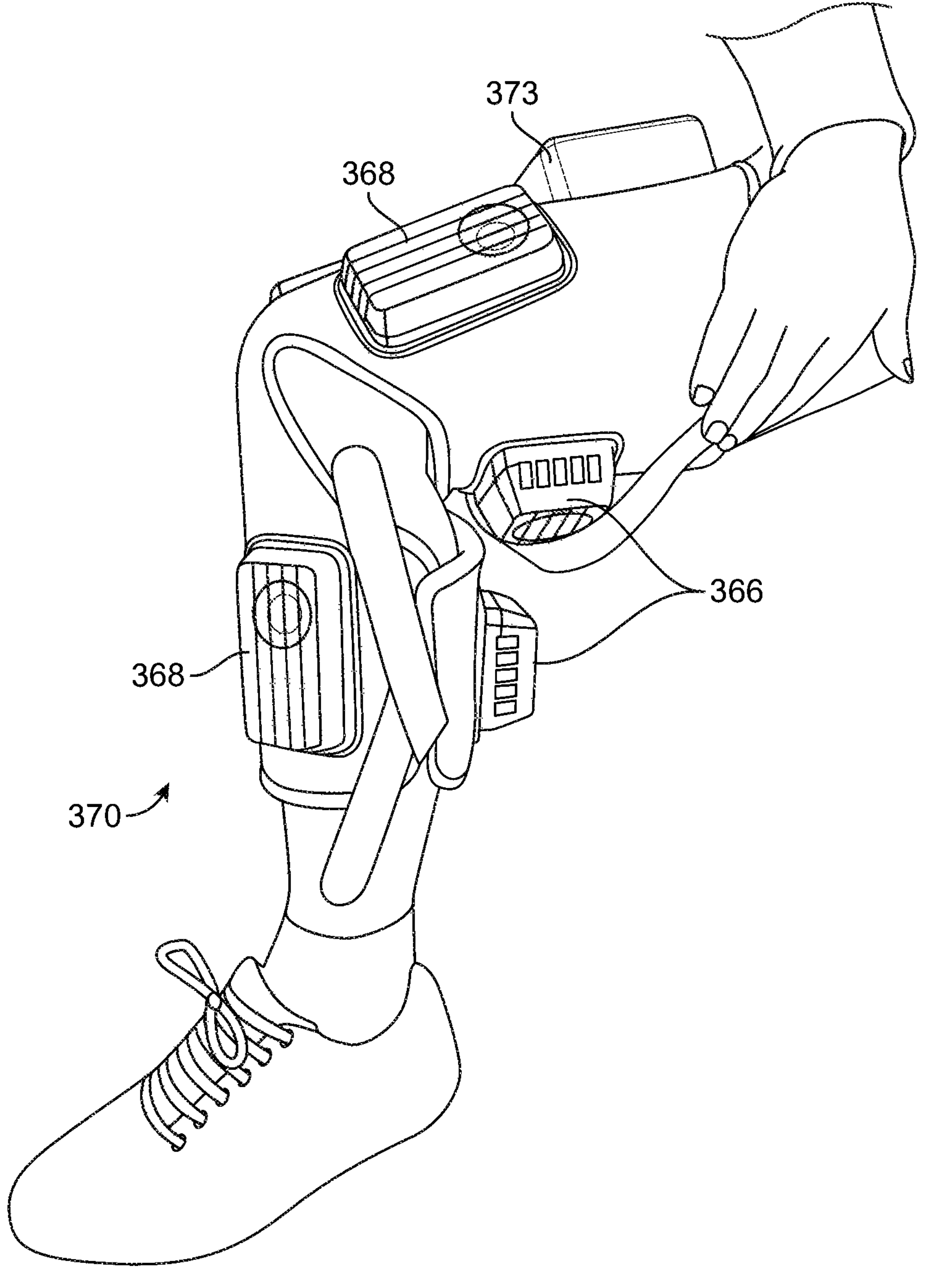
Figure 53:
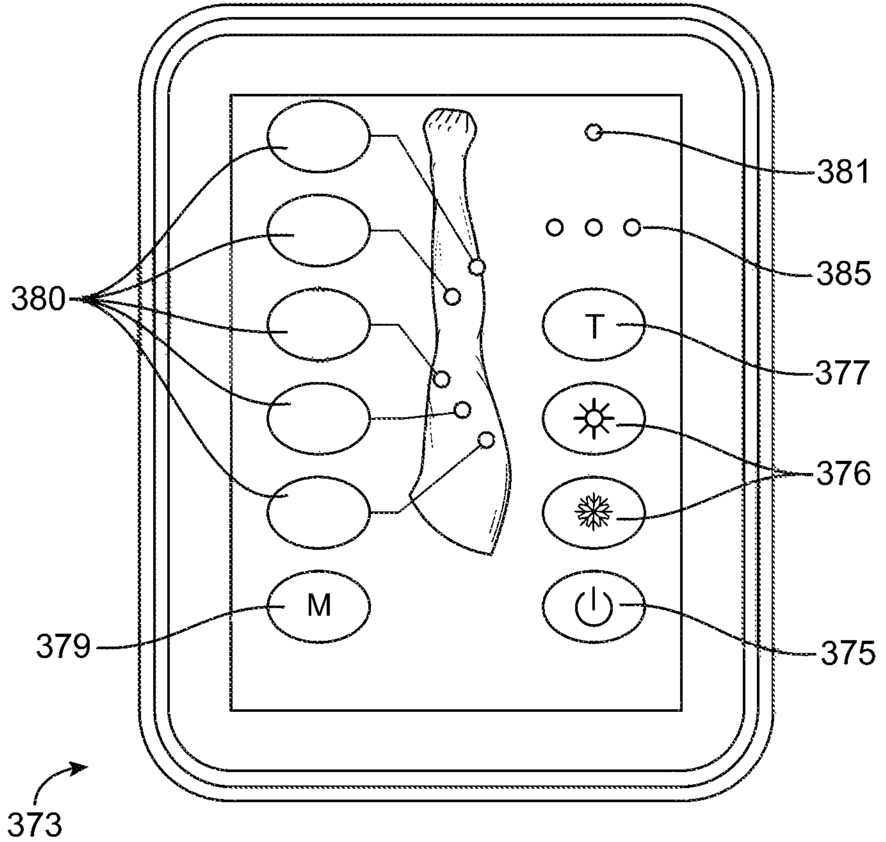
FIG. 53 illustrates a control assembly for the garment of FIG. 49.

FIGS. 51 and 52 show the strap assembly 370 on a user's leg and, in particular, the temperature control modules 366 on the user's calf and hamstring and the temperature control modules 368 on the user's quadricep and shin area. FIG. 53 shows the control module or assembly 373 and a plurality of buttons or switches thereon for controlling the modules 366 and 368. Button 375 turns the device on and off, buttons 376 control cooling and heating button 376 controls the time or duration, button 379 is for changing modes, and buttons 380 are for controlling the vibration devices 318 and turning them on and/or off for various body parts as shown on the depiction of a leg on the module and the LED lights related thereto. Light 381 is the charging indicator. LED lights 385 are the time light indicators. Some of the features are controlled by multiple pushes of the associated button. In an exemplary embodiment, the buttons may work as follows. Pushing the mode button 379 may cycle through the following vibration patterns—constant, wave, regular, wave, off. The cold button 376—one press for 5° C. control, two presses for 10° C. control, three presses for unlimited control and four presses to turn off. The hot button 376—one press for 38° C. control, two presses for 40° C. control, three presses for 42° and four presses to turn off. The time button 377—power on sets the time to 15 minutes, one press sets to 30 minutes, two presses sets to 60 minutes, third press for unlimited time.

Devices according to some aspects of the present disclosure provide flexibility so that the modules, such as modules including either or both of the vibration devices or thermal modules, can be used on, for example, strap devices (e.g., FIG. 34) and garment or wearable devices (e.g., FIG. 31). Mounting the modules on strap devices provides high performance and efficacy. The strap allows for multiple modules to work together and treat a wide area. Mounting the modules on a wearable device (e.g., shirt, pants, shorts, etc.) provides the user with the vibration garment and the flexibility of adding temperature control modules when desired.

Figure 54:
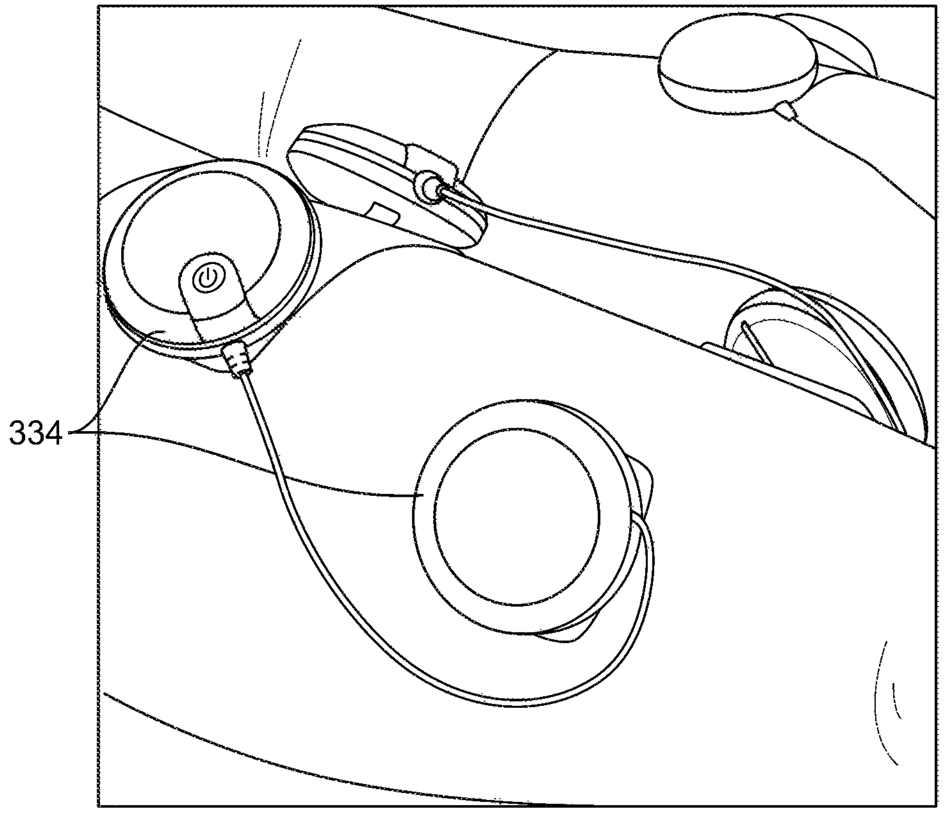
FIG. 54 illustrates temperature control modules according to another aspect of the disclosure adhered to a leg.

In some embodiments, the modules 234, 366, or 368 can be adhered, placed or positioned, directly on a user's skin, as shown in FIG. 54. This embodiment allows the user or a professional practitioner to place the modules in the desired position or spot. The module may include an adhesive layer or sticker on the bottom thereof. In some embodiments, the sticker has good thermal conductivity properties and provides a "thermal bridge" between the module 334, which may be alike to any of the other temperature control modules disclosed herein, and skin.

Figure 55:
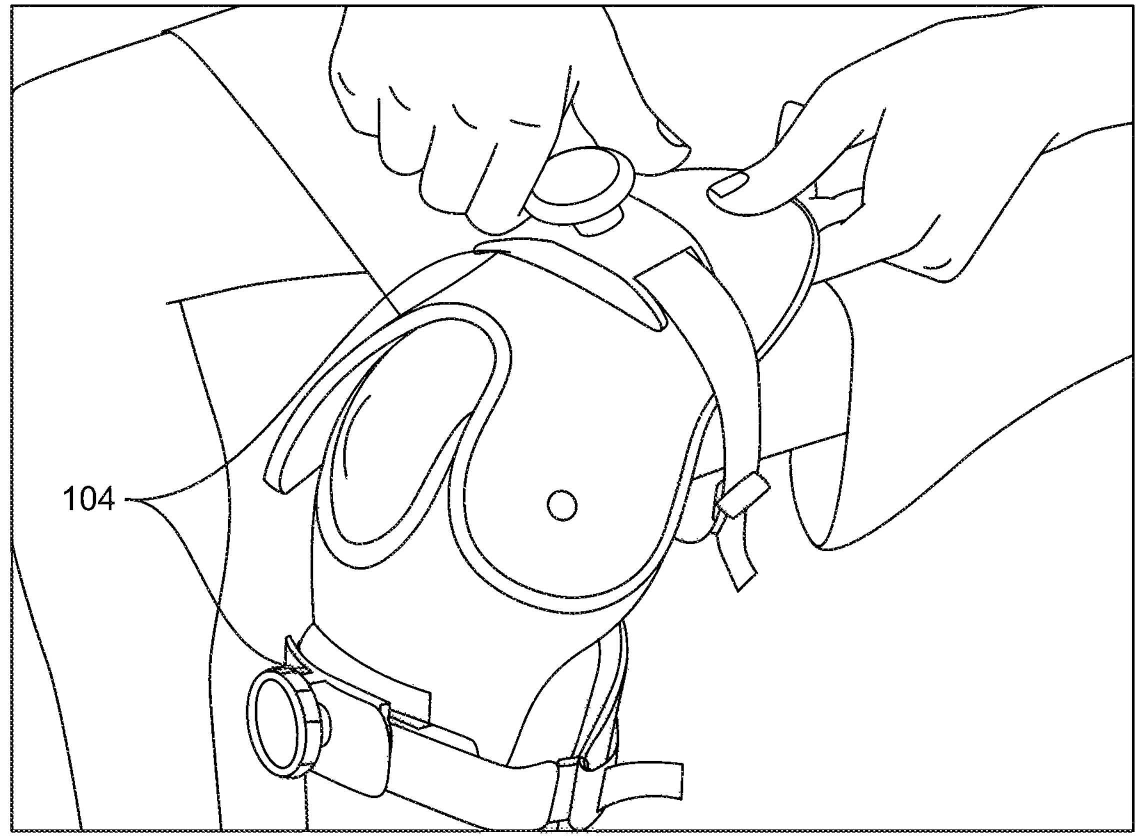
FIG. 55 illustrates a garment fastening system applied to a garment and a leg.

FIG. 55 shows upper and lower attachment systems 104 that can be used to secure the any of the garments, garment assemblies, or strap assemblies disclosed herein to the user's leg or other body part. The attachment system 104 may include a magnetic securement and adjustment system therein. The attachment system 104 includes a mechanical latch or securement system and magnets for aligning the components to make connection easier. For example, a Fidlock magnetic buckle or system can be used.

Figure 56:
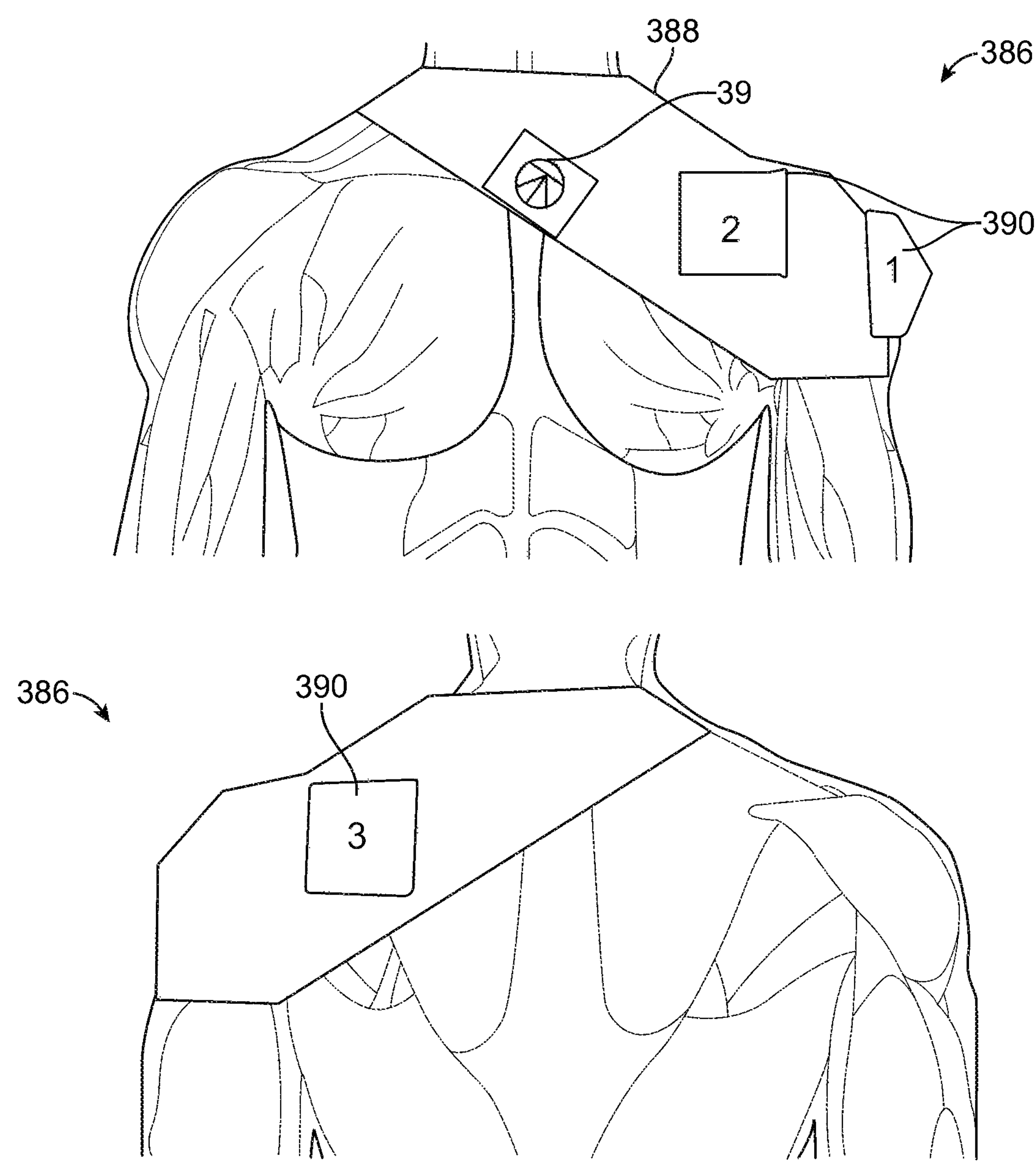
FIG. 56 illustrates front and back views of an individual wearing a therapeutic shoulder strap.

FIG. 56 shows front and back views of the shoulder strap assembly 386. As shown, the shoulder strap assembly 386 is a battery powered wearable that can replace ice packs and is shaped to treat the shoulder and upper back. The assembly 386 can also be used for heat therapy and may have several vibration motors embedded in the strap or garment to boost blood flow and recovery. In the illustrated embodiment, the shoulder strap assembly 386 includes a removable battery and controller 396, at least three temperature control modules 390, and optionally vibration motors embedded in the garment or strap. When included, the embedded vibration motors may be present in a quantity of, for example, six to twelve. The vibration motors may be divided into groups of three and the speed or activation state of the groups can be controlled independently from one another. The assembly 386 may also include Bluetooth connectivity that allows it to be connected to an app on a mobile device. Exemplary use cases for athletes and non-athletes include post shoulder surgery treatment, post work-out recovery, and users with chronic shoulder, neck and upper back pain.

The shoulder strap assembly 386 includes a garment portion or strap portion 88 and temperature control modules 390. The temperature control module 390 can be any of the temperature control modules (e.g., 14, 114, 234, 366, and 368) shown and described herein. Thus, the temperature control module 390 includes a contact, a fan, a heat sink, and a thermal element such as a Peltier device configured to heat or cool the contact.

Because the body parts that any of the foregoing garments, garment assemblies, straps, and strap assemblies may be used on include curved surfaces, they may benefit from use temperature control modules 14, 114, 234, 366, 368, 390 with contacts that include extension members or spreaders, such as finger spreaders 42, 142, that essentially increase the footprint of the contacts and allow devices according to this aspect of the present disclosure to distribute the desired temperature around curved areas in the body such as, for example, the calf, shoulder, or trapezoid. The treatment area beyond the footprint of the Peltier device to the spreaders may have a small temperature gradient, such as a 2-3° C. difference.

The finger spreaders 42, 142 may act as modular extension legs or extension members of the contact of a given temperature control module 14, 114, 234, 314, 366, 368, 390. As noted above, the contacts, including main spreaders 40, 140 and finger spreaders 42, 142 may be made of, for example, stacks of thin copper. The spreaders can be divided into smaller fingers to add flexibility in the perpendicular direction and help adapting to the body. The finger spreaders can be attached to the main spreader under the primary spreader by different methods, such as, for example, being bolted or otherwise threadedly fastened, riveted, welded, or otherwise.

Figure 57:
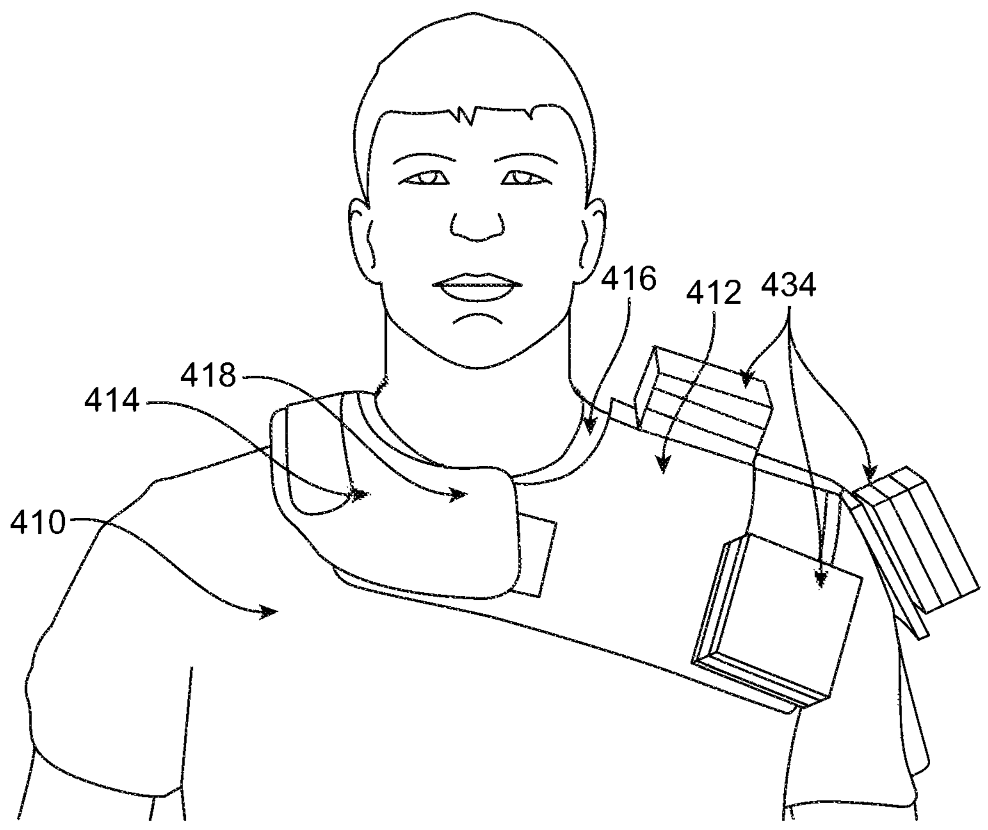
FIG. 57 illustrates an individual wearing a therapeutic shoulder strap according to another arrangement.
Figure 58:
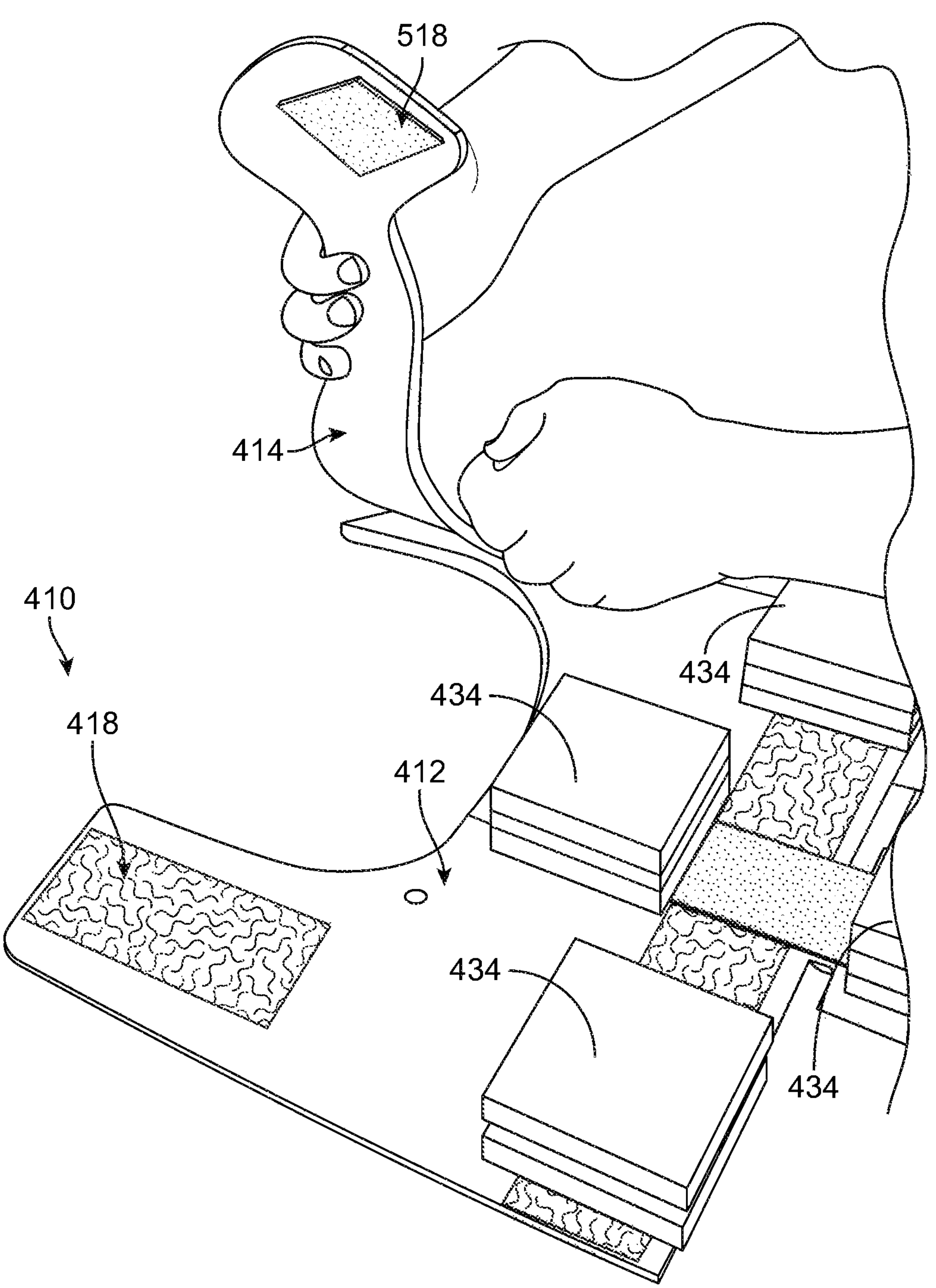
FIG. 58 illustrates the therapeutic shoulder strap of FIG. 57 in a partially disassembled state.

As shown in FIGS. 57 and 58, the strap assembly 410 includes first and second strap members 412 and 414 that cooperate to define a neck opening 416 when they are secured together. The first strap member 412 includes the temperature control modules thereon. The second strap member 414 is removably secured to the first strap member 412 at both ends. This allows the user to adjust the size of the neck opening 416 and where the temperature control modules 434 are positioned on their shoulder. Temperature control modules 434 are any of the other temperature control modules discussed herein, including temperature control modules 14, 114, 234, 314, 366, 368, 334, 390. The first and second strap members can be connected via any releasable system that allows the strap members to be separated. In some embodiments, the first and second strap members include complementary securement members 418 (also referred to as "adjustable element" in FIG. 57). FIGS. 57 and 58 show hook and loop material as the securement members 418, though other securement members such as buckles, buttons, or pins may be used in other examples. However, any type of securement members or attachment system is within the scope of the present disclosure. For example, magnets, straps, snaps, clasps or the like can be used.

In use, the user can put the strap assembly 410 on by placing their head through the neck opening 416 and without having to slide an arm through an opening. In another embodiment, an arm opening can be included. The weight of the temperature control modules 434 helps maintain the first strap member and the heated or cooled surface of the cold/heat module close to the body. With the arrangement of modules shown in FIG. 58, the strap assembly treats the several muscles in the shoulder joint (pectoral, deltoid, trapezoid, dorsi), but is symmetrical and/or reversible and can be used on the left and right shoulders.

Figure 59:
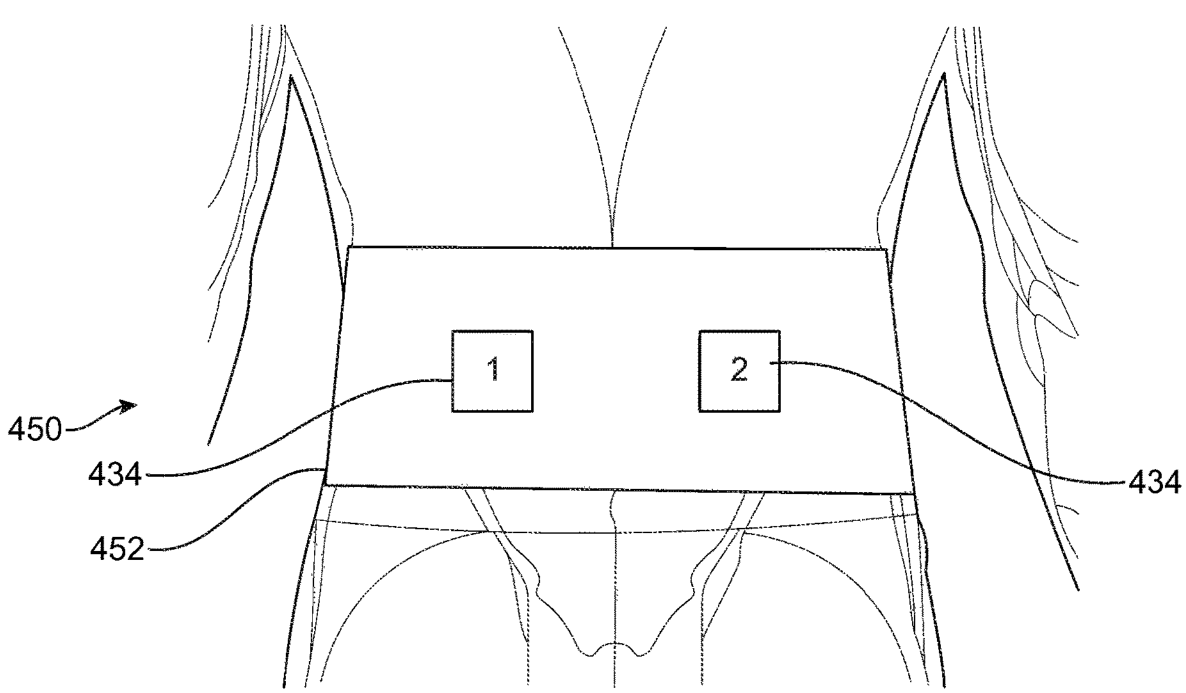
FIG. 59 illustrates an individual wearing a therapeutic strap assembly.

FIGS. 59-62 show a strap assembly 450 similar to strap assembly 10 above, but designed for use on a user's torso, or more specifically a user's lower back as shown in FIG. 59. Strap assembly 450 includes features that help hold the hot or cold contact surfaces of the temperature control modules 434, such as the main spreader 40, 140 and the finger spreaders 42, 142 against the user's skin while the strap is worn. The finger spreaders 42, 142 as applied in the example of FIGS. 59-62 will hereinafter be referred to with numeral 442, though they may be any of the finger spreaders 42, 142 discussed or illustrated elsewhere in this application. The surface of the skin of a user is not flat, but includes undulations and changing surfaces. Therefore, straps, bands or the like for holding or pushing the main spreaders 40, 140 and finger spreaders 442 against the user's skin can be helpful. In some embodiments, the strap assembly 450 includes a removable battery pack associated with the temperature control module 454 and configured to supply power to the temperature control module 454. In some embodiments, the removable battery pack in the strap assembly 450 may generally be similar to any of the battery embodiments described herein. In some embodiments, the strap assembly 450 may be washable and may include at least some components that are embedded in or attached permanently in the strap assembly 450 (e.g., waterproof enclosed motors, cabling, etc.) and other components that are removable (e.g., battery pack, PCB). In some embodiments, the permanent components may be sealed in the strap assembly 450 (e.g., between garment layers and the user can wash the strap assembly 450 after removing the control module and/or power supply components (battery pack, PCB, etc.).

The "double strap" features discussed herein, referring to the use of a primary strap to secure a therapeutic garment in place and one or more secondary straps connected to the primary strap to press the temperature control modules against the wearer, can apply to any of the strap assemblies disclosed herein. For example, the broken lines in FIG. 13 may represent the secondary strap 456.

The strap assembly 450 includes straps that serve two different purposes: a primary strap 452 for securing the strap assembly 450 to the user's body/body parts (a lower back strap is shown in FIGS. 59-62) and one or more secondary straps 456 that operate to hold, compress or secure the temperature control modules, and the spreaders and finger spreaders 442 thereof, against the user's skin. Stated another way, the primary strap 452 can be used hold the temperature control module 434 generally in place relative to the wearer such that a contact portion of the temperature control module 434, including the main spreader 40, 140 and any finger spreaders 442 or other extensions, is in contact with or at least positioned near a portion of the wearer intended to be heated or cooled, and the secondary straps 456 can be used to supplement or adjust an amount of pressure between the contact portion of the temperature control module 434 and the wearer's skin. The strap assembly 450 may also include a control module or control assembly 473, generally alike to the control assemblies 373 or other types of controllers described above. Optionally, the primary strap 452 may include a socket in which the control assembly 473 may be installed as shown in the illustrated example.

To enable securing the strap assembly 450 to the wearer, the primary strap 456 may include fasteners or other features that enable two attachable portions of the primary strap 452 to be releasably connected to one another to form the primary strap 452 into a loop. Thus, strap assembly 450 can be secured to a wearer by wrapping the primary strap 452 about wearer's torso and connected the two attachable portions of the primary strap 452 together, thereby closing the loop around the wearer. Disconnecting the attachable portions of the primary strap 452 thereafter enables the strap assembly to be easily removed.

In the illustrated example, the two attachable portions of the primary strap 452 are ends 451*a*, 451*b* of primary straps 452. Further according to the illustrated example, the ends 451*a*, 451*b* are provided with fasteners in the form of a patch of hook material 454*a* at one end 451*a* and a patch of loop material 454*b* at the other end 451*b* to enable fastening the ends 451*a*, 451*b* together with a hook and loop connection. The ends 451*a*, 451*b* may each have patches of hook and loop material on both sides, or the patch of hook material 454*a* may be on a reverse side of the primary strap 452 from the loop material 454*b* so that the hook and loop patches 454*a*, 454*b* will come into contact when the primary strap 452 is wrapped into a loop with the ends 451*a*, 451*b* overlying one another. In other examples, the primary strap 452 may be provided with fasteners other than the hook and loop patches 454*a*, 454*b*, such as, for example, a buckle at one end 451*a*, 451*b*, a pin or hook engageable to holes in both ends 451*a*, 451*b*, or tethers connected to the ends 451*a*, 451*b* that may be tied together. In other examples, the ends 451*a*, 451*b* may be long enough and flexible enough to be tied together themselves. In yet other examples, the primary strap 452 may be a single continuous loop of material that is otherwise securable to and removable from the wearer. For example, the primary strap 452 may be a large band of elastic material that can be stretched as the wearer dons or removes the strap assembly 450.

Secondary straps 456 of the illustrated example are connected to the primary strap 452 by being disposed through respective tunnels 460 defined in the primary strap 452. In other examples, the secondary straps 456 may be additionally or alternatively connected near their respective midpoints to the primary strap in any other way such as, for example, by being sewn to the primary strap 452, or buttoned or otherwise releasably fastened to the primary strap 452. Each secondary strap 456 may be, for example, an elastic band or the like. Each end of each secondary strap 456 may also include patches of hook material, loop material, or both hook and loop material capable of fastening to the patches of loop material 454*a*, 454*b* of the primary strap 452, or other fasteners for securing the secondary straps 456 to a portion of the primary strap 452.

Figure 60:
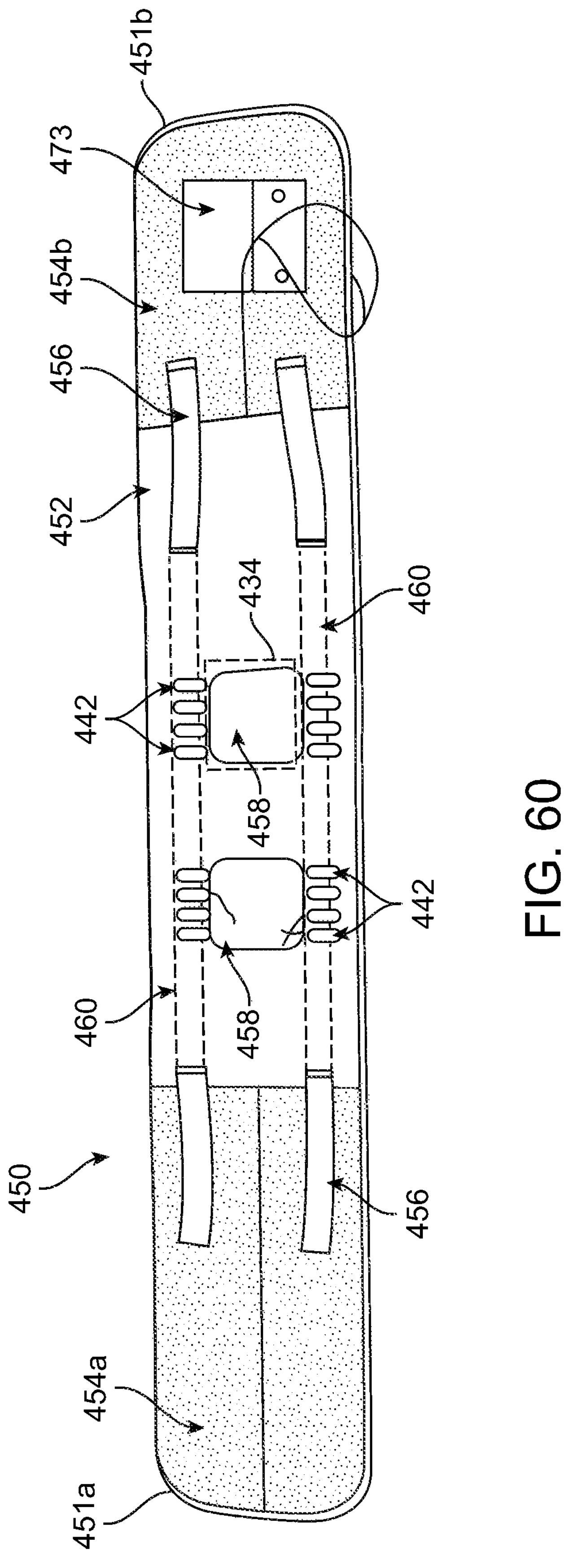
FIG. 60 illustrates the therapeutic strap assembly of FIG. 59 in an unwrapped state.
Figure 61:
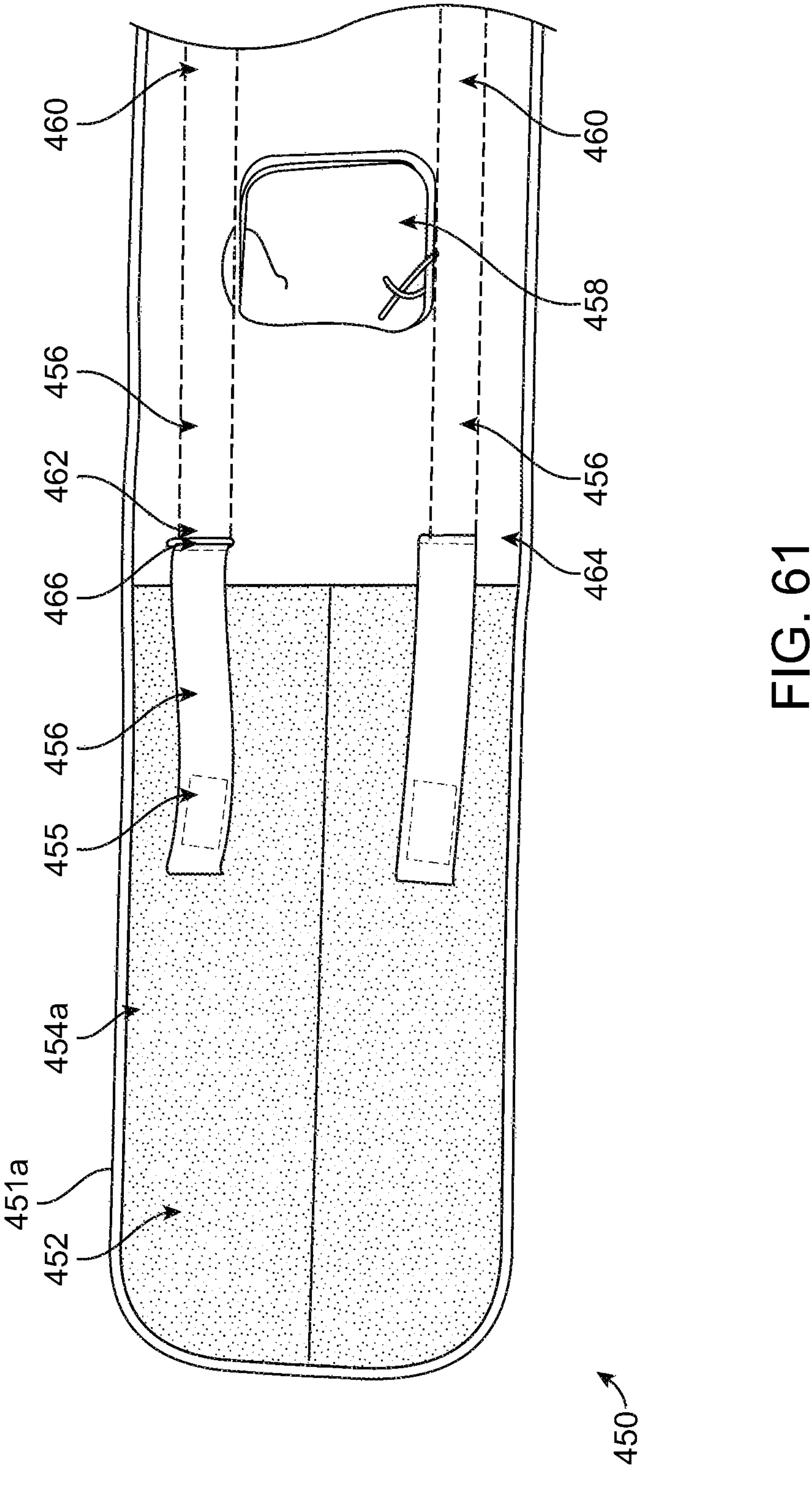
FIG. 61 illustrates an end portion of the therapeutic strap assembly of FIG. 59.
Figure 62:
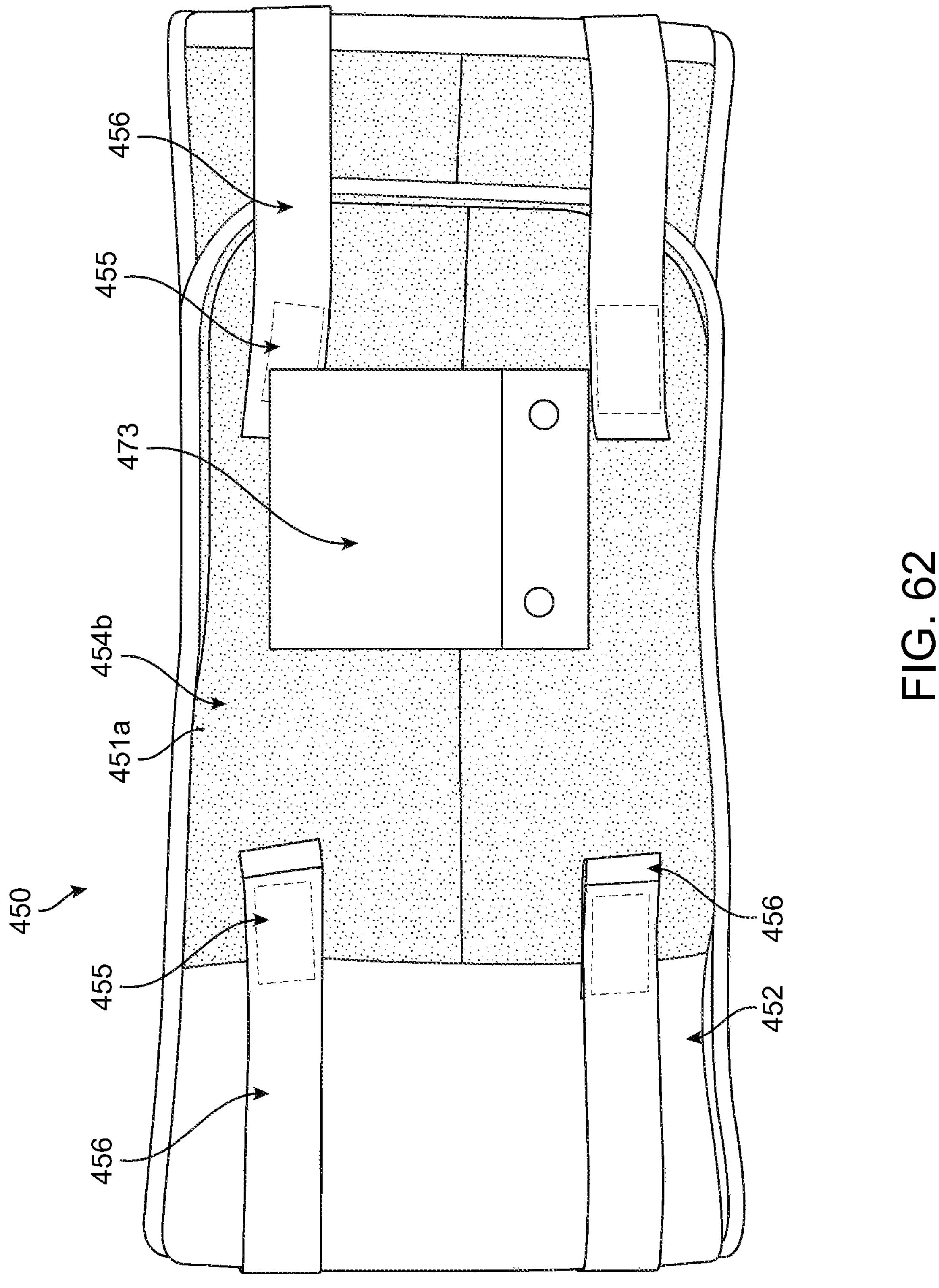
FIG. 62 illustrates the therapeutic strap assembly of FIG. 59 in a wrapped state.

As shown in FIGS. 59-62, each of the secondary straps 456 extend through a respective tunnel 460 or space formed between two layers or portions of the first strap 452. The tunnels 460 extend along at least a portion of a length of the primary strap 452. The secondary straps 456 enter the tunnels 460 through openings 462 in the outer layer 464 and include stop members 466 that prevent the loose ends of the secondary strap 456 from entering the opening 462. Within the tunnel 460, the secondary straps 456 overlap or extend over the back surface of the finger spreaders 442, as shown in FIG. 60. FIG. 62 shows the strap assembly 450 in the closed positioned where the hook and loop material 454 is secured as it would be around a user's torso. In use, after securing the first strap 452 around the torso, the user pulls on the loose or distal ends of the secondary straps 454 to compress the finger spreaders 442 against the user's back and secures the hook and loop material 455 on the secondary strap 454 to the hook and loop material 454*a* or 454*b* on the first strap 452. In some examples, the secondary straps 456 may be elastic enough to enable opposite ends of a single secondary strap 456 secured to one another by the hook and loop material 455. In further examples, the ends of the secondary straps 456 may include other fasteners than the hook and loop material 455 instead or in addition to the hook and loop material 455, and such other fasteners may be suitable for securing the end of the secondary straps 456 to either or both of corresponding fasteners on the primary strap 452 and an opposite end of the same secondary strap 456.

In the illustrated example, when the temperature control module 434 is received in the opening 458, the finger spreaders 442 extend transverse to the length and the thickness of the primary strap 452 so as to extend across the tunnels 460 so that constriction of the secondary straps 456 about the wearer will cause the secondary straps 456 to press directly onto to the finger spreaders 442, improving contact between the finger spreaders 442 and the wearer. As shown above, temperature control modules may be constructed with spreaders 442 in any of a wide variety of configurations, so temperature control modules may be installed in the strap assembly 450 with spreaders 442 extending across either or both of the tunnels 460. In some examples, including the illustrated example, when the temperature control module 434 is installed through the opening 458, the spreaders 442 may extend transverse to the length and the thickness of the primary strap 452 so that a total width of the contact portion of the temperature control module 434, which includes all spreaders, 40 or 140 and 442, of the temperature control module 434, exceeds a distance between the tunnels 460 across the opening 458. In such examples, the contact portion of the temperature control module 434 includes laterally extending spreaders that extend across both tunnels 460. Temperature control modules 434 may optionally include vibration motors so that the strap assembly 450 may provide vibration therapy to the wearer. In further examples, vibration motors such as vibration devices 70 described above may optionally be integrated in the primary strap 452, secondary straps 456, or both to enable the strap assembly 450 to provide vibration therapy to the wearer.

As described above, the finger spreaders 442 may be movably connected to a remainder, or hub portion, of the temperature control module 434. In the foregoing examples such movable connections include both mechanical hinges formed by respectively pivoting parts and living hinges formed by flexible material, and the spreaders 442 may be biased either by external springs or internal resilience to resting positions extending downward, or generally away from the heat sink or corresponding features of the temperature control module 434. Thus, when a temperature control module 434 according to such examples is installed in the opening 458 and the strap assembly 450 is worn, the spreaders 442 are biased both toward the user and away from a user-facing side of the primary strap 456. The bias on the spreaders 442 therefore cooperates with the secondary straps to increase the pressure of the contact portion of the temperature control module 434 on the wearer.

The secondary straps 456 may be more elastic than the primary strap 452 to facilitate providing a static load to the wearer. While the primary strap 452 holds the strap assembly 450 on the wearer, the secondary straps 456 apply pressure between the spreaders 40, 140, 442 and the wearer can be adjusted by stretching the secondary straps 456 by greater or lesser amounts before securing the ends of the secondary straps 456 to the primary strap 452 or to each other. The secondary straps 456 may be shorter in all dimensions than the primary strap 452 so that the secondary straps 456 can be stretched by an amount that is significant in proportion to their resting length without being as long as, or significantly long than, the length of the primary strap 452. In addition to having a greater elasticity than the primary strap 452, the secondary straps 456 may optionally also have a lower spring constant than the primary strap 452 to facilitate stretching the secondary straps 456 to a desired length.

In another arrangement, the primary strap 452 may include finger spreaders, similar to the finger spreaders 442 of the temperature control module 434, integrated into the primary strap 452 on the surface of the primary strap 452 intended to face the wearer at the locations where the finger spreaders 442 are shown in the illustrated examples. The elements labeled 442 in FIG. 60 should therefore be interpreted as indicating both where finger spreaders of temperature control modules 434 may lie when temperature control modules 434 are installed in the openings 458 in the above described examples and where, in examples including finger spreaders integrated into the primary strap, where such integrated finger spreaders may be located on the wearer facing surface of the primary strap 450. Each such integrated finger spreader would therefore be located proximate one of the openings 458 and, when the strap assembly 450 is worn, between one of the tunnels 460 and the wearer. The secondary straps 456 would therefore press the integrated finger spreaders against the wearer in the same way that the secondary straps 456 press the finger spreaders 442 of the temperature control modules 434 against the wearer as described above. Moreover, such integrated finger spreaders may extend into the openings 458 or otherwise be accessible from the peripheries of the openings 458 to interface with temperature control modules that may be installed in the openings 458. In the same manner that the thermal control modules disclosed herein may be provided with any of a wide variety of finger spreader arrangements in addition to those specifically illustrated, the integrated finger spreaders may also vary in quantity, size, shape, and angle.

Figure 63:
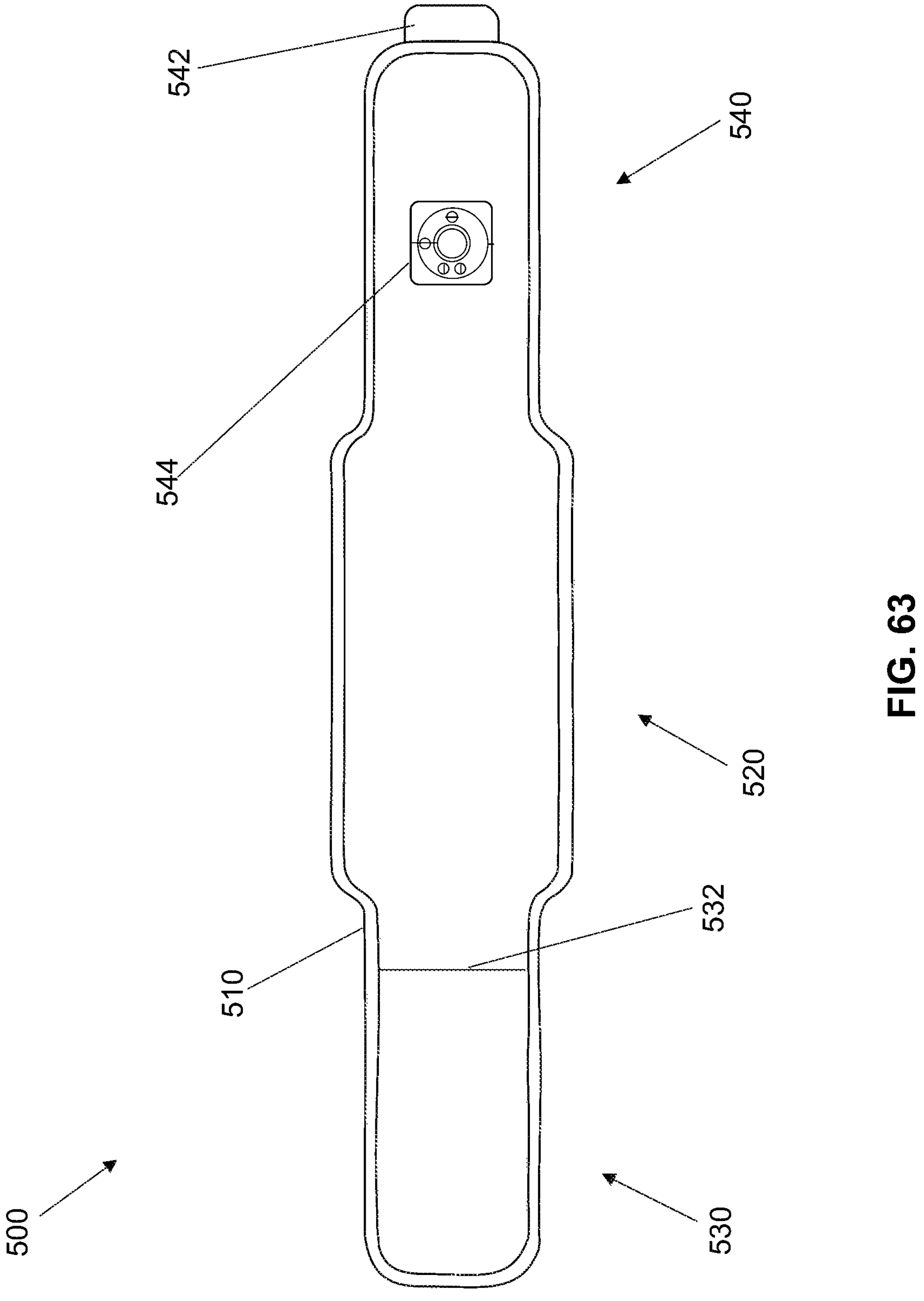
FIG. 63 is a rear elevation view of a therapeutic device according to another arrangement.

FIGS. 63-66 illustrate a therapeutic device 500 according to another embodiment. As shown in FIG. 63, the device 500 includes a strap 510 and a control module 544 mounted to the strap. The strap 510 includes a middle portion 520, a first end portion 530 extending from the middle portion 520, and a second end portion 540 extending from an opposite side of the middle portion 520 as the first end portion 530. In the illustrated example, the middle portion 520 is wider than the end portions 530, 540, though in various other examples the end portions 530, 540 and middle portion 520 can be of any width relative to one another.

The control module 544 includes a user interface to allow for control of the device 500, which may be provided by buttons and indicator lights as shown or, in other examples, by a touch screen or any other features with which a user may interact. The control module 544 also houses electronic elements for the control and operation of the device 500. The control module 544 may optionally include a connection through which external power can be supplied to device 500 and a battery, though either or both of the power supply and battery may be located elsewhere on the device 500 or omitted altogether. In some embodiments, the control module 544 may include a slot or opening, in which a removable battery may be inserted to supply power to the therapeutic device 500. In some embodiments, the removable battery in the control module 544 may generally be similar to any of the battery embodiments described herein. In the illustrated example, the control module 544 is located on the second end portion 540 of the strap 510, but in other examples the control module 544 may be located anywhere else on the strap 510, divided into multiple distributed modules at any locations on the strap 510, or omitted altogether. In examples wherein the control module 544 is omitted altogether, the electronic components of the device 500 may be integrated into the strap 510 and the device 500 may be controlled remotely or wirelessly with an external device, such as a smart device or computer. In some embodiments, the therapeutic device 500 may be washable and may include one or more components that are removable and/or one or more components that are attached permanently in the strap 510.

Figure 64B:
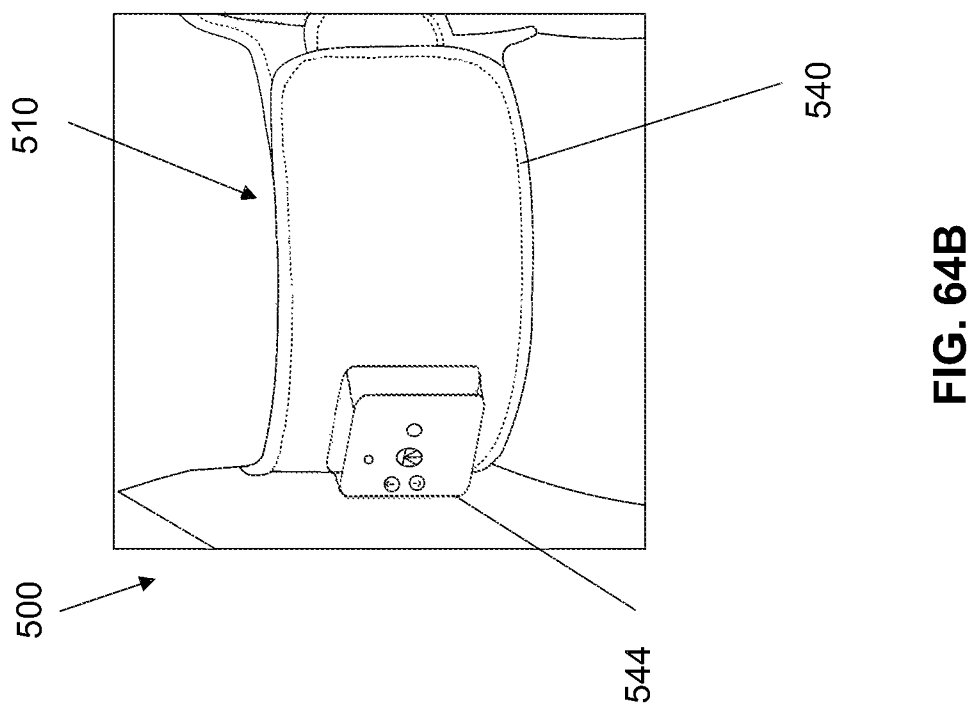
FIG. 64B is a front perspective view of the therapeutic device of FIG. 63 worn by the user.
Figure 64A:
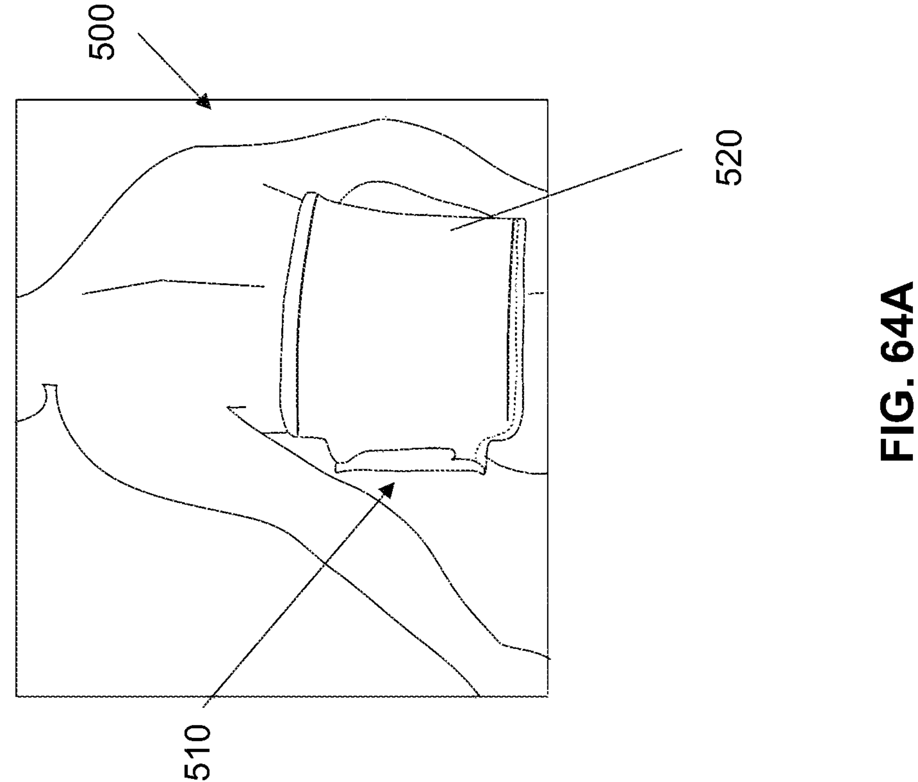
FIG. 64A is a rear perspective view of the therapeutic device of FIG. 63 worn by a user.

FIG. 63 illustrates a side of the therapeutic device 500 intended to face away from a wearer. The device 500 can be worn with the middle portion 520 of the strap 510 placed on the wearer's middle to lower back, as shown in FIG. 64A, and with the first end placed 530 against the wearer's stomach and overlapped by the second end 540, as shown in FIG. 64B. When the device 500 is worn as shown in FIGS.

64A and 64B, the user interface of the control module 544 faces outward and is readily accessible to the wearer.

In the illustrated example, the strap 510 includes a hook and loop patch 532 attached on the outward side of the first end portion 530, as shown in FIG. 63, for fastening to a complementary hook and loop patch, not illustrated, attached on an inward side of the second end portion 540. Thus, a wearer can easily and adjustably fasten the device 500 as shown in FIGS. 64A and 64B by pressing the outer strap 540 over the inner strap 530. The strap 510 of the illustrated example further includes a tab 542 extending from the second end portion 540 to facilitate adjusting and releasing the hook and loop connection. Hook and loop patches are only one example of a suitable type of fastener, and in other examples, the strap 510 can have any other fasteners, such as, for example, a buckle, zipper, buttons, or the secondary straps 456 and tunnels 460 described above, instead of or in addition to the hook and loop patches. The tab 542 may optionally be omitted or included in any such variations of the strap 510.

Figure 65:
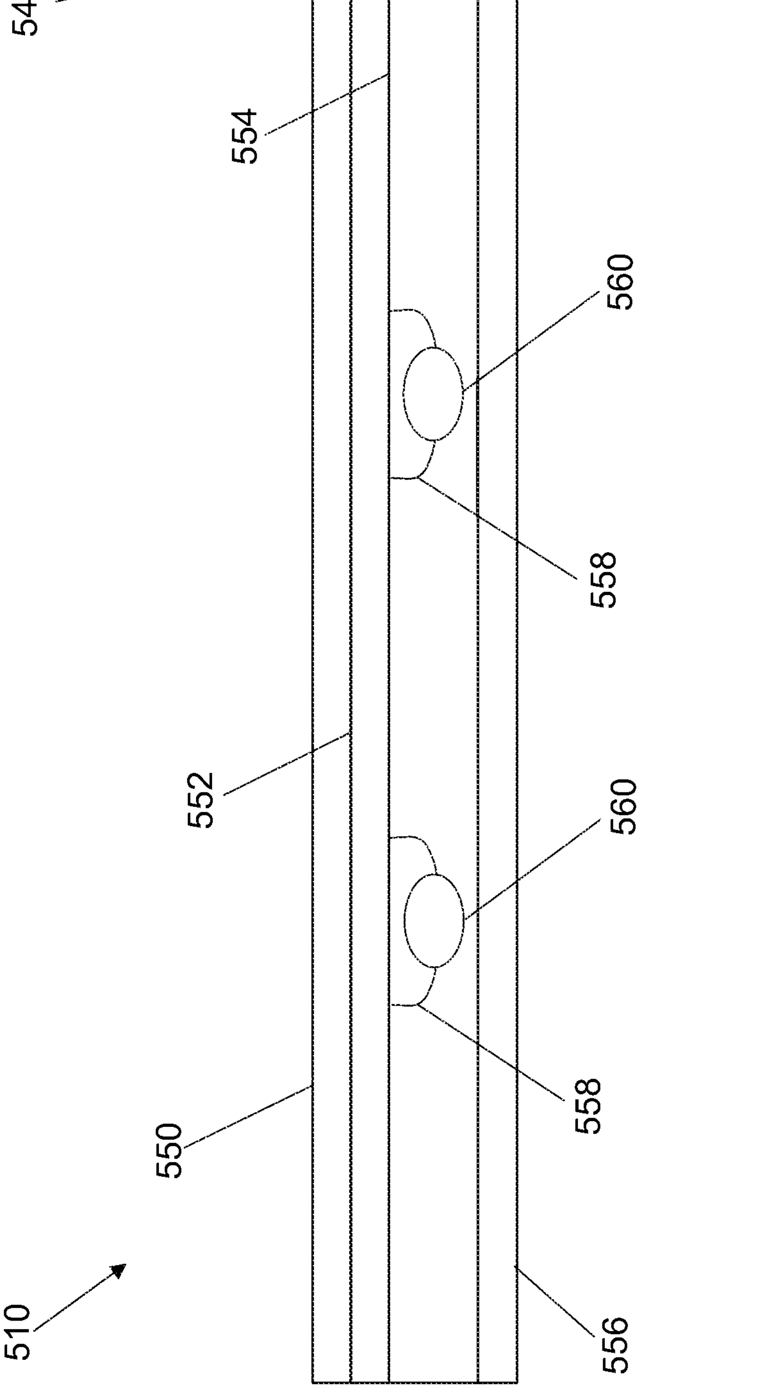
FIG. 65 is a cross-section of a portion of the therapeutic device of FIG. 63.

FIG. 65 shows a cross-section of the middle portion 520 of the strap 510 on a plane parallel to the perspective of FIG. 63. The strap 510 includes an outer layer 550, intended to face away from a wearer, an inner layer 556, intended to contact the wearer, and a padding layer 554 located between the outer layer 550 and inner layer 556. The outer layer 550 can be any suitably flexible and durable material or fabric, with neoprene being one example. In further examples, the outer layer 550 may be any one or any combination of neoprene, lycra, styrene butadiene rubber, and any similar materials in combination, woven or knitted fabric, or individual layers.

The padding layer 554 may be a cushion, a polymer foam, or any other resiliently compressible material that makes the strap 510 comfortable for a wearer. A layer of fabric may optionally be bonded or sewn to an inner side of the padding layer 554, an outer side of the padding layer 554, or both.

The inner layer 556 of the illustrated example is a knitted fabric including germanium yarn, individual fibers made of germanium or germanium alloy, or yarns otherwise infused with germanium. The knitted fabric may specifically include germanium or germanium alloys in such states and compositions that passively emit infrared radiation, or more specifically far-infrared radiation, to provide infrared radiation therapy to the wearer. One example of a suitable alloy is an alloy of germanium with titanium. The knitted fabric may also include polymer or organic yarn or fibers interwoven with the germanium yarn or fibers in any proportion. In other examples, the inner layer 556 may be a fabric without any germanium content, or any of the materials suitable for the outer layer 550 with or without the addition of germanium or germanium alloy. In other examples, the inner layer 556 may include other materials that passively emit infrared radiation instead of or in addition to germanium. Other examples of materials that could be included in the inner layer 556 to cause the inner layer 556 to passively emit infrared radiation include sericite mineral, such as fine grained mica, or nanoparticles of infrared or far-infrared radiation emitting ceramics. In other examples, the germanium or other infrared emitting material may be included within the inner layer 556 in the form of solid plates or rods rather than in yarn within a knitted fabric. In further examples, the inner layer 556 or another part of device 500 includes an active infrared radiation emitter, such as an infrared light emitting diode or another electrically powered emitter, instead of or in addition to passive infrared emitting materials.

Germanium fabric, as well as the other examples of infrared emitting material described above with respect to the inner layer 556, reflect the heat and radiation from the wearer's body back toward the wearer, thereby improving the therapeutic effect of the device 500 by promoting temperature control, blood circulation, muscle relaxation, and other benefits associated with infrared and heat therapy. As one example, germanium embedded fabric with an emission power of 3.53×102 W/m$^2$ (35.3 mW/cm2) over the 5-20 μm wavelength range and emissivity of 0.874 has been found effective for providing the foregoing therapeutic benefits, but the emission power, wavelength range, and emissivity could vary above or below those values and still have similar effects on the wearer. Increasing the proportion of germanium in the fabric will tend to increase the reflective and emissive efficacy of the fabric while decreasing the flexibility of the fabric, so the amount of germanium can be varied to achieve different criteria with various articles according to the concepts of the present disclosure. In another example, fabric compositions of 15 mg, or about 15 mg, of pure germanium per kilogram of fabric have been found effective for providing the above mentioned therapeutic benefits without making the device 500 too stiff to wear comfortably, but the proportion of germanium in the fabric can vary in other examples.

The strap 510 also includes a layer of carbon fiber 552 located inward from the outer layer 550. The carbon fiber 552 may be, in various examples, a continuous sheet or a mesh. Whether provided in a continuous sheet or mesh, the carbon fiber 552 may be relatively thin and therefore pliable enough that the portions of the strap 510 containing carbon fiber 552 are flexible. The carbon fiber 552 is connected to a power source, which may be housed in the control module 544 or otherwise mounted to the strap 510, to act as a heating element. That is, the carbon fiber 552 is an in-line resistor in an electrical circuit built into the device 500 and therefore generates heat resistively when the circuit is active. Skin temperatures equal to or slightly above 42° C. result in useful therapeutic effects, such as muscle relaxation and improved blood flow, while skin temperatures greater than 45° C. can be uncomfortable. Thus, the circuit and carbon fiber 552 may be configured to generate enough heat to bring skin contacting the inner layer 556 to, in various examples, 42° C., at least 42° C., or in a range from 42° C. to 45° C. Because the strap 510 can be constructed with a variety of materials and thicknesses for each layer, the heating capacity of the circuit and carbon fiber 552 may vary among different implementations of the device 500 as appropriate to heat a wearer's skin to the foregoing temperatures through any layers 554, 556 located inward of the carbon fiber 552. The device 500 may optionally be controllable, such as through control module 544 or an external device, to adjust the carbon fiber's 552 heat output, and the device 500 may optionally include a thermostat for maintaining the carbon fiber 552 or inner layer 556 at an intended temperature. In various examples, the device 500 may be configured to allow temperature adjustment only within a range of temperatures corresponding to a wearer's skin being from 42° C. to 45° C., or the device 500 may allow adjustment above, below, or above and below that range of temperatures. Further, carbon fiber 552 is only one example of a type of heating element that device 500 may include. In other examples, the device 500 may include any kind of heating element capable of safely heating the wearer's skin to between 42° C. and 45° C. instead of or in addition to carbon fiber 552 and located in or on the strap 510.

The device 500 includes embedded motors 560 that vibrate to provide therapeutic effects to a wearer, such as improved blood flow and muscle relaxation. Thus, the motors 560 can operate in cooperation with the strap's 510 heating capabilities to relieve tension and promote recovery. The motors 560 may be placed at any location relative to the other layers of the strap 510 shown in FIG. 65, but the illustrated placement of the motors 560 inward of the outer layer 550 and carbon fiber 552 and outward of at least a portion of the padding layer 556 gives the strap 510 an appealing form factor while cushioning the wearer from the vibration of the motors 560. The strap 510 also includes pads 558, which may be made of any of the materials from which padding layer 556 may be made, located between the motors 560 and the carbon fiber 552. The pads 558 protects the carbon fiber 552 from direct impact by the vibrating motors 560 and thereby reduces the propensity of the device 510 to rattle when the motors 560 run. The motors 560 may optionally be housed in a compartment made of additional carbon fiber on at least a side that faces away from the wearer and toward the pads 558.

Figure 66:
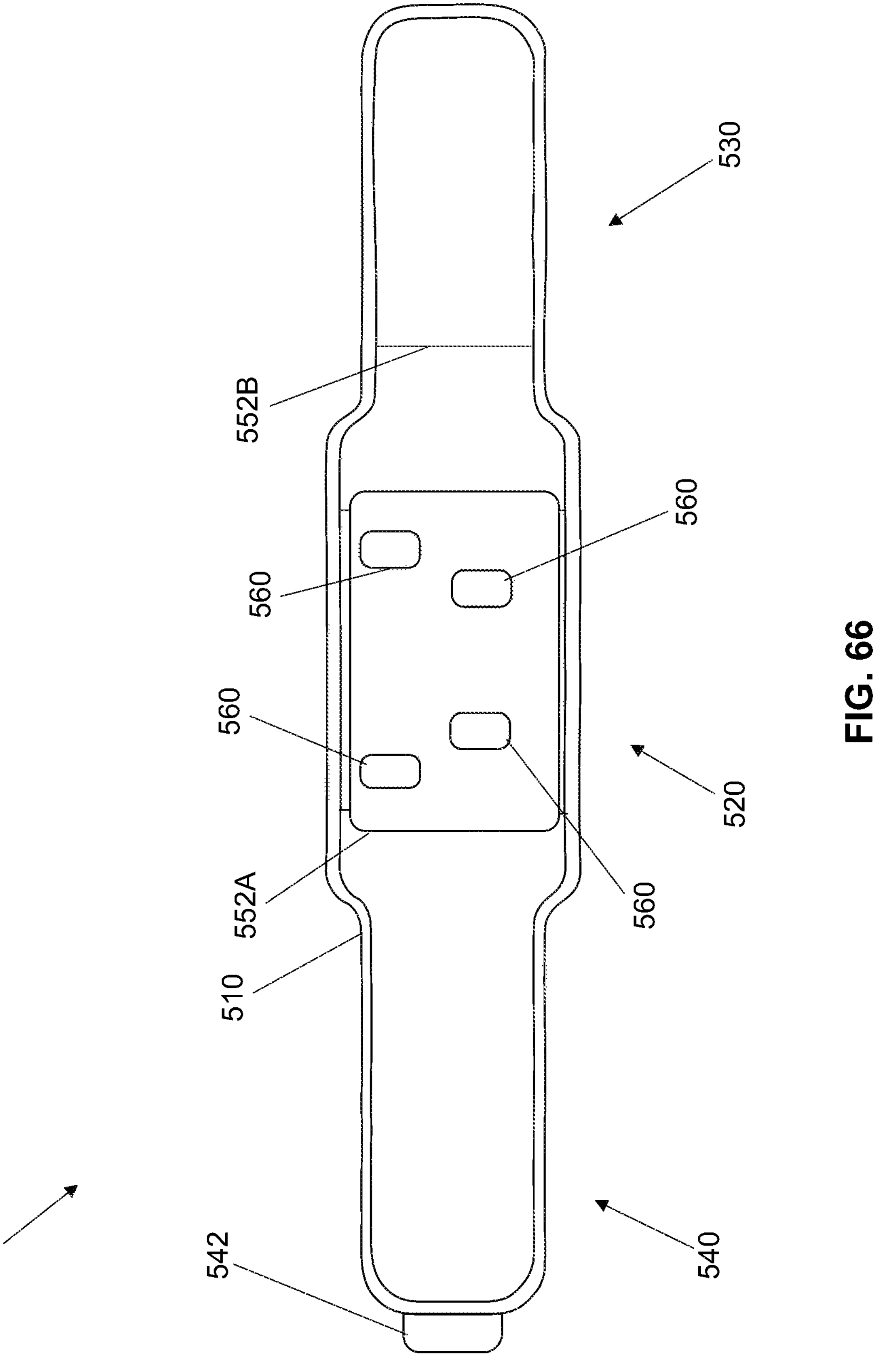
FIG. 66 is a front elevation view of a portion of the device of FIG. 63.

FIG. 66 illustrates a portion 500' of the device 500 from a perspective opposite from the perspective of FIG. 63. The portion 500' lacks the inner layer 556, padding layer 554, and pads 558 for illustrative purposes, though the inner layer 556 and padding layer 554 may be entirely or nearly entirely (meaning except for at hems, seams, or both) coextensive with the outer layer 550 in a fully assembled device 500. As shown in FIG. 66, the carbon fiber 552 is provided in two distinct panels, namely, a back panel 552A and a front panel 552B. The back panel 552A is located in the middle portion 520 of the strap 510 and is therefore positioned to effectively heat the wearer's back when the device 500 is worn as shown in FIGS. 64A and 64B. Similarly, the front panel 552B is located in the first end portion 530 and is therefore positioned to effectively heat the wearer's front when the device 500 is worn as shown in FIGS. 64A and 64B. The gap between the back panel 552A and front panel 552B reduces the total area of the carbon fiber 552, and by extension the overall power consumption of the heating function of the device 500. Moreover, the gap between the back panel 552A and front panel 552B contributes to the flexibility and durability of the strap 510 by leaving the portion of the strap 510 where the first end portion 530 meets the middle portion 520, which is where the strap 510 is likely to be folded to a relatively small radius of curvature when worn, free of carbon fiber 522. However, in other examples, a single continuous panel of carbon fiber 552 may extend from the middle portion 520 to the first end portion 530 to heat the wearer's back and stomach. Though there is no carbon fiber 552 or other heating element in the second end portion 540 of the strap 510 in the illustrated example, carbon fiber 552 or another heating element may be added to the second end portion 540 instead of or in addition to the carbon fiber 552 in the first end portion 530 in other examples. The carbon fiber 552 added to the second end portion 540 may be another distinct panel or may extend from the back panel 55A.

As shown in FIG. 66, motors 560 are located in the middle portion 520 of strap 510 to provide vibration therapy to a wearer's back. The motors 560 are offset symmetrically to either lateral side of the center of the middle portion 520 to avoid vibrating against the wearer's spine or other bones and to affect the muscles to either side of the spine. The motors 560 overlap the back panel 552A of the carbon fiber 552, meaning the device 500 can provide heat and vibration therapy to the same point on a wearer's body. In other examples, the device 500 may have motors 560 located away from the carbon fiber 522.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present disclosure. Other measurements or dimensions are within the scope of the disclosure.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although certain concepts according to the present disclosure have been shown and described, it is to be understood that all the terms used herein are descriptive rather than limiting, and that many changes, modifications, and substitutions may be made by one having ordinary skill in the art without departing from the spirit and scope of the disclosure.

What is claimed is:

1. A wearable assembly, comprising:
- a temperature control module comprising a contact and a thermal element configured to heat or cool the contact;
- a removable battery associated with the temperature control module;
- a primary strap configured to receive the temperature control module and secure the contact against a subject; and
- a secondary strap configured to be connected to the primary strap and further configured to provide adjustment of a pressure between the contact and the subject when the primary strap secures the contact to the subject, wherein the contact of the temperature control module comprises:
- a main contact body, on a first surface of which the thermal element is disposed; and
- a plurality of contact fingers configured to extend outwardly from the first surface of the main contact body in a circumferential direction when the wearable assembly is secured to the subject, wherein the plurality of contact fingers extend away from the main contact body at an edge of the main contact body, and wherein the plurality of contact fingers and the edge of the main contact body form a pivotable connection such that the plurality of contact fingers are hingedly attached to the main contact body, and wherein the primary strap comprises a tunnel extending in a length direction of the wearable assembly in the middle of the primary strap, the tunnel being formed between two layers of the primary strap, wherein the secondary strap extends through the tunnel.

2. The wearable assembly of claim 1, wherein the primary strap is an elongate article including two portions that are configured to be releasably connectable to one another so that the primary strap forms a loop when the two portions are connected to one another.

3. The wearable assembly of claim 1, wherein the temperature control module is configured to extend through the primary strap and includes a heat sink located relative to the contact so as to be positioned on an opposite side of the primary strap from the contact when the heat sink is disposed through an opening.

4. The wearable assembly of claim 1, wherein the secondary strap is a first secondary strap and the wearable assembly comprises a second secondary strap that is configured to be located on an opposite side of the temperature control module from the first secondary strap, connected to the primary strap, and further configured to adjust a pressure between the contact and the subject when the primary strap encircles the subject.

5. The wearable assembly of claim 4, wherein the first secondary strap and the second secondary strap are configured to be spaced apart by a distance in a width direction, and the contact is wider than the distance.

6. The wearable assembly of claim 1, wherein the secondary strap comprises a stop member to prevent a loose end of the secondary strap from entering the tunnel.

7. A wearable therapeutic device, comprising:
- a strap configured to wrap around a wearer's abdomen and comprising a middle portion, a first end portion extending from the middle portion, and a second end portion extending from an opposite side of the middle portion as the first end portion;
- a control module located on the strap, the control module comprising an opening and a removable battery, wherein the removable battery is configured to be inserted into the control module through the opening to supply power to the wearable therapeutic device, and the removable battery is configured to be removed from the opening by pushing on a portion of the removable battery located opposite the opening with a predetermined amount of force;
- a first fastener attached to the first end portion and a second fastener that is complementary to the first fastener and attached to the second end portion;
- a first heating element located in the first end portion;
- a second heating element located in the middle portion; and
- vibration motors embedded within the middle portion and located to overlap the second heating element, wherein the strap comprises a plurality of layers of fabric, the plurality of layers of fabric comprising at least a first layer facing away from the wearer, a second layer adjacent the first layer, a third layer disposed opposite to the first layer and configured to contact the wearer, and a fourth layer disposed between the second layer and the third layer, wherein the fourth layer includes the vibration motors and a pad embedded therein, wherein the pad is configured to space respective vibration motors apart from the second layer and further configured to isolate the second layer from an impact of the vibration motors, and wherein the pad is formed of a compressible material.

8. The wearable therapeutic device of claim 7, wherein the plurality of layers of fabric include a layer of knitted fabric that includes fibers containing germanium.

9. The wearable therapeutic device of claim 7, wherein the plurality of layers of fabric include a layer of infrared radiation emitting fabric.

10. The wearable therapeutic device of claim 9, wherein the infrared radiation emitting fabric emits infrared radiation passively.

11. The wearable therapeutic device of claim 10, wherein each pad is disposed between each vibration motor and the second heating element.

12. The wearable therapeutic device of claim 10, wherein the plurality of layers of fabric include a padding layer between the second heating element and a surface of the strap.

13. The wearable therapeutic device of claim 12, wherein the vibration motors are located between the second heating element and the padding layer.

14. The wearable therapeutic device of claim 7, wherein the first heating element and the second heating element are panels of carbon fiber or carbon fiber mesh.

15. The wearable therapeutic device of claim 14, wherein a gap exists between the first heating element and the second heating element.

16. The wearable therapeutic device of claim 14, wherein the second end portion is free of any heating elements.

17. A wearable therapeutic device, comprising:

a strap configured for wrapping around a wearer's abdomen, wherein the strap comprises a plurality of layers including:

a wearer facing surface layer that is made at least partially of germanium;

an outer layer facing away from the wearer, a first inner layer adjacent the outer layer; and a second inner layer disposed between the first inner layer and the wearer facing surface layer, a control module located on the strap, the control module comprising an opening and a removable battery, wherein the removable battery is configured to be inserted into the control module through the opening and removed from the opening by pushing on a portion of the removable battery located opposite the opening with a predetermined amount of force; and at least one vibration motor embedded in the strap, wherein the second inner layer includes the at least one vibration motor and at least one pad embedded therein, wherein the at least one pad is configured to space the at least one vibration motor, respectively, apart from the first inner layer and further configured to isolate the first inner layer from an impact of the at least one vibration motor, and wherein the at least one pad is formed of a compressible material.

18. The wearable therapeutic device of claim 17, wherein the wearer facing surface layer is a knitted fabric including fibers of germanium or germanium alloy.

19. The wearable therapeutic device of claim 17, comprising heating features for heating a wearer's back and stomach.

20. The wearable therapeutic device of claim 19, wherein the heating features include a first heating element in a middle portion of the strap and a second heating element spaced from the first heating element and located in a first end portion of the strap, and the strap includes a second end portion extending from an opposite side of the middle portion as the first end portion.

21. The wearable therapeutic device of claim 19, wherein the heating features include a panel of carbon fiber or carbon fiber mesh.

* * * * *